(12) United States Patent
Sabatini et al.

(10) Patent No.: US 8,809,500 B2
(45) Date of Patent: Aug. 19, 2014

(54) COMPLEXES COMPRISING MAMMALIAN RAPTOR POLYPEPTIDE AND MAMMALIAN MTOR POLYPEPTIDE

(71) Applicant: Whitehead Institute For Biomedical Research, Cambridge, MA (US)

(72) Inventors: David M. Sabatini, Cambridge, MA (US); Do-Hyung Kim, Brookline, MA (US); Dos Sarbassov, Chestnut Hill, MA (US)

(73) Assignee: Whitehead Institute For Biomedical Research, Cambridge, MA (US)

( * ) Notice: Subject to any disclaimer, the term of this patent is extended or adjusted under 35 U.S.C. 154(b) by 0 days.

(21) Appl. No.: 13/918,424

(22) Filed: Jun. 14, 2013

(65) Prior Publication Data
US 2014/0004532 A1 Jan. 2, 2014

Related U.S. Application Data

(63) Continuation of application No. 12/900,289, filed on Oct. 7, 2010, now Pat. No. 8,486,643, which is a continuation of application No. 11/788,024, filed on Apr. 18, 2007, now abandoned, which is a continuation of application No. 10/437,421, filed on May 13, 2003, now abandoned.

(60) Provisional application No. 60/378,153, filed on May 14, 2002.

(51) Int. Cl.
*C07K 14/47* (2006.01)
*C07K 14/435* (2006.01)

(52) U.S. Cl.
USPC ......................................... 530/350; 435/69.7

(58) Field of Classification Search
None
See application file for complete search history.

(56) References Cited

U.S. PATENT DOCUMENTS

| | | |
|---|---|---|
| 7,052,870 B2 | 5/2006 | Sabatini et al. |
| 8,486,643 B2 | 7/2013 | Sabatini et al. |
| 2004/0072207 A1 | 4/2004 | Sabatini et al. |
| 2004/0219521 A1 | 11/2004 | Tang et al. |
| 2007/0009936 A1 | 1/2007 | Sabatini et al. |
| 2008/0260721 A1 | 10/2008 | Sabatini et al. |

FOREIGN PATENT DOCUMENTS

| | | |
|---|---|---|
| WO | WO 2004/029276 A2 | 4/2004 |
| WO | WO 2004/029276 A3 | 4/2004 |

OTHER PUBLICATIONS

Andrade, Miguel A. et al., "Heat repeats in the Huntington's disease protein," *Nature Genetics*, 11:115-116 (1995).

Bernard, Phyllis A. et al., "The Respiration of Brain Mitochondria and its Regulation by Monovalent Cation Transport," *Biochimica et Biophysica Acta*, 548:173-186 (1979).
Brown, Eric J. et al., "A Mammalian Protein Targeted by G1-arresting Rapamycin-receptor Complex," *Nature*, 369:756-758 (1994).
Brown, Eric J. et al., "Control of p70 S6 Kinase by Kinase Activity of FRAP in vivo," *Nature*, 377:441-446 and 378:644 (1995).
Brunn, Gregory J. et al., "Phosphorylation of the Translational Repressor PHAS-1 by the Mammalian Target of Rapamycin," *Science*, 277:99-101 (1997).
Brunn, Gregory J. et al., "Direct Inhibition of the Signaling Functions of the Mammalian Target of Rapamycin by the Phosphoinositide 3-Kinase Inhibitors, Wortmannin and LY294002," *The EMBO Journal*, 15(19):5256-5267 (1996).
Burnett, Patrick E. et al., "RAFT1 Phosphorylation of the Translational Regulators p70 S6 Kinase and 4E-BP1," *Proc. Natl. Acad. Sci. USA*, 95:1432-1437 (1998).
Burnett, Patrick E. et al., "Neurabin is a Synaptic Protein Linking p70 S6 Kinase and the Neuronal Cytoskeleton," *Proc. Natl. Acad. Sci. USA*, 95:8351-8356 (1998).
Cameron, Andrew M. et al., "Immunophilin FK506 Binding Protein Associated with Inositol 1,4,5-Trisphosphate Receptor Modulates Calcium Flux," *Proc. Natl. Acad. Sci. USA*, 92:1784-1788 (1995).
Chiu, M. Isabel et al., "RAPT1, a Mammalian Homolog of Yeast Tor, Interacts with the FKBP12/Rapamycin Complex," *Proc. Natl. Acad. Sci. USA*, 91:12574-12578 (1994).
Dennis, Patrick B. et al., "Mammalian TOR:A Homeostatic ATP Sensor," *Science* , 294:1102-1105 (2001).
Dennis, Patrick B. et al. , "Target of Rapamycin (TOR):Balancing the Opposing Forces of Protein Synthesis and Degradation," *Current Opinion in Genetics & Development*, 9:49-54 (1999).
Dudkin, Lorina et al., "Biochemical Correlates of mTOR Inhibition by the Rapamycin Ester CCI-779 and Tumor Growth Inhibition," *Clinical Cancer Research* 7:1758-1764 (2001).
Elbashir, Sayda M. et al., "Duplexes of 21-Nucleotide RNAs Mediate RNA Interference in Cultured Mammalian Cells," *Nature*, 411:494-498 (2001).
Erdjument-Bromage, Hediye et al., "High-Sensitivity Sequencing of Large Proteins:Partial Structure of the Rapamycin-FKBP12 Target," *Protein Science*, 3:2435-2446 (1994).
Fang, Yimin et al., "Phosphatic Acid-Mediated Mitogenic Activation of mTOR Signaling," *Science*, 294:1942-1945 (2001).
Fox, Heather L. et al., "Amino Acids Stimulate Phosphorylation of $p70^{S6k}$ and Organization of Rat Adipocytes into Multicellular Clusters," *Am. J. Physiol.*, 274(1):C206-C213 (1998).
Gingras, Anne-Claude et al., "Regulation of Translation Initiation by FRAP/mTOR," *Genes & Development*, 15:807-826 (2001).

(Continued)

*Primary Examiner* — Christine J Saoud
*Assistant Examiner* — Jon M Lockard
(74) *Attorney, Agent, or Firm* — Hamilton, Brook, Smith & Reynolds, P.C.

(57) ABSTRACT

The present invention relates to isolated raptor nucleic acid molecules of mammalian origin (e.g., human) and complements, portions and variants thereof. Another aspect of the invention are isolated raptor polypeptides of mammalian origin and portions thereof, and antibodies or antigen binding fragments thereof that specifically bind a raptor polypeptide. The present invention also relates to constructs and host cells comprising the nucleic acid molecules described herein. In addition, the present invention relates to uses of the nucleic acid and polypeptide molecules provided herein.

10 Claims, 30 Drawing Sheets

(56) References Cited

OTHER PUBLICATIONS

Hara, Kenta et al., "Regulation of eIF-4E BP1 Phosphorylation by mTOR," *The Journal of Biological Chemistry*, 272(42):26457-26463 (1997).

Hara, Kenta et al., "Amino Acid Sufficiency and mTOR Regulate p70 S6 Kinase and eIF-4E BP1 through a Common Effector Mechanism," *The Journal of Biological Chemistry*, 273(23):14484-14494 (1998).

Hara, Kenta et al., "Raptor, a Binding Partner of Target of Rapamycin (TOR), Mediates TOR Action," *Cell*, 110:177-189 (2002).

Hentges, Kathryn E. et al., "FRAP/mTOR is Required for Proliferation and Patterning During Embryonic Development in the Mouse," *PNAS*, 98(24):13796-13801 (2001).

Hidalgo, Manuel et al., "The Rapamycin-Sensitive Signal Transduction Pathway as a Target for Cancer Therapy," *Ocogene*, 19:6680-6686 (2000).

Isotani, Shuji et al., "Immunopurified Mammalian Target of Rapamycin Phosphorylates and Activates p70 S6 Kinase ÿ in Vitro," *The Journal of Biological Chemistry*, 274(48):34493-34498 (1999).

Keith, Curtis T. et al., "PIK-Related Kinases:DNA Repair, Recombination, and Cell Cycle Checkpoints," *Science*, 270:50-51 (1995).

Kim, D. H. et al., "Raptor and mTOR:Subunits of a Nutrient-Sensitive Complex," *Current Topics in Microbiology and Immunology*, 279:260-270 (2004).

Kim, Do-Hyung et al., "mTOR Interacts with Raptor to Form a Nutrient-Sensitive Complex that Signals to the Cell Growth Machinery," *Cell*, 110:163-175 (2002).

Kim, Do-Hyung et al., "GÿL, a Positive Regulator of the Rapamycin-Sensitive Pathway Required for the Nutrient-Sensitive Interaction between Raptor and mTOR," *Molecular Cell*, 11:895-904 (2003).

Kobe, Bostjan et al., "Turn Up the Heat," *Structure*, 7(5):R91-R97 (1999).

Kumar, Vijay et al., "Regulation of the Rapamycin and FKBP-Target 1/Mammalian Target of Rapamycin and Cap-dependent Initiation of Translation by the c-Abl Protein-tyrosine Kinase," *The Journal of Biological Chemistry*, 275(15):10779-10787 (2000).

Kumar, Vijay et al., "Functional Interaction between RAFT1/FRAP/mTOR and Protein Kinase Cÿ in the Regulation of CAP-Dependent Initiation of Translation," *The EMBO Journal*, 19(5):1087-1097 (2000).

Kunz, Jeannette et al., "Target of Rapamycin in Yeast, TOR2, is an Essential Phosphatidylinositol Kinase Homolog Required for $G_1$ Progression," *Cell*, 73:585-596 (1993).

Lawrence, John C. Jr. et al., "Insulin Signaling and the Control of PHAS-1 Phosphorylation," *Progress in Molecular and Subcellular Biology*, 26:1-31 (2001).

Lee, Soo Jae et al., "The Adoption of a Twisted Structure of Importin-ÿ is Essential for the Protein-protein Interaction Required for Nuclear Transport," *J. Mol. Biol.*, 302:251-264 (2000).

Lynch, Christopher J. et al., "Regulation of Amino Acid-Sensitive TOR Signaling by Leucine Analogues in Adipocytes," *Journal of Cellular Biochemistry*, 77:234-251 (2000).

Majumder, Pradip K. et al., "Targeting of Protein Kinase C ÿ to Mitochondria in the Oxidative Stress Response," *Cell Growth & Differentiation*, 12:465-470 (2001).

Montagne, Jacques et al., "*Drosophila* S6 Kinase:A Regulator of Cell Size," *Science*, 285:2126-2129 (1999).

Oldham, Sean et al., "Genetic and Biochemical Characterization of dTOR, the *Drosophila* Homolog of the Target of Rapamycin," *Genes & Development*, 14:2689-2694 (2000).

Parrott, Louis A. et al., "Osmotic Stress Inhibits p70/85 S6 Kinase through Activation of a Protein Phosphatase," *The Journal of Biological Chemistry*, 274(35):24731-24736 (1999).

Peng, Tao et al., "The Immunosuppressant Rapamycin Mimics a Starvation-Like Signal Distinct from Amino Acid and Glucose Deprivation," *Molecular and Cellular Biology*, 22(15):5575-5584 (2002).

Peterson, Randall T. et al., "FKBP12-Rapamycin-associated Protein (FRAP) Autophosphorylates at Serine 2481 under Translationally Repressive Conditions," *The Journal of Biological Chemistry*, 275(10):7416-7423 (2000).

Rohde, John et al., "The TOR Kinases Link Nutrient Sensing to Cell Growth," *The Journal of Biological Chemistry*, 276(13):9583-9586 (2001).

Sabatini, David M. et al., "RAFT1:A Mammalian Protein that Binds to FKBP12 in a Rapamycin-Dependent Fashion and is Homologous to Yeast TORs," *Cell*, 78:35-43 (1994).

Sabatini, David M. et al., "The Rapamycin and FKBP12 Target (RAFT) Displays Phosphatidylinositol 4-Kinase Activity," *The Journal of Biological Chemistry*, 270(36):20875-20878 (1995).

Sabatini, David M. et al., "Interaction of RAFT1 with Gephyrin Required for Rapamycin-Sensitive Signaling," *Science*, 284:1161-1164 (1999).

Sabatini, David M. et al., "Neural Roles of Immunophilins and Their Ligands," *Molecular Neurobiology*, 15:223-239 (1997).

Sabers, Candace J. et al., "Isolation of a Protein Target of the FKBP12-Rapamycin Complex in Mammalian Cells," *The Journal of Biological Chemistry*, 270(2):815-822 (1995).

Sarbassov, Dos D. et al., "Role of Insulin-Like Growth Factors and Myogenin in the Altered Program of Proliferation and Differentiation in the NFB4 Mutant Muscle Cell Line," *Proc. Natl. Acad. Sci. USA*, 92:10874-10878 (1995).

Schalm, Stefanie S. et al., "TOS Motif-Mediated Raptor Binding Regulates 4E-BP1 Multisite Phosphorylation and Function," *Current Biology*, 13:797-806 (2003).

Schmelzle, Tobias et al., "TOR, a Central Controller of Cell Growth," *Cell*, 103:253-262 (2000).

Shima, Hiroshi et al., "Disruption of the $p70^{s6k}/p85^{s6k}$ Gene Reveals a Small Mouse Phenotype and a New Functional S6 Kinase," *The EMBO Journal*, 17(22):6649-6659 (1998).

Shinozaki-Yabana, Satoko et al., "Novel WD-Repeat Protein Mip1p Facilitates Function of the Meiotic Regulator Mei2p in Fission Yeast," *Molecular and Cellular Biology*, 20(4):1234-1242 (2000).

Smith, Temple F. et al., "The WD Repeat:A Common Architecture for Diverse Functions," *TIBS*, 24:181-185 (1999).

Snyder, Solomon H. et al., "Immunophilins and the Nervous System," *Nature Medicine*, 1(1):32-37 (1995).

Snyder, Solomon H. et al., "Neural Actions of Immunophilin Ligands," *TiPS*, 19:21-26 (1998).

Walensky, Loren D. et al., "The 12 kD FK506 Binding Protein FKBP12 is Released in the Male Reproductive Tract and Stimulates Sperm Mobility," *Molecular Medicine*, 4:502-514 (1998).

Winzeler, Elizabeth A. et al., "Functional Characterization of the *S. Cerevisiae* Genome by Gene Deletion and Parallel Analysis," *Science*, 285:901-906 (1999).

Wolvetang, Ernst J. et al., "Mitochondrial Respiratory Chain Inhibitors Induce Apoptosis," *FEBS Letters*, 339:40-44 (1994).

Xu, Guang et al., "Metabolic Regulation by Leucine of Translation Initiation Through the mTOR-Signaling Pathway by Pancreatic ÿ-Cells," *Diabetes*, 50:353-360 (2001).

Zhang, Hongbing et al., "Regulation of Cellular Growth by the *Drosophila* Target of Rapamycin *dTOR*," *Genes & Development*, 14:2712-2724 (2000).

Zheng, Xiao-Feng et al., "TOR Kinase Domains are Required for Two Distinct Functions, Only One of Which is Inhibited by Rapamycin," *Cell*, 82:121-130 (1995).

Nagase, T., et al., "Prediction of the Coding Sequences of Unidentified Human Genes. XVI. The Complete Sequences of 150 New cDNA Clones from Brain Which Code for Large Proteins in vitro," *DNA Res.* 7(1): 65-73 (2000).

NCBI (Protein), Accession No. BAA92541, "K1AA1203 Protein [*Homo sapiens*]", [online], Mar. 14, 2000, [retrieved on Mar. 4, 2004] Retreived from the Internet <URL: http://www.ncbi.nlm.nih.gov/entrez/viewer.fcgi?db=protein&val=7242961.

NCBI (Nucleotide), Accession No. AY090663, "*Homo Sapiens* Raptor mRNA, complete cds," [online], Jul. 26, 2002 [retrieved on Mar. 4, 2004]. Retreived from the Internet <URL: http://www.ncbi.nlm.nih.gov/entrez/viewer.fcgi?db=nucleotide& val=21979455.

Nojima, Hiroki, et al., "The Mammalian Target of Rapamycin (mTOR) Partner, Raptor, Binds the mTOR Substrates p70 S6 Kinase and 4E-BP1 through Their TOR Signaling (TOS) Motif," *The Journal of Biological Chemistry*, 278(18):15461-15464 (2003).

(56) References Cited

OTHER PUBLICATIONS

Notification of Transmittal of the International Search Report or the Declaration of PCT/US2003/014952, mailed on Oct. 1, 2004.

Sequence Listing and Preliminary Amendment of U.S. Appl. No. 10/437,421, filed Nov. 25, 2003.

Office Action (Restriction) of U.S. Appl. No. 10/437,421, mailed on Jul. 3, 2006.

Reply to Restriction Requirement of U.S. Appl. No. 10/437,421, filed on Jul. 27, 2006.

Office Action of U.S. Appl. No. 10/437,421, mailed on Oct. 18, 2006.

Notice of Abandonment of U.S. Appl. No. 10/437,421, mailed on May 14, 2007.

Office Action (Restriction) of U.S. Appl. No. 11/788,024, mailed on Mar. 20, 2009.

Reply to Restriction Requirement of U.S. Appl. No. 11/788,024, filed on Jun. 22, 2009.

Preliminary Amendment of U.S. Appl. No. 11/788,024, filed on Jun. 26, 2009.

Office Action (Final) of U.S. Appl. No. 11/788,024, mailed on Nov. 10, 2009.

Notice of Abandonment of U.S. Appl. No. 11/788,024, mailed on Oct. 14, 2010.

p180 mRNA sequence that we have (6431 nts)

1. ORF (4008 nts) is indicated in bold. The start and stop codons are underlined.
2. 5'UTR has 362 nts.
3. 3'UTR has 2061 nts.
4. I did not put the 5'UTR sequence that we have not cloned yet.

```
GAGAGCAGGGTCATCGTGAGGCCTGAAGTCTCTTACGCTTTTGGCAGCTCCCCTCGCAG
CCCCTCTGGAAACGTACAGCCTCAGGAGCAGCCAGTGGCTTGGGACCTGGGGTGGTGTG
TGTCTGCGGAGCTTCTTGGGCTGCCCCATTTCCTAGCGGCCCCCACCTCCCCACTTCCC
GCTCAGAGTTAGAGATAAGGATCTCAGACTTTTGCCTGAGTAAGGGTCTCCGCACTCTT
TATCCATTTGGTTTTCGATTTCCCGTTTTTGTTTCTTATTTCACCAATTCTGGTACACG
CTAGTTTTTAAGGCTGGAGGTTCTCGAGCGCTTGCTGCCAAGGACTCCCCCACCCCCTC
CCCCACTGATGGAGTCCGAAATGCTGCAATCGCCTCTTCTGGGCCTGGGGGAGGAAGAT
GAGGCTGATCTTACAGACTGGAACCTACCTTTGGCTTTTATGAAAAAGAGGCACTGTGA
GAAAATTGAAGGCTCCAAATCCTTAGCTCAGAGCTGGAGGATGAAGGATCGGATGAAGA
CAGTCAGTGTTGCCTTAGTTTTGTGCCTGAATGTTGGTGTGGACCCTCCCGATGTGGTG
AAGACCACGCCCTGTGCACGCTTGGAATGCTGGATCGATCCTCTGTCGATGGGTCCTCA
GAAAGCTCTGGAAACCATCGGTGCAAATTTACAGAAGCAGTACGAGAACTGGCAGCCAA
GGGCCCGGTACAAGCAGAGCCTTGACCCAACTGTGGATGAAGTCAAGAAGCTCTGCACG
TCCTTACGTCGCAACGCCAAGGAGGAGCGAGTCCTCTTTCACTACAATGGCCACGGGGT
GCCCCGGCCCACAGTCAACGGGGAGGTCTGGGTCTTCAACAAGAACTACACGCAGTACA
TCCCTCTGTCCATATATGACCTGCAGACGTGGATGGGCAGCCCGTCGATCTTCGTCTAC
GACTGCTCCAATGCTGGCTTGATCGTCAAGTCCTTCAAGCAGTTCGCACTACAGCGGGA
GCAGGAGCTGGAGGTAGCTGCAATCAACCCAAATCACCCTCTTGCTCAGATGCCTTTGC
CTCCGTCGATGAAAAACTGCATCCAGCTGGCAGCCTGCGAGGCCACCGAGCTGCTGCCC
ATGATCCCCGACCTCCCGGCTGACCTATTCACCTCCTGCCTCACCACCCCCATCAAGAT
CGCCCTGCGCTGGTTTTGCATGCAGAAATGTGTCAGTCTGGTGCCTGGCGTCACACTGG
ATTTGATAGAAAAGATCCCTGGCCGCCTGAACGACAGGAGGACGCCCCTGGGTGAACTG
AACTGGATCTTCACAGCCATCACAGACACCATCGCGTGGAACGTGCTCCCCCGGGATCT
CTTCCAAAAGCTCTTCAGACAGGACTTGCTGGTGGCTAGTCTGTTTCGAAATTTTTTAT
TGGCGGAAAGGATTATGAGGTCGTATAACTGCACTCCCGTCAGCAGCCCGCGTCTGCCG
CCCACGTACATGCACGCCATGTGGCAAGCCTGGGACCTGGCTGTTGACATCTGTCTGTC
TCAGCTGCCGACGATCATCGAGGAAGGCACTGCGTTTCGGCACAGCCCGTTCTTCGCCG
AGCAGCTGACCGCATTCCAGGTGTGGCTCACCATGGGCGTGGAGAACCGAAACCCACCC
GAACAGCTGCCCATCGTCCTGCAGGTGCTGTTAAGCCAAGTGCACCGGCTGAGAGCATT
GGACTTGCTTGGAAGATTTTTGGACCTGGGTCCCTGGGCAGTGAGCCTGGCCTTGTCTG
TCGGCATCTTCCCCTACGTGCTGAAGCTGCTCCAGAGCTCGGCCCGAGAGCTGCGGCCA
CTTCTCGTTTTCATCTGGGCCAAGATCCTCGCAGTGGACAGCTCGTGCCAGGCGGACCT
CGTGAAGGACAACGGCCACAAGTACTTCCTGTCGGTCCTGGCGGACCCCTACATGCCAG
CTGAACACCGGACCATGACGGCTTTCATTCTCGCCGTGATCGTCAACAGCTATCACACG
GGGCAGGAAGCCTGCCTTCAGGGAAACCTCATTGCCATCTGCCTGGAGCAGCTCAACGA
CCCGCACCCCTTGCTGCGCCAGTGGGTGGCCATCTGCCTCGGCAGGATCTGGCAGAACT
TCGACTCGGCGAGGTGGTGCGGCGTGAGGGACAGCGCTCATGAAGCTCTACAGCCTC
CTCTCCGACCCCATTCCCGAGGTCCGCTGCGCAGCGGTCTTCGCCCTTGGCACGTTCGT
```

FIG. 1A

```
GGGCAACTCTGCAGAGAGGACGGACCACTCCACCACCATCGACCACAACGTGGCCATGA
TGCTGGCCCAGCTGGTCAGCGACGGGAGCCCCATGGTCCGGAAGGAGCTGGTGGTGGCT
CTGAGTCATCTTGTGGTTCAGTATGAAAGCAATTTCTGCACCGTGGCCCTGCAGTTCAT
AGAAGAGGAAAAGAACTACGCCTTGCCTTCTCCAGCAACCACAGAGGGAGGGAGTTTGA
CCCCAGTGCGAGACAGCCCGTGCACCCCAGACTTCGTTCTGTGAGCTCCTATGGAAAC
ATCCGTGCTGTCGCCACAGCCAGGAGCCTCAACAAATCTTTGCAGAACCTGAGTTTGAC
AGAGGAATCTGGTGGCGCGGTGGCGTTCTCCCCGGAAACCTCAGCACCAGCAGCAGCG
CCAGCAGCACCCTGGGCAGCCCCGAGAATGAGGAGCATATCCTGTCCTTCGAGACCATC
GACAAGATGCGCCGCGCCAGCTCCTACTCCTCCCTCAACTCCCTCATCGGAGTTTCCTT
TAACAGTGTTTACACTCAGATTTGGAGAGTCCTGCTGCACCTGGCTGCTGACCCCTATC
CAGAGGTCTCGGACGTGGCCATGAAAGTACTCAACAGCATCGCCTACAAGGCCACCGTG
AACGCCCGGCCGCAGCGCGTCCTGGACACCTCCTCCCTCACGCAGTCGGCCCCCGCCAG
CCCCACCAACAAGGGCGTGCACATCCACCAGGCGGGGGCTCCCCTCCGGCGTCCAGCA
CCAGCAGCTCCAGCCTGACCAACGATGTGGCCAAGCAGCCGGTCAGCCGAGACTTGCCT
TCTGGCCGGCCGGGCACCACAGGCCCCGCTGGGGCGCAGTACACCCCTCACTCCCACCA
GTTCCCCCGGACACGGAAGATGTTCGACAAGGGCCCAGAGCAGACTGCGGACGACGCGG
ACGATGCTGCTGGACACAAAAGTTTCATCTCCGCCACGGTGCAGACGGGGTTCTGCGAC
TGGAGCGCCCGCTATTTTGCCCAGCCCGTCATGAAGATCCCAGAAGAGCACGACCTGGA
GAGTCAGATCCGCAAGGAGCGGGAGTGGCGGTTCCTGCGAAACAGCCGTGTCAGGAGGC
AGGCCCAGCAAGTCATTCAGAAGGGCATTACGAGATTGGACGACCAAATATTTCTGAAC
AGGAACCCCGGCGTCCCCTCTGTGGTGAAATTCCACCCCTTCACGCCGTGCATCGCTGT
AGCCGACAAGGACAGCATCTGCTTTTGGGACTGGGAGAAAGGGGAGAAGCTGGATTATT
TCCACAATGGGAACCCTCGGTACACGAGGGTCACTGCCATGGAGTATCTGAATGGCCAG
GACTGCTCGCTTCTGCTGACGGCCACAGACGATGGTGCCATCAGGGTCTGGAAGAATTT
TGCTGATTTGGAAAAGAACCCAGAGATGGTGACCGCGTGGCAGGGGCTCTCGGACATGC
TGCCAACGACGCGAGGAGCTGGGATGGTGGTGGACTGGGAGCAGGAGACCGGCCTCCTC
ATGAGCTCAGGAGACGTGCGGATCGTCCGGATCTGGGACACAGACCGTGAGATGAAGGT
GCAGGACATCCCTACGGGCGCAGACAGCTGTGTGACGAGTCTGTCCTGTGATTCCCACC
GCTCACTCATCGTGGCTGGCCTCGGTGACGGCTCCATCCGCGTCTACGACAGAAGGATG
GCACTCAGCGAATGCCGCGTCATGACGTACCGGGAGCACACAGCCTGGGTGGTGAAGGC
CTCCCTGCAGAAGCGTCCCGACGGCCACATCGTGAGTGTGAGCGTCAATGGAGATGTGC
GCATCTTTGATCCCCGGATGCCTGAGTCGGTAAATGTGCTTCAGATCGTGAAGGGGCTG
ACGGCCCTGGACATCCACCCCCAGGCGGACCTGATCGCATGTGGCTCCGTCAATCAGTT
CACCGCCATCTACAACAGCAGCGGAGAGCTCATCAACAACATCAAGTACTACGACGGCT
TCATGGGCCAGCGGGTCGGCGCCATCAGCTGCCTGGCCTTCCACCCGCACTGGCCTCAC
CTGGCCGTGGGAAGCAACGACTACTACATCTCCGTGTACTCGGTGGAGAAGCGTGTCAG
ATAGCGGCGTGACCCGGGCCCACCAGGCCACGGCCGCCTGCTGTACATAGTGAAGCTGT
CACTCGCCGGGCACGGGGCGTCGGCTGCTGCGGCCCCGCAGTGTGAACGTTGGCTGCT
GCCTTAGCTGCTGATGACGGCAGGAGGCCCTGCTACTCGCTTTTGTCTGTCTTCGCTG
TCGTGTCTGGAATGTCAGGGAAGGGGAGGGCTCGGGTTGACGGTGGCTTCCCACTGAGC
ACCAGCATCCAGGTGCACCCCGCGGCCACGGCGCCTCTGTCCCTCTCCTGTTCTGTGT
TTCTCTGAGACGCTGAAAGGGAAACACCTCACTTTATTTCCATGTAATCAGAGCATTA
GCTGCAGAAAACCCCAGACAGAGCCCTGGCGGAGAGGCAGGCCTGGGGCTCCTACG
GGTCCCTGGGGCAGCTGTCCCCATCAGGCCAAGAGCGAGCGAGAGGCGCTGCCCCAGCC
AGGCCCACCACCTCTCACAGTCAGTGCACGCAAGCAGGACATTTCCTAGCCAGCTGGG
GGACACTGGAAATTCGGGAAACCAAGAGAGAGGAAGAAGGAGACGCCCTCCAACTGGC
GGGTGTGAAGGAAGCCGCCCAGGGGTCCGGGCTGTCCTTGGCCGCTGGCAGCATCACTG
AGCAGGAAGCGCACAGCCCACCCTCCCCGCACCTCCAGGTCTCTGGACTCCAGTTTTGG
```

FIG. 1B

```
CCCCTCTCACACAGAGCTGTCAGCAGGGGCCGCTGTGGCGGTGCACAGGGGAGGCAGGT
CCTTGGCGAGGTAGCCCCTGCCTTAATCCACGGGGCTCCTTTCCCTCCGAAGGGCTGCT
CTTCCCCACAGGCGCGGGACAGCAGCCCGACCTGTGGTCTCCATGCCTGTGCCCTCAC
ACAGGTGTAGCACACGCATGTGCAGATGGCACCACGGCCGGCACCTGGGGGCACACACA
TGCAGGCGGCGTGGTCTCCCTGCTCTGTCCCCACACGTTCCTCACATACAGGCAAGAGG
CACTGCCGGGTCCCGGACGGCTCCGGGTGACACCAGCCCCGTCTCCAGCCTTGAGCCGC
CCATGCTGATGCGACCTCGGCTGACAGCTGGGCCTGTGGTGCAGACAGGAGCTGTGTGG
ACAGTCCCGCCCAGGAGGGGCCGCAGGGCGTGTATGAGCAGTTTTGCAAACAGAACACA
ACCACAATGATGGTATTTTGAAAAGTGTTCTTTCCGTGTTCGTCGGGAATCAGGATTAT
TGAGAGGTGAAGGAGCCAGGTGGCTTCATTCTGGCGGTGAGAGGCCCATGACCACGGGA
GTGAGAGCTGGTGTGGCGAGGCCCGGCTCTCCTGCGGTGTGGCTGGTGGCCTGCCGTGG
CCAAGAGCATCTTCTGGGTGGATGGAACCCTGCCTGGTCACATTTGGCCAGAGACACAC
CTGGCCCTCAGGGGGCTGAGCTGGAGACTGAGCTGGGGCTGGCCGGGACGTGACAAGGC
AGGACAGAGGCGGCCCCTCCGCTGCTCCTTTTTGGAATGCGAGCTCCCACCAGAAGAAG
GTTCCGGCACGAATCCCATCCCCACGTCTGGGCCGAGAAAGCAGCCCGGGTCCGGAAGG
TGTAGAGAGTCCCGGCCTCACTCAGCTCACAGGGCGTGCCAGGCGGCAACACCAGAATC
TTCCAGAAGCCCAGCTCCACCCGCACACGCAGCTTCCCATCCAGTCCTTCAACTCAATT
CTTACCCAACACGCGTTTCCGTTTGTTTTGAGACAAAATCACCACCTGTCAAAAGGCAG
GTGGCTCCAGAGGGGTCAAGACCCCCCCCCCGCCCCCGCTCCACCCTGGAGCCCACCC
CCATGGGCACTGCGTGCCGCCTGCACGTGGGCTGTCTTCACAGGTCTGATGTGAAAATT
CAATCACGACGTTAACCGGCTCGAGAGAGCGCCGGCCTAGAGGCTCATTATCTATTTAT
TTTACCAAACGCGAATTGAGACGGACTTTGACAAAACACGAAATGGTAATGTGAAGCTA
AGAGCAGAGAGTGACCAACAGTAAACAACACGCGCAGAAAAAAAAAAAAAAAAAAAAAA
```

FIG. 1C p180 protein full-length (1335 amino acids)

```
MESEMLQSPLLGLGEEDEADLTDWNLPLAFMKKRHCEKIEGSKSLAQSWRMKDRMKTVS
VALVLCLNVGVDPPDVVKTTPCARLECWIDPLSMGPQKALETIGANLQKQYENWQPRAR
YKQSLDPTVDEVKKLCTSLRRNAKEERVLFHYNGHGVPRPTVNGEVWVFNKNYTQYIPL
SIYDLQTWMGSPSIFVYDCSNAGLIVKSFKQFALQREQELEVAAINPNHPLAQMPLPPS
MKNCIQLAACEATELLPMIPDLPADLFTSCLTTPIKIALRWFCMQKCVSLVPGVTLDLI
EKIPGRLNDRRTPLGELNWIFTAITDTIAWNVLPRDLFQKLFRQDLLVASLFRNFLLAE
RIMRSYNCTPVSSPRLPPTYMHAMWQAWDLAVDICLSQLPTIIEEGTAFRHSPFFAEQL
TAFQVWLTMGVENRNPPEQLPIVLQVLLSQVHRLRALDLLGRFLDLGPWAVSLALSVGI
FPYVLKLLQSSARELRPLLVFIWAKILAVDSSCQADLVKDNGHKYFLSVLADPYMPAEH
RTMTAFILAVIVNSYHTGQEACLQGNLIAICLEQLNDPHPLLRQWVAICLGRIWQNFDS
ARWCGVRDSAHEKLYSLLSDPIPEVRCAAVFALGTFVGNSAERTDHSTTIDHNVAMMLA
QLVSDGSPMVRKELVVALSHLVVQYESNFCTVALQFIEEEKNYALPSPATTEGGSLTPV
RDSPCTPRLRSVSSYGNIRAVATARSLNKSLQNLSLTEESGGAVAFSPGNLSTSSSASS
TLGSPENEEHILSFETIDKMRRASSYSSLNSLIGVSFNSVYTQIWRVLLHLAADPYPEV
SDVAMKVLNSIAYKATVNARPQRVLDTSSLTQSAPASPTNKGVHIHQAGGSPPASSTSS
SSLTNDVAKQPVSRDLPSGRPGTTGPAGAQYTPHSHQFPRTRKMFDKGPEQTADDADDA
AGHKSFISATVQTGFCDWSARYFAQPVMKIPEEHDLESQIRKEREWRFLRNSRVRRQAQ
QVIQKGITRLDDQIFLNRNPGVPSVVKFHPFTPCIAVADKDSICFWDWEKGEKLDYFHN
GNPRYTRVTAMEYLNGQDCSLLLTATDDGAIRVWKNFADLEKNPEMVTAWQGLSDMLPT
TRGAGMVVDWEQETGLLMSSGDVRIVRIWDTDREMKVQDIPTGADSCVTSLSCDSHRSL
IVAGLGDGSIRVYDRRMALSECRVMTYREHTAWVVKASLQKRPDGHIVSVSVNGDVRIF
DPRMPESVNVLQIVKGLTALDIHPQADLIACGSVNQFTAIYNSSGELINNIKYYDGFMG
QRVGAISCLAFHPWPHLAVGSNDYYISVYSVEKRVR
```

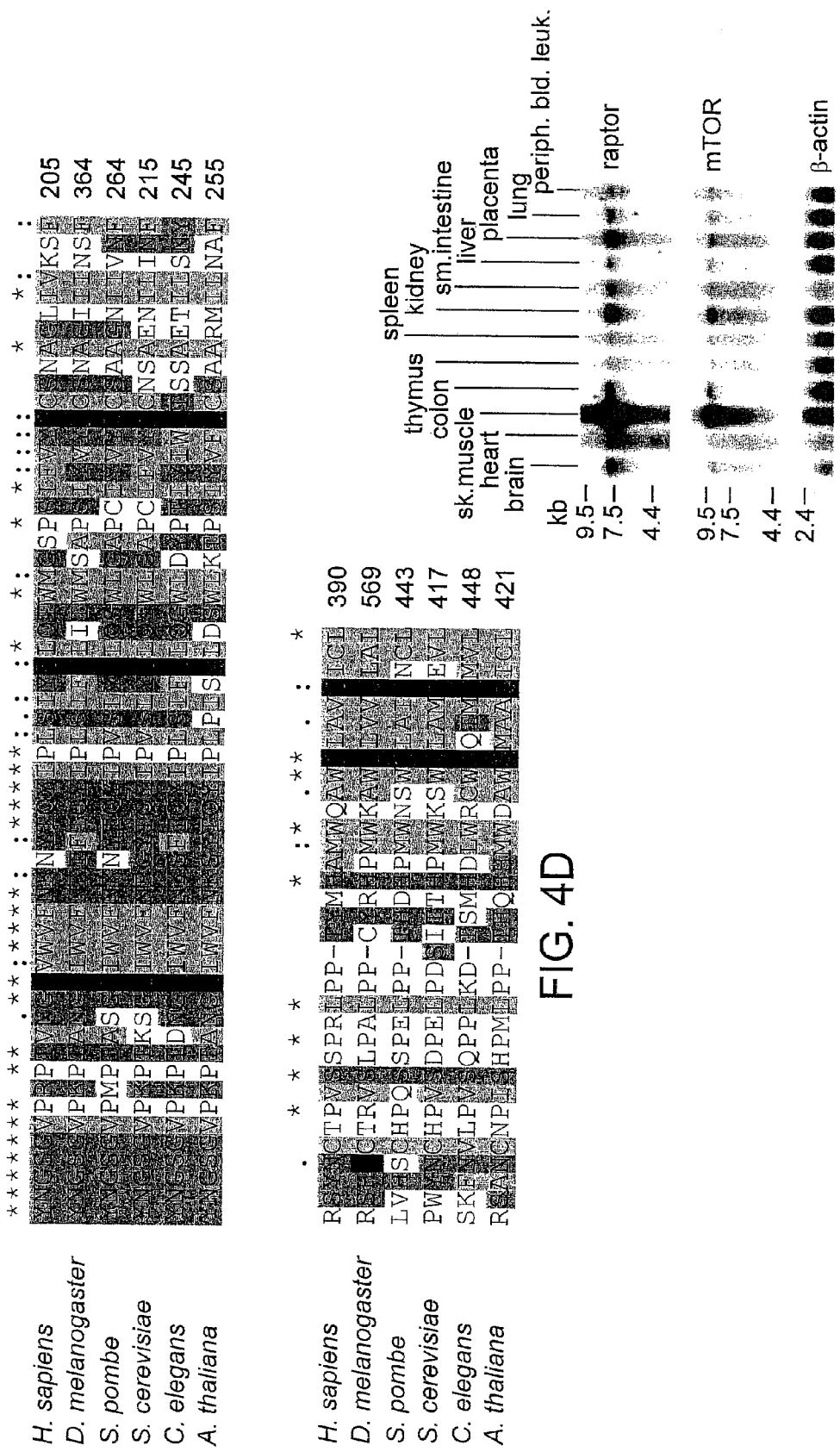

```
H. sapiens       ----------------------------------------------------------------
D. melanogaster  MTSAVRAKSAAAAVGVAVESGSSNGSVADQEAASSKAVISVLIRKYMKYVFAP
S. pombe         ----------------MNDRISMVSGSSRARRSVLSICITTGSDRYMLNSNIAMENGVDTASSMID
S. cerevisiae    ----------------------------------------------------------------
C. elegans       --------------------------------------------MRQKVQRSALAR
A. thaliana      ----------------MALGDLMVSRFSQSSVSLVSNHRMDEDCVSS H. sapiens       ----------------LTDWNLPLPLAFMKKRHCFKIEGS
D. melanogaster  PRDSSTKTERLKMIQILGMPPARSLEGERIRDRCPLSLQTKRHKERIQAM
S. pombe         --------------------KRHRG----VISKKNAIR
S. cerevisiae    ----------------KRHKTNGNPIPEEDKQRDVNRY
C. elegans       NVERVTLYLQEPRHVFIAGSMEDEWDC
A. thaliana      MAYLPQTIVLCELRHDASEASAPLGTSE

FIG. 11A
```

|  | | | |  | | position |
|---|---|---|---|---|---|---|
| H. sapiens | | | | | | 20 |
| D. melanogaster | VRHIEQISEIQASNCQEIASLGSIRELIRIRKW | | | | | 150 |
| S. pombe | | | | | | 87 |
| S. cerevisiae | | | | | | 28 |
| C. elegans | | | | | | 50 |
| A. thaliana | | | | | | 63 |

| | | | | | position |
|---|---|---|---|---|---|
| H. sapiens | ALTIGANLQKQYNWQPR--ARYRQSLEPTVDEV | 130 |
| D. melanogaster | AMELIGSNLQMQYLRWQPR--ARYKCNDPIVDDV | 289 |
| S. pombe | ALAIGKNLQQYTHSMP----TRYHYLPAIV | 189 |
| S. cerevisiae | AIQIGKNLQAQYTHSIR----TBYIRQSLDPCVDDV | 140 |
| C. elegans | AAIEIGLSTQRAYKWQPRSKTRYKICTPPIDDV | 170 |
| A. thaliana | ALTIGKNISTQYKRWQPR--ARYKVQLEPTVDEV | 179 |

| | | |
|---|---|---|
| H. sapiens | AQMPIP--PSMKNCIQLAAQEATILLPMI-PDIP | 259 |
| D. melanogaster | NQVQHTNQMSYKNSIHIAACAANILTPMN-AQIP | 438 |
| S. pombe | --PNVLAMPSHTSCIQLAACPKHTLPMN-PDLP | 314 |
| S. cerevisiae | --AAPSPESAYQLEQLASCTSDLLLMS-PILP | 265 |
| C. elegans | EALGEPEKYPRYNDIHIAACSAGQWIPMSNPHEP | 319 |
| A. thaliana | ----SSRDLILAACDVHLTPQS-VEEP | 292 |

| | | |
|---|---|---|
| H. sapiens | RTMRSYNCTPVSSPRIPP--TYMHAMWQAWDTAVDT | 388 |
| D. melanogaster | TIIRSHCTPVSLPAIPP--CYRHPMWKAWLVVDL | 567 |
| S. pombe | IMLVHSCHPQSSPELPP--THDHPMWNSWDTATEN | 441 |
| S. cerevisiae | RTMPWYNGHPVSDPELPDSITTHPMWKSWDLAMDE | 415 |
| C. elegans | RVMSKFNVLPVSQPPLKD--NSMHDIWRCWDQTMEM | 446 |
| A. thaliana | RTMRSANCNPISHPMLPP--THQHMWDAWDMAATI | 419 |

Block 3

| | | |
|---|---|---|
| H. sapiens | NRNPPFQLPIVLLSQVHLRAIDHLGRFLLG | 460 |
| D. melanogaster | SRTPPFQLPIVLLSQVHLRAIEALEARFLDLG | 639 |
| S. pombe | SKKPPDHLPIVLLSQVHLRAILLSKFLELG | 518 |
| S. cerevisiae | VRHPPFQLPIVLLSQVHLRAIVLLSFLLG | 565 |
| C. elegans | EGTPPLQHPMVLLQVLLSQAHRVRAILIARTLEG | 552 |
| A. thaliana | HKKPPFQLPIVLLSQCHRFRAIVILGFLMG | 492 |

SEQUENCE LISTING

<160> NUMBER OF SEQ ID NOS: 28

<210> SEQ ID NO 1
<211> LENGTH: 6431
<212> TYPE: DNA
<213> ORGANISM: homo sapien

<400> SEQUENCE: 1

| | | | | | | |
|---|---|---|---|---|---|---|
| gagagcaggg | tcatcgtgag | gcctgaagtc | tcttacgctt | ttggcagctc | ccctcgcagc | 60 |
| ccctctggaa | acgtacagcc | tcaggagcag | ccagtggctt | gggacctggg | gtggtgtgtg | 120 |
| tctgcggagc | ttcttgggct | gccccatttc | ctagcggccc | ccacctcccc | acttcccgct | 180 |
| cagagttaga | gataaggatc | tcagactttt | gcctgagtaa | gggtctccgc | actctttatc | 240 |
| catttggttt | tcgatttccc | gttttttgttt | cttatttcac | caattctggt | acacgctagt | 300 |
| ttttaaggct | ggaggttctc | gagcgcttgc | tgccaaggac | tcccccaccc | cctcccccac | 360 |
| tgatggagtc | cgaaatgctg | caatcgcctc | ttctgggcct | gggggaggaa | gatgaggctg | 420 |
| atcttacaga | ctggaaccta | cctttggctt | ttatgaaaaa | gaggcactgt | gagaaaattg | 480 |
| aaggctccaa | atccttagct | cagagctgga | ggatgaagga | tcggatgaag | acagtcagtg | 540 |
| ttgccttagt | tttgtgcctg | aatgttggtg | tggaccctcc | cgatgtggtg | aagaccacgc | 600 |
| cctgtgcacg | cttggaatgc | tggatcgatc | tctgtcgat | gggtcctcag | aaagctctgg | 660 |
| aaaccatcgg | tgcaaattta | cagaagcagt | acgagaactg | gcagccaagg | gcccggtaca | 720 |
| agcagagcct | tgacccaact | gtggatgaag | tcaagaagct | ctgcacgtcc | ttacgtcgca | 780 |
| acgccaagga | ggagcgagtc | ctctttcact | acaatggcca | cggggtgccc | cggcccacag | 840 |
| tcaacgggga | ggtctgggtc | ttcaacaaga | actacacgca | gtacatccct | ctgtccatat | 900 |
| atgacctgca | gacgtggatg | gcagcccgt | cgatcttcgt | ctacgactgc | tccaatgctg | 960 |
| gcttgatcgt | caagtccttc | aagcagttcg | cactacagcg | ggagcaggag | ctggaggtag | 1020 |
| ctgcaatcaa | cccaaatcac | cctcttgctc | agatgccttt | gcctccgtcg | atgaaaaact | 1080 |
| gcatccagct | ggcagcctgc | gaggccaccg | agctgctgcc | catgatcccc | gacctcccgg | 1140 |
| ctgacctatt | cacctcctgc | tcaccaccc | ccatcaagat | cgccctgcgc | tggttttgca | 1200 |
| tgcagaaatg | tgtcagtctg | gtgcctggcg | tcacactgga | tttgatagaa | agatccctg | 1260 |
| gccgcctgaa | cgacaggagg | acgccccctgg | gtgaactgaa | ctggatcttc | acagccatca | 1320 |
| cagacaccat | cgcgtggaac | gtgctccccc | gggatctctt | ccaaaagctc | ttcagacagg | 1380 |
| acttgctggt | ggctagtctg | tttcgaaatt | ttttattggc | ggaaaggatt | atgaggtcgt | 1440 |
| ataactgcac | tcccgtcagc | agcccgcgtc | tgccgcccac | gtacatgcac | gccatgtggc | 1500 |
| aagcctggga | cctggctgtt | gacatctgtc | tgtctcagct | gccgacgatc | atcgaggaag | 1560 |
| gcactgcgtt | tcggcacagc | ccgttcttcg | ccgagcagct | gaccgcattc | caggtgtggc | 1620 |
| tcaccatggg | cgtggagaac | cgaaacccac | ccgaacagct | gcccatcgtc | ctgcaggtgc | 1680 |
| tgttaagcca | agtgcaccgg | ctgagagcat | tggacttgct | tggaagatttt | ttggacctgg | 1740 |
| gtccctgggc | agtgagcctg | gccttgtctg | tcggcatctt | ccctacgtg | ctgaagctgc | 1800 |
| tccagagctc | ggcccgagag | ctgcggccac | ttctcgttttt | catctgggcc | aagatcctcg | 1860 |
| cagtggacag | ctcgtgccag | gcggacctcg | tgaaggacaa | cggccacaag | tacttcctgt | 1920 |
| cggtcctggc | ggaccctac | atgccagctg | aacaccggac | catgacggct | ttcattctcg | 1980 |
| ccgtgatcgt | caacagctat | cacacggggc | aggaagcctg | ccttcaggga | aacctcattg | 2040 |
| ccatctgcct | ggagcagctc | aacgacccgc | accccttgct | gcgccagtgg | gtggccatct | 2100 |

```
gcctcggcag gatctggcag aacttcgact cggcgaggtg gtgcggcgtg agggacagcg    2160
ctcatgagaa gctctacagc ctcctctccg accccattcc cgaggtccgc tgcgcagcgg    2220
tcttcgccct tggcacgttc gtgggcaact ctgcagagag gacggaccac tccaccacca    2280
tcgaccacaa cgtggccatg atgctggccc agctggtcag cgacgggagc cccatggtcc    2340
ggaaggagct ggtggtggct ctgagtcatc ttgtggttca gtatgaaagc aatttctgca    2400
ccgtggccct gcagttcata gaagaggaaa agaactacgc cttgccttct ccagcaacca    2460
cagagggagg gagtttgacc ccagtgcgag acagcccgtg cacccccaga cttcgttctg    2520
tgagctccta tggaaacatc cgtgctgtcg ccacagccag gagcctcaac aaatctttgc    2580
agaacctgag tttgacagag gaatctggtg gcgcggtggc gttctccccc ggaaacctca    2640
gcaccagcag cagcgccagc agcacccctgg gcagccccga gaatgaggag catatcctgt    2700
ccttcgagac catcgacaag atgcgccgcg ccagctccta ctcctccctc aactccctca    2760
tcggagtttc ctttaacagt gtttacactc agatttggag agtcctgctg cacctggctg    2820
ctgacccta tccagaggtc tcggacgtgg ccatgaaagt actcaacagc atcgcctaca    2880
aggccaccgt gaacgcccgg ccgcagcgcg tcctggacac ctcctccctc acgcagtcgg    2940
cccccgccag ccccaccaac aagggcgtgc acatccacca ggcgggggc tcccctccgg    3000
cgtccagcac cagcagctcc agcctgacca acgatgtggc caagcagccg gtcagccgag    3060
acttgccttc tggccggccg ggcaccacag gccccgctgg ggcgcagtac acccctcact    3120
cccaccagtt cccccggaca cggaagatgt tcgacaaggg cccagagcag actgcggacg    3180
acgcggacga tgctgctgga cacaaaagtt tcatctccgc cacggtgcag acggggttct    3240
gcgactggag cgccccgctat tttgcccagc ccgtcatgaa gatcccagaa gagcacgacc    3300
tggagagtca gatccgcaag gagcgggagt ggcggttcct gcgaaacagc cgtgtcagga    3360
ggcaggccca gcaagtcatt cagaagggca ttacgagatt ggacgaccaa atatttctga    3420
acaggaaccc cggcgtcccc tctgtggtga aattccaccc cttcacgccg tgcatcgctg    3480
tagccgacaa ggacagcatc tgcttttggg actgggagaa aggggagaag ctggattatt    3540
tccacaatgg gaaccctcgg tacacgaggg tcactgccat ggagtatctg aatggccagg    3600
actgctcgct tctgctgacg gccacagacg atggtgccat cagggtctgg aagaattttg    3660
ctgatttgga aaagaaccca gagatggtga ccgcgtggca ggggctctcg gacatgctgc    3720
caacgacgcg aggagctggg atggtggtgg actgggagca ggagaccggc ctcctcatga    3780
gctcaggaga cgtgcggatc gtccggatct gggacacaga ccgtgagatg aaggtgcagg    3840
acatccctac gggcgcagac agctgtgtga cgagtctgtc ctgtgattcc caccgctcac    3900
tcatcgtggc tggcctcggt gacggctcca tccgcgtcta cgacagaagg atggcactca    3960
gcgaatgccg cgtcatgacg taccgggagc acacagcctg ggtggtgaag gcctccctgc    4020
agaagcgtcc cgacggccac atcgtgagtg tgagcgtcaa tggagatgtg cgcatctttg    4080
atccccggat gcctgagtcg gtaaatgtgc ttcagatcgt gaagggctg acggccctgg    4140
acatccaccc ccaggcggac ctgatcgcat gtggctccgt caatcagttc accgccatct    4200
acaacagcag cggagagctc atcaacaaca tcaagtacta cgacgcttc atgggccagc    4260
gggtcggcgc catcagctgc ctggccttcc acccgcactg gcctcacctg gccgtgggaa    4320
gcaacgacta ctacatctcc gtgtactcgg tggagaagcg tgtcagatag cggcgtgacc    4380
cgggcccacc aggccacggc cgcctgctgt acatagtgaa gctgtcactc gccggggcac    4440
```

```
gggggcgtcgg ctgctgcggc cccgcagtgt gaacgttggc tgctgcctta gctgctgatg      4500
acggcaggag ggccctgcta ctcgcttttg tctgtcttcg ctgtcgtgtc tggaatgtca      4560
gggaagggga gggctcgggt tgacggtggc ttcccactga gcaccagcat ccaggtgcac      4620
ccccgcggcc acggcgcctc tgtccctctc ctgttctgtg tttctctgag acgctgaaag      4680
gggaaacacc tcactttatt tccatgtaat cagagcatta gctgcagaaa aaccccagda      4740
cagagccctg gcggagaggc aggcgctggg gctcctacgg gtccctgggg cagctgtccc      4800
catcaggcca agagcgagcg agaggcgctg ccccagccag gcccaccacc tctcacagtc      4860
agtgcacgca agcagggaca tttcctagcc agctggggga cactggaaat tcgggaaacc      4920
aagagagagg aagaaggaga cgcccctcca actggcgggt gtgaaggaag ccgcccaggg      4980
gtccgggctg tccttggccg ctggcagcat cactgagcag gaagcgcaca gcccacccte      5040 cccgcacctc caggtctctg gactccagtt ttggcccctc tcacacagag ctgtcagcag      5100
gggccgctgt ggcggtgcac aggggaggca ggtccttggc gaggtagccc ctgccttaat      5160
ccacggggct cctttccctc cgaagggctg ctcttcccca caggcgcggg acagcagcc      5220 cgacctgtgg tctccatgcc tgtgccctca caggtgta gcacgcat gtgcagatgg      5280 caccacggcc ggcacctggg ggcacacaca tgcaggcggc gtggtctccc tgctctgtcc      5340
ccacacgttc ctcacataca ggcaagaggc actgccgggt ccggacggc tccgggtgac      5400 accagccccg tctccagcct tgagccgccc atgctgatgc gacctcggct gacagctggg      5460
cctgtggtgc agacaggagc tgtgtggaca gtcccgccca ggaggggccg cagggcgtgt      5520
atgagcagtt ttgcaaacag aacacaacca caatgatggt attttgaaaa gtgttctttc      5580
cgtgttcgtc gggaatcagg attattgaga ggtgaaggag ccaggtggct tcattctggc      5640
ggtgagaggc ccatgaccac gggagtgaga gctggtgtgg cgaggcccgg ctctcctgcg      5700
gtgtggctgg tggcctgccg tggccaagag catcttctgg gtggatggaa ccctgcctgg      5760
tcacatttgg ccagagacac acctggcccct caggggggctg agctggagac tgagctgggg      5820
ctggccggga cgtgacaagg caggacagag gcggcccctc cgctgctcct ttttggaatg      5880
cgagctccca ccagaagaag gttccggcac gaatcccatc cccacgtctg ggccgagaaa      5940
gcagcccggg tccggaaggt gtagagagtc ccggcctcac tcagctcaca gggcgtgcca      6000
ggcggcaaca ccagaatctt ccagaagccc agctccaccc gcacgcag cttcccatcc      6060 agtccttcaa ctcaattctt acccaacacg cgtttccgtt tgttttgaga caaaatcacc      6120
acctgtcaaa aggcaggtgg ctccagaggg gtcaagaccc ccccccgc cccgctcca      6180 ccctggagcc cacccccatg ggcactgcgt gccgcctgca cgtgggctgt cttcacaggt      6240
ctgatgtgaa aattcaatca cgacgttaac cggctcgaga gagcgccggc ctagaggctc      6300
attatctatt tattttacca aacgcgaatt gagacggact ttgacaaaac acgaaatggt      6360
aatgtgaagc taagagcaga gagtgaccaa cagtaaacaa cacgcgcaga aaaaaaaaa      6420 aaaaaaaaaa a                                                          6431
```

<210> SEQ ID NO 2
<211> LENGTH: 1335
<212> TYPE: PRT
<213> ORGANISM: homo sapien

<400> SEQUENCE: 2

```
Met Glu Ser Glu Met Leu Gln Ser Pro Leu Leu Gly Leu Gly Glu Glu
 1               5                  10                  15
```

```
Asp Glu Ala Asp Leu Thr Asp Trp Asn Leu Pro Leu Ala Phe Met Lys
             20                  25                  30

Lys Arg His Cys Glu Lys Ile Glu Gly Ser Lys Ser Leu Ala Gln Ser
         35                  40                  45

Trp Arg Met Lys Asp Arg Met Lys Thr Val Ser Val Ala Leu Val Leu
     50                  55                  60

Cys Leu Asn Val Gly Val Asp Pro Pro Asp Val Val Lys Thr Thr Pro
 65                  70                  75                  80

Cys Ala Arg Leu Glu Cys Trp Ile Asp Pro Leu Ser Met Gly Pro Gln
                 85                  90                  95

Lys Ala Leu Glu Thr Ile Gly Ala Asn Leu Gln Lys Gln Tyr Glu Asn
            100                 105                 110

Trp Gln Pro Arg Ala Arg Tyr Lys Gln Ser Leu Asp Pro Thr Val Asp
        115                 120                 125

Glu Val Lys Lys Leu Cys Thr Ser Leu Arg Arg Asn Ala Lys Glu Glu
    130                 135                 140

Arg Val Leu Phe His Tyr Asn Gly His Gly Val Pro Arg Pro Thr Val
145                 150                 155                 160

Asn Gly Glu Val Trp Val Phe Asn Lys Asn Tyr Thr Gln Tyr Ile Pro
                165                 170                 175

Leu Ser Ile Tyr Asp Leu Gln Thr Trp Met Gly Ser Pro Ser Ile Phe
            180                 185                 190

Val Tyr Asp Cys Ser Asn Ala Gly Leu Ile Val Lys Ser Phe Lys Gln
        195                 200                 205

Phe Ala Leu Gln Arg Glu Gln Glu Leu Glu Val Ala Ala Ile Asn Pro
    210                 215                 220

Asn His Pro Leu Ala Gln Met Pro Leu Pro Pro Ser Met Lys Asn Cys
225                 230                 235                 240

Ile Gln Leu Ala Ala Cys Glu Ala Thr Glu Leu Leu Pro Met Ile Pro
                245                 250                 255

Asp Leu Pro Ala Asp Leu Phe Thr Ser Cys Leu Thr Thr Pro Ile Lys
            260                 265                 270

Ile Ala Leu Arg Trp Phe Cys Met Gln Lys Cys Val Ser Leu Val Pro
        275                 280                 285

Gly Val Thr Leu Asp Leu Ile Glu Lys Ile Pro Gly Arg Leu Asn Asp
    290                 295                 300

Arg Arg Thr Pro Leu Gly Glu Leu Asn Trp Ile Phe Thr Ala Ile Thr
305                 310                 315                 320

Asp Thr Ile Ala Trp Asn Val Leu Pro Arg Asp Leu Phe Gln Lys Leu
                325                 330                 335

Phe Arg Gln Asp Leu Leu Val Ala Ser Leu Phe Arg Asn Phe Leu Leu
            340                 345                 350

Ala Glu Arg Ile Met Arg Ser Tyr Asn Cys Thr Pro Val Ser Ser Pro
        355                 360                 365

Arg Leu Pro Pro Thr Tyr Met His Ala Met Trp Gln Ala Trp Asp Leu
    370                 375                 380

Ala Val Asp Ile Cys Leu Ser Gln Leu Pro Thr Ile Ile Glu Glu Gly
385                 390                 395                 400

Thr Ala Phe Arg His Ser Pro Phe Phe Ala Glu Gln Leu Thr Ala Phe
                405                 410                 415

Gln Val Trp Leu Thr Met Gly Val Glu Asn Arg Asn Pro Pro Glu Gln
            420                 425                 430

Leu Pro Ile Val Leu Gln Val Leu Leu Ser Gln Val His Arg Leu Arg
```

```
                    435                 440                 445
        Ala Leu Asp Leu Leu Gly Arg Phe Leu Asp Leu Gly Pro Trp Ala Val
        450                 455                 460

Ser Leu Ala Leu Ser Val Gly Ile Phe Pro Tyr Val Leu Lys Leu Leu
        465                 470                 475                 480

Gln Ser Ser Ala Arg Glu Leu Arg Pro Leu Leu Val Phe Ile Trp Ala
                        485                 490                 495

Lys Ile Leu Ala Val Asp Ser Ser Cys Gln Ala Asp Leu Val Lys Asp
                        500                 505                 510

Asn Gly His Lys Tyr Phe Leu Ser Val Leu Ala Asp Pro Tyr Met Pro
                        515                 520                 525

Ala Glu His Arg Thr Met Thr Ala Phe Ile Leu Ala Val Ile Val Asn
        530                 535                 540

Ser Tyr His Thr Gly Gln Glu Ala Cys Leu Gln Gly Asn Leu Ile Ala
        545                 550                 555                 560

Ile Cys Leu Glu Gln Leu Asn Asp Pro His Pro Leu Leu Arg Gln Trp
                        565                 570                 575

Val Ala Ile Cys Leu Gly Arg Ile Trp Gln Asn Phe Asp Ser Ala Arg
                        580                 585                 590

Trp Cys Gly Val Arg Asp Ser Ala His Glu Lys Leu Tyr Ser Leu Leu
                        595                 600                 605

Ser Asp Pro Ile Pro Glu Val Arg Cys Ala Ala Val Phe Ala Leu Gly
        610                 615                 620

Thr Phe Val Gly Asn Ser Ala Glu Arg Thr Asp His Ser Thr Thr Ile
        625                 630                 635                 640

Asp His Asn Val Ala Met Met Leu Ala Gln Leu Val Ser Asp Gly Ser
                        645                 650                 655

Pro Met Val Arg Lys Glu Leu Val Val Ala Leu Ser His Leu Val Val
                        660                 665                 670

Gln Tyr Glu Ser Asn Phe Cys Thr Val Ala Leu Gln Phe Ile Glu Glu
                        675                 680                 685

Glu Lys Asn Tyr Ala Leu Pro Ser Pro Ala Thr Thr Glu Gly Gly Ser
                        690                 695                 700

Leu Thr Pro Val Arg Asp Ser Pro Cys Thr Pro Arg Leu Arg Ser Val
        705                 710                 715                 720

Ser Ser Tyr Gly Asn Ile Arg Ala Val Ala Thr Ala Arg Ser Leu Asn
                        725                 730                 735

Lys Ser Leu Gln Asn Leu Ser Leu Thr Glu Glu Ser Gly Gly Ala Val
                        740                 745                 750

Ala Phe Ser Pro Gly Asn Leu Ser Thr Ser Ser Ala Ser Ser Thr
                        755                 760                 765

Leu Gly Ser Pro Glu Asn Glu His Ile Leu Ser Phe Glu Thr Ile
                        770                 775                 780

Asp Lys Met Arg Arg Ala Ser Ser Tyr Ser Ser Leu Asn Ser Leu Ile
        785                 790                 795                 800

Gly Val Ser Phe Asn Ser Val Tyr Thr Gln Ile Trp Arg Val Leu Leu
                        805                 810                 815

His Leu Ala Ala Asp Pro Tyr Pro Glu Val Ser Asp Val Ala Met Lys
                        820                 825                 830

Val Leu Asn Ser Ile Ala Tyr Lys Ala Thr Val Asn Ala Arg Pro Gln
                        835                 840                 845

Arg Val Leu Asp Thr Ser Ser Leu Thr Gln Ser Ala Pro Ala Ser Pro
        850                 855                 860
```

-continued

```
Thr Asn Lys Gly Val His Ile His Gln Ala Gly Gly Ser Pro Pro Ala
865                 870                 875                 880

Ser Ser Thr Ser Ser Ser Ser Leu Thr Asn Asp Val Ala Lys Gln Pro
            885                 890                 895

Val Ser Arg Asp Leu Pro Ser Gly Arg Pro Gly Thr Thr Gly Pro Ala
        900                 905                 910

Gly Ala Gln Tyr Thr Pro His Ser His Gln Phe Pro Arg Thr Arg Lys
            915                 920                 925

Met Phe Asp Lys Gly Pro Glu Gln Thr Ala Asp Ala Asp Asp Ala
930                 935                 940

Ala Gly His Lys Ser Phe Ile Ser Ala Thr Val Gln Thr Gly Phe Cys
945                 950                 955                 960

Asp Trp Ser Ala Arg Tyr Phe Ala Gln Pro Val Met Lys Ile Pro Glu
                965                 970                 975

Glu His Asp Leu Glu Ser Gln Ile Arg Lys Glu Arg Glu Trp Arg Phe
            980                 985                 990

Leu Arg Asn Ser Arg Val Arg Arg Gln Ala Gln Gln Val Ile Gln Lys
        995                 1000                1005

Gly Ile Thr Arg Leu Asp Asp Gln Ile Phe Leu Asn Arg Asn Pro Gly
    1010                1015                1020

Val Pro Ser Val Val Lys Phe His Pro Phe Thr Pro Cys Ile Ala Val
1025                1030                1035                1040

Ala Asp Lys Asp Ser Ile Cys Phe Trp Asp Trp Glu Lys Gly Glu Lys
            1045                1050                1055

Leu Asp Tyr Phe His Asn Gly Asn Pro Arg Tyr Thr Arg Val Thr Ala
        1060                1065                1070

Met Glu Tyr Leu Asn Gly Gln Asp Cys Ser Leu Leu Leu Thr Ala Thr
    1075                1080                1085

Asp Asp Gly Ala Ile Arg Val Trp Lys Asn Phe Ala Asp Leu Glu Lys
    1090                1095                1100

Asn Pro Glu Met Val Thr Ala Trp Gln Gly Leu Ser Asp Met Leu Pro
1105                1110                1115                1120

Thr Thr Arg Gly Ala Gly Met Val Val Asp Trp Glu Gln Glu Thr Gly
            1125                1130                1135

Leu Leu Met Ser Ser Gly Asp Val Arg Ile Val Arg Ile Trp Asp Thr
        1140                1145                1150

Asp Arg Glu Met Lys Val Gln Asp Ile Pro Thr Gly Ala Asp Ser Cys
    1155                1160                1165

Val Thr Ser Leu Ser Cys Asp Ser His Arg Ser Leu Ile Val Ala Gly
    1170                1175                1180

Leu Gly Asp Gly Ser Ile Arg Val Tyr Asp Arg Arg Met Ala Leu Ser
1185                1190                1195                1200

Glu Cys Arg Val Met Thr Tyr Arg Glu His Thr Ala Trp Val Val Lys
        1205                1210                1215

Ala Ser Leu Gln Lys Arg Pro Asp Gly His Ile Val Ser Val Ser Val
    1220                1225                1230

Asn Gly Asp Val Arg Ile Phe Asp Pro Arg Met Pro Glu Ser Val Asn
    1235                1240                1245

Val Leu Gln Ile Val Lys Gly Leu Thr Ala Leu Asp Ile His Pro Gln
    1250                1255                1260

Ala Asp Leu Ile Ala Cys Gly Ser Val Asn Gln Phe Thr Ala Ile Tyr
1265                1270                1275                1280
```

```
Asn Ser Ser Gly Glu Leu Ile Asn Asn Ile Lys Tyr Tyr Asp Gly Phe
                1285                1290                1295

Met Gly Gln Arg Val Gly Ala Ile Ser Cys Leu Ala Phe His Pro His
        1300                1305                1310

Trp Pro His Leu Ala Val Gly Ser Asn Asp Tyr Tyr Ile Ser Val Tyr
        1315                1320                1325

Ser Val Glu Lys Arg Val Arg
        1330            1335

<210> SEQ ID NO 3
<211> LENGTH: 158
<212> TYPE: PRT
<213> ORGANISM: homo sapiens

<400> SEQUENCE: 3

Trp Arg Met Lys Asp Arg Met Lys Thr Val Ser Val Ala Leu Val Leu
 1               5                  10                  15

Cys Leu Asn Val Gly Val Asp Pro Asp Val Val Lys Thr Thr Pro
                20                  25                  30

Cys Ala Arg Leu Glu Cys Trp Ile Asp Pro Leu Ser Met Gly Pro Gln
                35                  40                  45

Lys Ala Leu Glu Thr Ile Gly Ala Asn Leu Gln Lys Gln Tyr Glu Asn
         50                 55                  60

Trp Gln Pro Arg Ala Arg Tyr Lys Gln Ser Leu Asp Pro Thr Val Asp
 65                  70                  75                  80

Glu Val Lys Lys Leu Cys Thr Ser Leu Arg Arg Asn Ala Lys Glu Glu
                 85                  90                  95

Arg Val Leu Phe His Tyr Asn Gly His Gly Val Pro Arg Pro Thr Val
                100                 105                 110

Asn Gly Glu Val Trp Val Phe Asn Lys Asn Tyr Thr Gln Tyr Ile Pro
            115                 120                 125

Leu Ser Ile Tyr Asp Leu Gln Thr Trp Met Gly Ser Pro Ser Ile Phe
        130                 135                 140

Val Tyr Asp Cys Ser Asn Ala Gly Leu Ile Val Lys Ser Phe
145                 150                 155

<210> SEQ ID NO 4
<211> LENGTH: 125
<212> TYPE: PRT
<213> ORGANISM: homo sapiens

<400> SEQUENCE: 4

Cys Ile Gln Leu Ala Ala Cys Glu Ala Thr Glu Leu Leu Pro Met Ile
 1               5                  10                  15

Pro Asp Leu Pro Ala Asp Leu Phe Thr Ser Cys Leu Thr Thr Pro Ile
                20                  25                  30

Ile Pro Gly Arg Leu Asn Asp Arg Arg Thr Pro Leu Gly Glu Leu Asn
                35                  40                  45

Trp Ile Phe Thr Ala Ile Thr Asp Thr Ile Ala Trp Asn Val Leu Pro
         50                 55                  60

Arg Asp Leu Phe Gln Lys Leu Phe Arg Gln Asp Leu Leu Val Ala Ser
 65                  70                  75                  80

Leu Phe Arg Asn Phe Leu Leu Ala Glu Arg Ile Met Arg Ser Tyr Asn
                 85                  90                  95

Cys Thr Pro Val Ser Ser Pro Arg Leu Pro Pro Thr Tyr Met His Ala
                100                 105                 110
```

Met Trp Gln Ala Trp Asp Leu Ala Val Asp Ile Cys Leu
            115                 120                 125

<210> SEQ ID NO 5
<211> LENGTH: 105
<212> TYPE: PRT
<213> ORGANISM: homo sapiens

<400> SEQUENCE: 5

Phe Phe Ala Glu Gln Leu Thr Ala Phe Gln Val Trp Leu Thr Met Gly
  1               5                  10                  15

Val Glu Asn Arg Asn Pro Pro Glu Gln Leu Pro Ile Val Leu Gln Val
             20                  25                  30

Leu Leu Ser Gln Val His Arg Leu Arg Ala Leu Asp Leu Leu Gly Arg
         35                  40                  45

Phe Leu Asp Leu Gly Pro Trp Ala Val Ser Leu Ala Leu Ser Val Gly
     50                  55                  60

Ile Phe Pro Tyr Val Leu Lys Leu Leu Gln Ser Ser Ala Arg Glu Leu
 65                  70                  75                  80

Arg Pro Leu Leu Val Phe Ile Trp Ala Lys Ile Leu Ala Val Asp Ser
                 85                  90                  95

Ser Cys Gln Ala Asp Leu Val Lys Asp
            100                 105

<210> SEQ ID NO 6
<211> LENGTH: 158
<212> TYPE: PRT
<213> ORGANISM: D. melanogaster

<400> SEQUENCE: 6

Trp Arg Ile Arg Glu Arg Met Lys Thr Ala Ser Val Ala Leu Val Leu
  1               5                  10                  15

Cys Leu Asn Ile Gly Val Asp Pro Pro Asp Val Val Lys Ile Gln Pro
             20                  25                  30

Cys Ser Arg Leu Glu Cys Trp Ile Asp Pro Ser Ser Val Ser Pro Pro
         35                  40                  45

Lys Ala Met Glu Leu Ile Gly Ser Asn Leu Gln Met Gln Tyr Glu Arg
     50                  55                  60

Trp Gln Pro Arg Ala Arg Tyr Lys Lys Cys Asn Asp Pro Thr Val Asp
 65                  70                  75                  80

Asp Val Lys Lys Leu Cys Thr Ser Leu Arg Arg Asn Ala Lys Gly Glu
                 85                  90                  95

Arg Ile Leu Phe His Tyr Asn Gly His Gly Val Pro Lys Pro Thr Ala
            100                 105                 110

Asn Gly Glu Ile Trp Val Phe Asn Lys Thr Phe Thr Gln Tyr Ile Pro
            115                 120                 125

Leu Ser Ile Phe Glu Leu Ile Thr Trp Met Ser Ala Pro Ser Ile Tyr
            130                 135                 140

Val Tyr Asp Cys Ser Asn Ala Gly Ile Ile Ile Asn Ser Phe
145                 150                 155

<210> SEQ ID NO 7
<211> LENGTH: 125
<212> TYPE: PRT
<213> ORGANISM: D. melanogaster

<400> SEQUENCE: 7

Cys Ile His Leu Ala Ala Cys Ala Ala Asn Glu Ile Leu Pro Met Asn

```
                1               5                   10                  15
            Ala Gln Leu Pro Ala Asp Leu Phe Thr Ser Cys Leu Thr Thr Pro Ile
                                20                  25                  30

Ile Pro Gly Lys Val Asn Asp Arg Arg Thr Met Met Gly Glu Leu Asn
                        35                  40                  45

Trp Ile Phe Thr Ala Ile Thr Asp Thr Ile Ala Trp Asn Thr Leu Pro
                    50                  55                  60

Arg Glu Leu Phe Gln Arg Leu Phe Arg Gln Asp Leu Leu Val Ala Ser
            65                  70                  75                  80

Leu Phe Arg Asn Phe Leu Leu Ala Glu Arg Ile Leu Arg Ser His Asp
                            85                  90                  95

Cys Thr Pro Val Ser Leu Pro Ala Leu Pro Pro Cys Tyr Arg His Pro
                            100                 105                 110

Met Trp Lys Ala Trp Asp Leu Val Val Asp Leu Ala Leu
                        115                 120                 125

<210> SEQ ID NO 8
<211> LENGTH: 105
<212> TYPE: PRT
<213> ORGANISM: D. Melanogaster

<400> SEQUENCE: 8

Phe Phe Glu His Gln Leu Thr Ala Phe Gln Val Trp Leu Asp Ser Glu
            1               5                   10                  15

Ser Glu Ser Arg Thr Pro Pro Glu Gln Leu Pro Ile Val Leu Gln Val
                            20                  25                  30

Leu Leu Ser Gln Val His Arg Leu Arg Ala Leu Glu Leu Leu Ala Arg
                        35                  40                  45

Phe Leu Asp Leu Gly Pro Trp Ala Val Asn Leu Ala Leu Gly Val Gly
                    50                  55                  60

Ile Phe Pro Tyr Val Leu Lys Leu Leu Gln Ser Ser Thr Arg Glu Leu
            65                  70                  75                  80

Arg Pro Val Leu Val Phe Ile Trp Ala Lys Ile Leu Ala Val Asp Pro
                            85                  90                  95

Ser Cys Gln Val Asp Leu Val Lys Glu
                            100                 105

<210> SEQ ID NO 9
<211> LENGTH: 158
<212> TYPE: PRT
<213> ORGANISM: S. Pombe

<400> SEQUENCE: 9

Trp Arg Met Arg Glu Arg Leu Lys Thr Val Ser Ala Ala Leu Leu Val
            1               5                   10                  15

Cys Leu Asn Ile Gly Val Asp Pro Pro Asp Val Ile Lys Pro Asn Pro
                            20                  25                  30

Ala Ala Lys Tyr Glu Cys Trp Ile Asp Pro Phe Ser Leu Pro Ala Ser
                        35                  40                  45

Lys Ala Leu Glu Ala Ile Gly Lys Asn Leu Gln Gln Gln Tyr Glu Thr
                    50                  55                  60

Leu Ser Met Arg Thr Arg Tyr Arg His Tyr Leu Asp Pro Ala Ile Glu
            65                  70                  75                  80

Glu Val Lys Lys Leu Cys Ile Gly Gln Arg Arg Asn Ala Lys Glu Glu
                            85                  90                  95

Arg Ile Leu Phe His Tyr Asn Gly His Gly Val Pro Met Pro Thr Ala
```

```
                       100                 105                  110

Ser Gly Glu Ile Trp Val Phe Asn Lys Asn Tyr Thr Gln Tyr Ile Pro
            115                 120                 125

Val Ser Leu Tyr Asp Leu Gln Ser Trp Leu Gly Ala Pro Cys Ile Tyr
        130                 135                 140

Val Tyr Asp Cys Ser Ala Ala Gly Asn Ile Ile Val Asn Phe
145                 150                 155

<210> SEQ ID NO 10
<211> LENGTH: 125
<212> TYPE: PRT
<213> ORGANISM: S. Pombe

<400> SEQUENCE: 10

Cys Ile Gln Leu Ala Ala Cys Gly Pro Lys Glu Thr Leu Pro Met Asn
1               5                   10                  15

Pro Asp Leu Pro Ala Asp Leu Phe Thr Ser Cys Leu Thr Ser Pro Ile
            20                  25                  30

Ile Pro Gly Arg Leu Gln Asp Arg Thr Pro Leu Gly Glu Leu Asn
        35                  40                  45

Trp Ile Phe Thr Ala Ile Thr Asp Thr Ile Ala Trp Asn Val Phe Pro
    50                  55                  60

Lys His Leu Phe Arg Arg Leu Phe Arg Gln Asp Leu Met Val Ala Ala
65                  70                  75                  80

Leu Phe Arg Asn Phe Leu Leu Ala Glu Arg Ile Met Leu Val His Ser
                85                  90                  95

Cys His Pro Gln Ser Ser Pro Glu Leu Pro Pro Thr His Asp His Pro
            100                 105                 110

Met Trp Asn Ser Trp Asp Leu Ala Ile Asp Asn Cys Leu
        115                 120                 125

<210> SEQ ID NO 11
<211> LENGTH: 105
<212> TYPE: PRT
<213> ORGANISM: S. Pombe

<400> SEQUENCE: 11

Phe Phe Ser Glu Gln Leu Thr Ala Phe Glu Val Trp Leu Ser Gln Gly
1               5                   10                  15

Leu Ile Ser Arg Lys Pro Pro Asp Gln Leu Pro Leu Val Leu Gln Val
            20                  25                  30

Leu Leu Ser Gln Val His Arg Leu Arg Ala Leu Ile Leu Leu Ser Lys
        35                  40                  45

Phe Leu Asp Leu Gly Val Trp Ala Val Asp Leu Ala Leu Ser Ile Gly
    50                  55                  60

Ile Phe Pro Tyr Val Leu Lys Leu Leu Gln Ser Pro Ala Ile Glu Leu
65                  70                  75                  80

Lys Pro Val Leu Val Phe Ile Trp Ala Arg Ile Leu Ala Val Asp Asp
                85                  90                  95

Ser Cys Gln Ala Asp Leu Leu Lys Asp
            100                 105

<210> SEQ ID NO 12
<211> LENGTH: 160
<212> TYPE: PRT
<213> ORGANISM: S. cerevisiae

<400> SEQUENCE: 12
```

```
Trp Lys Ile Met Lys Asp Arg Gln Lys Thr Val Ser Ala Ala Leu Leu
  1               5                  10                  15

Leu Cys Leu Asn Leu Gly Val Asp Pro Asp Val Met Lys Thr His
             20                  25                  30

Pro Cys Ala Arg Val Glu Ala Trp Val Asp Pro Leu Asn Phe Gln Asp
             35                  40                  45

Ser Lys Lys Ala Ile Glu Gln Ile Gly Lys Asn Leu Gln Ala Gln Tyr
 50                  55                      60

Glu Thr Leu Ser Leu Arg Thr Arg Tyr Lys Gln Ser Leu Asp Pro Cys
 65                  70                  75                  80

Val Glu Asp Val Lys Arg Phe Cys Asn Ser Leu Arg Arg Thr Ser Lys
                 85                  90                  95

Glu Asp Arg Ile Leu Phe His Tyr Asn Gly His Gly Val Pro Lys Pro
                100                 105                 110

Thr Lys Ser Gly Glu Ile Trp Val Phe Asn Arg Gly Tyr Thr Gln Tyr
            115                 120                 125

Ile Pro Val Ser Leu Tyr Asp Leu Gln Thr Trp Leu Gly Ala Pro Cys
            130                 135                 140

Ile Phe Val Tyr Asp Cys Asn Ser Ala Glu Asn Ile Leu Ile Asn Phe
145                 150                 155                 160

<210> SEQ ID NO 13
<211> LENGTH: 126
<212> TYPE: PRT
<213> ORGANISM: S. cerevisiae

<400> SEQUENCE: 13

Cys Phe Gln Leu Ala Ser Cys Thr Ser Asp Glu Leu Leu Met Ser
  1               5                  10                  15

Pro Glu Leu Pro Ala Asp Leu Phe Ser Cys Cys Leu Thr Cys Pro Ile
             20                  25                  30

Ile Pro Gly Met Leu Ser Asp Arg Arg Thr Pro Leu Gly Glu Leu Asn
             35                  40                  45

Trp Ile Phe Thr Ala Ile Thr Asp Thr Ile Ala Trp Thr Ser Leu Pro
 50                  55                      60

Arg Pro Leu Phe Lys Lys Leu Phe Arg His Asp Leu Met Ile Ala Ala
 65                  70                  75                  80

Leu Phe Arg Asn Phe Leu Ala Lys Arg Ile Met Pro Trp Tyr Asn
                 85                  90                  95

Cys His Pro Val Ser Asp Pro Glu Leu Pro Asp Ser Ile Thr Thr His
                100                 105                 110

Pro Met Trp Lys Ser Trp Asp Leu Ala Met Asp Glu Val Leu
            115                 120                 125

<210> SEQ ID NO 14
<211> LENGTH: 106
<212> TYPE: PRT
<213> ORGANISM: S. cerevisiae

<400> SEQUENCE: 14

Phe Phe Glu Gln Asn Leu Thr Ala Phe Glu Leu Trp Leu Lys Tyr Ala
  1               5                  10                  15

Ser Asn Val Arg His Pro Pro Glu Gln Leu Pro Ile Val Leu Gln Val
             20                  25                  30

Leu Leu Ser Gln Val His Arg Ile Arg Ala Leu Val Leu Leu Ser Arg
             35                  40                  45
```

```
Phe Leu Asp Leu Gly Pro Trp Ala Val Tyr Leu Ser Leu Ser Ile Gly
    50                  55                  60

Ile Phe Pro Tyr Val Leu Lys Leu Leu Gln Ser Pro Ala Pro Glu Leu
 65                  70                  75                  80

Lys Pro Ile Leu Val Phe Ile Trp Ala Arg Ile Met Ser Ile Asp Tyr
                 85                  90                  95

Lys Asn Thr Gln Ser Glu Leu Ile Lys Glu
            100                 105

<210> SEQ ID NO 15
<211> LENGTH: 162
<212> TYPE: PRT
<213> ORGANISM: C. elegans

<400> SEQUENCE: 15

Arg Arg Lys Gly Ser Asp Arg Leu Arg Thr Ala Ser Val Ala Ile Ile
 1               5                  10                  15

Met Cys Leu His Leu Gly Val Asp Pro Glu Ala Pro Ser Arg Lys
             20                  25                  30

Asp Ala Pro Ser Arg Leu Leu Ser Trp Val Asp Pro Tyr Lys Cys Gly
            35                  40                  45

Ala His Lys Ala Ala Ile Glu Ile Gly Leu Ser Thr Gln Arg Ala Tyr
     50                  55                  60

Glu Lys Trp Gln Pro Lys Ser Lys Thr Arg Tyr Lys Ile Cys Thr Asp
 65                  70                  75                  80

Pro Pro Ile Asp Asp Val Arg Lys Val Ala Thr Asn Leu Arg Arg Ile
                 85                  90                  95

Ser Gly Asn Asp Arg Val Leu Phe His Tyr Asn Gly His Gly Val Pro
            100                 105                 110

Lys Pro Thr Asp Asn Gly Glu Ile Trp Val Phe Asn Lys Ser Phe Thr
        115                 120                 125

Gln Tyr Ile Pro Leu Ser Ile Phe Asp Leu Gln Gly Trp Leu Asp Tyr
    130                 135                 140

Pro Thr Ile Tyr Ile Trp Glu Thr His Ser Ala Glu Thr Ile Leu His
145                 150                 155                 160

Asn Tyr

<210> SEQ ID NO 16
<211> LENGTH: 126
<212> TYPE: PRT
<213> ORGANISM: C. elegans

<400> SEQUENCE: 16

Cys Ile His Leu Ala Ala Cys Ser Ala Gly Gln Trp Leu Pro Met Ser
 1               5                  10                  15

Asn Pro His Leu Pro Ala Asp Leu Phe Thr Ser Cys Leu Thr Thr Pro
             20                  25                  30

Ile Ile Pro Gly Asn Leu Ala Glu Arg Arg Thr Val Leu Gly Glu Leu
            35                  40                  45

Asn Trp Ile Phe Thr Ala Ile Thr Asp Thr Ile Ala Phe Thr Ser Ile
     50                  55                  60

Asp Arg Asp Ser Phe Gln Lys Leu Phe Arg Gln Asp Leu Leu Leu Ala
 65                  70                  75                  80

Thr Leu Phe Arg Ser Phe Leu Leu Ala Gln Arg Val Met Ser Lys Phe
                 85                  90                  95
```

Asn Val Leu Pro Val Ser Gln Pro Leu Lys Asp Thr Ser Met His
            100                 105                 110

Asp Leu Trp Arg Cys Trp Asp Gln Thr Met Asp Met Val Leu
        115                 120                 125

<210> SEQ ID NO 17
<211> LENGTH: 105
<212> TYPE: PRT
<213> ORGANISM: C. elegans

<400> SEQUENCE: 17

Phe Phe Thr Glu Gln Leu Gln Ala Phe Glu Leu Trp Leu Asp Tyr Gly
 1               5                  10                  15

Val Asp Glu Gly Thr Pro Pro Leu Gln Leu Pro Met Val Leu Gln Val
            20                  25                  30

Leu Leu Ser Gln Ala His Arg Val Arg Ala Leu Arg Leu Leu Ala Arg
        35                  40                  45

Phe Leu Asp Phe Gly Arg Trp Ala Ile Gly Tyr Ser Leu Ala Val Gly
    50                  55                  60

Ile Phe Pro Tyr Val Leu Lys Leu Leu Gln Ser Asn Ile Ser Asp Leu
65                  70                  75                  80

Lys Ile Ser Leu Ala Phe Ile Trp Ala Lys Ile Leu Ala Val Asp Pro
                85                  90                  95

Ser Cys Gln Met Glu Leu Phe Asn Glu
            100                 105

<210> SEQ ID NO 18
<211> LENGTH: 158
<212> TYPE: PRT
<213> ORGANISM: A. thaliana

<400> SEQUENCE: 18

Trp Arg Leu Lys Glu Arg Met Lys Thr Gly Cys Val Ala Leu Val Leu
 1               5                  10                  15

Cys Leu Asn Ile Thr Val Asp Pro Pro Asp Val Ile Lys Ile Ser Pro
            20                  25                  30

Cys Ala Arg Ile Glu Ala Trp Ile Asp Pro Phe Ser Met Ala Pro Pro
        35                  40                  45

Lys Ala Leu Glu Thr Ile Gly Lys Asn Leu Ser Thr Gln Tyr Glu Arg
    50                  55                  60

Trp Gln Pro Arg Ala Arg Tyr Lys Val Gln Leu Asp Pro Thr Val Asp
65                  70                  75                  80

Glu Val Arg Lys Leu Cys Leu Thr Cys Arg Lys Tyr Ala Lys Thr Glu
                85                  90                  95

Arg Val Leu Phe His Tyr Asn Gly His Gly Val Pro Lys Pro Thr Ala
            100                 105                 110

Asn Gly Glu Ile Trp Val Phe Asn Lys Ser Tyr Thr Gln Tyr Ile Pro
        115                 120                 125

Leu Pro Ile Ser Glu Leu Asp Ser Trp Leu Lys Thr Pro Ser Ile Tyr
    130                 135                 140

Val Phe Asp Cys Ser Ala Ala Arg Met Ile Leu Asn Ala Phe
145                 150                 155

<210> SEQ ID NO 19
<211> LENGTH: 125
<212> TYPE: PRT
<213> ORGANISM: A. thaliana

```
<400> SEQUENCE: 19

Cys Ile Leu Leu Ala Ala Cys Asp Val His Glu Thr Leu Pro Gln Ser
  1               5                  10                  15

Val Glu Phe Pro Ala Asp Val Phe Thr Ser Cys Leu Thr Thr Pro Ile
             20                  25                  30

Ile Pro Gly Arg Gln Asn Asp Arg Lys Thr Leu Leu Gly Glu Leu Asn
             35                  40                  45

Trp Ile Phe Thr Ala Val Thr Asp Thr Ile Ala Trp Asn Val Leu Pro
         50                  55                  60

His Glu Leu Phe Gln Arg Leu Phe Arg Gln Asp Leu Leu Val Ala Ser
 65                  70                  75                  80

Leu Phe Arg Asn Phe Leu Leu Ala Glu Arg Ile Met Arg Ser Ala Asn
                 85                  90                  95

Cys Asn Pro Ile Ser His Pro Met Leu Pro Thr His Gln His His
            100                 105                 110

Met Trp Asp Ala Trp Asp Met Ala Ala Glu Ile Cys Leu
            115                 120                 125

<210> SEQ ID NO 20
<211> LENGTH: 105
<212> TYPE: PRT
<213> ORGANISM: A. thaliana

<400> SEQUENCE: 20

Phe Phe Thr Glu Gln Leu Thr Ala Phe Glu Val Trp Leu Asp His Gly
  1               5                  10                  15

Ser Glu His Lys Lys Pro Pro Glu Gln Leu Pro Ile Val Leu Gln Val
             20                  25                  30

Leu Leu Ser Gln Cys His Arg Phe Arg Ala Leu Val Leu Leu Gly Arg
             35                  40                  45

Phe Leu Asp Met Gly Ser Trp Ala Val Asp Leu Ala Leu Ser Val Gly
         50                  55                  60

Ile Phe Pro Tyr Val Leu Lys Leu Leu Gln Thr Thr Thr Asn Glu Leu
 65                  70                  75                  80

Arg Gln Ile Leu Val Phe Ile Trp Thr Lys Ile Leu Ala Leu Asp Lys
                 85                  90                  95

Ser Cys Gln Ile Asp Leu Val Lys Asp
            100                 105

<210> SEQ ID NO 21
<211> LENGTH: 1538
<212> TYPE: PRT
<213> ORGANISM: D. melanogaster

<400> SEQUENCE: 21

Met Thr Ser Ala Val Arg Ala Lys Ser Ala Ala Ala Val Gly Val
  1               5                  10                  15

Ala Val Asp Glu Ser Ser Gly Ser Asn Gly Ser Val Ala Asp Gln
             20                  25                  30

Glu Val Ala Ser Ser Lys Glu Ala Val Leu Ser Val Leu Ile Arg Lys
             35                  40                  45

Arg Tyr Glu Lys Tyr Val Phe Ala Pro Trp Asp Pro Ile Ile Leu
         50                  55                  60

Ile Met Glu Gln Leu Glu His Ile Glu His Cys Arg Ser Ala Ala Leu
 65                  70                  75                  80

Gly Asn Gln Val Ala Ile Gly Arg Asp Pro Ser Gln Asp Ile Arg Asp
```

-continued

```
                85                  90                  95
Asp Arg Cys Pro Leu Ser Leu Gln Thr Lys Arg His Lys Glu Arg Ile
            100                 105                 110

Gln Ala Met Met Tyr Glu Arg Gln Pro Trp Arg Ile Arg Glu Arg Met
            115                 120                 125

Lys Thr Ala Ser Val Ala Leu Val Leu Cys Leu Asn Ile Gly Val Asp
            130                 135                 140

Pro Pro Asp Val Val Lys Ile Gln Pro Cys Ser Arg Leu Glu Cys Trp
145                 150                 155                 160

Ile Asp Pro Ser Val Ser Pro Pro Lys Ala Met Glu Leu Ile Gly
            165                 170                 175

Ser Asn Leu Gln Met Gln Tyr Glu Arg Trp Gln Pro Arg Ala Arg Tyr
            180                 185                 190

Lys Lys Cys Asn Asp Pro Thr Val Asp Asp Val Lys Lys Leu Cys Thr
            195                 200                 205

Ser Leu Arg Arg Asn Ala Lys Gly Glu Arg Ile Leu Phe His Tyr Asn
            210                 215                 220

Gly His Gly Val Pro Lys Pro Thr Ala Asn Gly Glu Ile Trp Val Phe
225                 230                 235                 240

Asn Lys Thr Phe Thr Gln Tyr Ile Pro Leu Ser Ile Phe Glu Leu Ile
            245                 250                 255

Thr Trp Met Ser Ala Pro Ser Ile Tyr Val Tyr Asp Cys Ser Asn Ala
            260                 265                 270

Gly Ile Ile Ile Asn Ser Phe Gln Pro Tyr Ala Lys Gln His Glu Glu
            275                 280                 285

Glu Leu Gly Lys Ala Leu Ala Ala Gln Arg Gly Gly Val Gln
            290                 295                 300

Gln Leu Val Gly Gly Ser Gly Ala Ala Asn Val Ala Ala Asn Gln
305                 310                 315                 320

Val Gln Leu Thr Asn Gln Met Val Ser Tyr Lys Asn Cys Ile His Leu
            325                 330                 335

Ala Ala Cys Ala Ala Asn Glu Ile Leu Pro Met Asn Ala Gln Leu Pro
            340                 345                 350

Ala Asp Leu Phe Thr Ser Cys Leu Thr Thr Pro Ile Asn Ile Ala Leu
            355                 360                 365

Lys Trp Tyr Ala Met Gln Glu Lys Leu Gly Met Val Pro Arg Ile Gln
            370                 375                 380

Ser Glu Leu Ile Asp Lys Ile Pro Gly Lys Val Asn Asp Arg Arg Thr
385                 390                 395                 400

Met Met Gly Glu Leu Asn Trp Ile Phe Thr Ala Ile Thr Asp Thr Ile
            405                 410                 415

Ala Trp Asn Thr Leu Pro Arg Glu Leu Phe Gln Arg Leu Phe Arg Gln
            420                 425                 430

Asp Leu Leu Val Ala Ser Leu Phe Arg Asn Phe Leu Leu Ala Glu Arg
            435                 440                 445

Ile Leu Arg Ser His Asp Cys Thr Pro Val Ser Leu Pro Ala Leu Pro
            450                 455                 460

Pro Cys Tyr Arg His Pro Met Trp Lys Ala Trp Asp Leu Val Val Asp
465                 470                 475                 480

Leu Ala Leu Gln Gln Leu Pro Glu Ile Leu Asp His Asn Ala Pro Tyr
            485                 490                 495

Arg Gln Leu Pro Phe Phe Glu His Gln Leu Thr Ala Phe Gln Val Trp
            500                 505                 510
```

```
Leu Asp Ser Glu Ser Glu Ser Arg Thr Pro Pro Gln Leu Pro Ile
            515                 520                 525

Val Leu Gln Val Leu Leu Ser Gln Val His Arg Leu Arg Ala Leu Glu
530                 535                 540

Leu Leu Ala Arg Phe Leu Asp Leu Gly Pro Trp Ala Val Asn Leu Ala
545                 550                 555                 560

Leu Gly Val Gly Ile Phe Pro Tyr Val Leu Lys Leu Leu Gln Ser Ser
                565                 570                 575

Thr Arg Glu Leu Arg Pro Val Leu Val Phe Ile Trp Ala Lys Ile Leu
            580                 585                 590

Ala Val Asp Pro Ser Cys Gln Val Asp Leu Val Lys Glu Tyr Lys Tyr
            595                 600                 605

Phe Leu Ser Val Leu Gln Asp Thr Ser Val Ser Lys Glu His Arg Thr
            610                 615                 620

Leu Ser Ala Phe Val Leu Ser Ser Ile Val His Asn Phe Leu Leu Gly
625                 630                 635                 640

Gln Thr Ser Ala Leu Gln Gly Pro Leu Leu Ser Ile Cys Leu Glu Gln
                645                 650                 655

Leu Asn Asp Gly Ser Trp Leu Leu Arg Gln Trp Leu Ala Ile Cys Leu
            660                 665                 670

Gly Met Leu Trp Gln Asn Phe Glu Lys Ala Arg Trp Ser Gly Ala Arg
            675                 680                 685

Asp Leu Ala His Glu Lys Leu Tyr Val Leu Arg Asp Ser Ile Pro
            690                 695                 700

Glu Val Arg Ala Ala Val Phe Ala Leu Gly Thr Phe Ile Ser Ser
705                 710                 715                 720

Val Thr Asp Arg Ser Glu Glu Gln Ala Asn Asn Ile Asp Arg Ile Ile
                725                 730                 735

Ala Ile Thr Met Leu Glu Thr Val Gly Glu Asp Met Ser Pro Leu Val
            740                 745                 750

Arg Met Glu Leu Ala Ala Ala Leu Gln Trp Met Val Val Leu Phe Glu
            755                 760                 765

Ser Gln Phe Val Ala Val Tyr Leu Thr Glu His Met Arg Gly His Val
            770                 775                 780

Ser Ala Ala Ser Phe Val Met Cys Pro Asp Pro Arg Asp Leu Thr Ser
785                 790                 795                 800

Ser Thr His Ser Leu Glu Arg His Val Thr Ile Arg Arg Gly Ala Ser
                805                 810                 815

Ser Ser Ser Ile Ser Asn Met Gly Gly Ala Ser Ile Ser Ser Gly Thr
            820                 825                 830

Gly Ser Ser Asn Pro Leu Gly Arg Ser Lys Ser Gly Ser Gly Ser
            835                 840                 845

Ser Gly Gly Arg Gly Ala Ala Gly Ala Ala Gly Gly Thr Asn Ser Ile
850                 855                 860

Pro Phe Gln Ser Ile Phe Thr Lys Leu Trp Leu Gly Ile Cys Asn Leu
865                 870                 875                 880

Ala Gln Asp Pro Phe Pro Arg Val Ala Ala Ile Ala Gln Glu Ile Val
                885                 890                 895

Glu His Val Arg Asp Thr Ala Leu Cys Pro Ile Met Ala Ala Lys Glu
            900                 905                 910

Ala Thr Met Ala Asn Ala Ser Glu Lys Cys Ser Ser Leu Ser Val Ser
            915                 920                 925
```

```
Leu Pro Pro Ser Pro Asn Thr Arg Val Asn Tyr Leu Gly Gly Gly
930                 935                 940

Ala Pro Gly Gly Ala Gly Ala Thr Ala Glu Ser Pro Pro Val Gly Ala
945                 950                 955                 960

Ala Ala Ser Gly Ala Ser His Trp Ala Gln Lys Leu Arg Leu Ser Gly
                965                 970                 975

Ser Gly Ala Cys Met Gly Ala Gly Asp Pro Gln Thr Ile Leu Gln Arg
            980                 985                 990

Lys Leu Arg Thr Ser Ser Ile Asn Asp Glu Thr Asp Ser Gly Pro Gly
        995                 1000                1005

Tyr Ser Arg Gly Val Ala Gly Ala Gly Thr Gly Leu Gly Leu Pro Ser
    1010                1015                1020

Gly Pro Arg Glu Ser Thr His Ser Ala Arg Ser Ser Gly Ser Glu Ser
1025                1030                1035                1040

Asn His Tyr Leu Glu Pro Gly His Ser Leu Thr Pro Ile Val Leu Thr
                1045                1050                1055

Glu Phe Ile Pro Trp Ala Ile Ser Tyr Phe Thr Arg Pro Gly Lys Glu
            1060                1065                1070

Arg Tyr Ser Ser Ala Glu Gly Ser Ala Glu Gly Arg Gln Arg Phe
        1075                1080                1085

Pro Val Asp Arg Asn Ser Ala Glu Leu Arg Arg Arg Leu Arg Phe
    1090                1095                1100

Leu Arg Asn Asp Phe Val Arg Arg His Ala Gly Arg Lys His Gln Glu
1105                1110                1115                1120

Leu Ile Asp Pro Tyr Gly Phe Asp Val Cys Val Trp Asn Arg Lys Thr
                1125                1130                1135

Gln Phe Thr Pro Ser Ile Val Lys Leu Leu Pro Tyr Glu Pro Gln Ile
            1140                1145                1150

Ala Val Ala Tyr Arg Glu Lys Val Leu Val Tyr Asp Phe Gln Tyr Asn
        1155                1160                1165

Ser Val Arg Thr Tyr Gly Ala Glu Ser Leu Gly Gly Asn Phe Thr Gly
    1170                1175                1180

Tyr Ser Ser Gly Tyr Gly Ser Gly Ser Ser Ser Ser Leu Asn
1185                1190                1195                1200

Gly Ser Thr Pro Arg Lys Ser Gly Ala His Thr Ser Gly Gly Gly
                1205                1210                1215

Gly Gly Phe Ser Ala Ala Pro Phe Ala Arg Val Ser Ser Ile Glu Phe
            1220                1225                1230

Ile Asn Ala Gln Asp Met Ala Leu Asn Leu Val Ala His Glu Asp Gly
        1235                1240                1245

Val Val Arg Val Trp Gln Ser Ser Pro Pro Ala Ser Ser Ala Thr Ser
    1250                1255                1260

Glu Asp Thr Pro Ser Lys Ala Arg Leu Val Thr Ala Trp Thr Ala Leu
1265                1270                1275                1280

Gly Gln Val Asn Gln His Asn His Arg Gln Arg Ser Val Ala Ser Gly
                1285                1290                1295

Gly Ser Ile Gly Lys Gly Ala Asp Ala Ser Gly Leu Ser Ser Ala Ala
            1300                1305                1310

Ile Gly Ser Gly Gly Ile Val Thr Ala Trp Gln Gln Cys Ser Gln His
        1315                1320                1325

Leu Val Ile Gly Gly Gly Cys Arg Phe Ile Arg Ile Trp Asp Val
    1330                1335                1340

Glu Arg Glu Leu Lys Leu Ala Asp Ile Pro Leu Gly Arg Ser Glu Thr
```

```
                1345                1350                1355                1360
        Cys Ala Arg Val Leu Ser Pro Tyr Leu Pro Asn Met Arg Ser Asp Val
                        1365                1370                1375

Ile Leu Ala Gly Cys Asp Asp Gly Ser Val Arg Leu Phe Asp Lys Arg
                        1380                1385                1390

Cys Ala Pro Gln Asp Ala Gly Ile Ser Val Tyr Arg Arg His Ser Ala
                        1395                1400                1405

Pro Ile Leu His Ala Ser Leu Arg Ala Asn Gly Leu Val Leu Val Ser
                        1410                1415                1420

Gly Cys Thr Glu Gly Arg Ile Ser Val Ala Asp Met Arg Gly Ser Gln
        1425                1430                1435                1440

Ser Ser Ile Asn Pro Phe Asp Val Val Tyr Glu Trp Asp Ala Gly Gly
                        1445                1450                1455

Asp Val Thr Ala Ile Thr Ser His Gln Leu Glu Asp Thr Val Ala Cys
                        1460                1465                1470

Gly Asn Ala Ser Lys Ile Val Ile Tyr Ser Leu Asp Gly Arg Gln Gln
                        1475                1480                1485

Lys Val Leu Arg Thr Asn Glu Gly Phe Ile Gly Pro Lys Ile Gly His
                        1490                1495                1500

Pro Thr Tyr Leu Tyr Phe His Pro Tyr Lys Ala Gln Leu Ala Val Gly
        1505                1510                1515                1520

Phe Val Asp Asn Thr Val Ala Ile Glu Tyr Ser Pro Thr Pro Gly Arg Glu
                        1525                1530                1535

Gln Ser

<210> SEQ ID NO 22
<211> LENGTH: 1313
<212> TYPE: PRT
<213> ORGANISM: S. pombe

<400> SEQUENCE: 22

Met Asn Asp Arg Ile Ser Glu Val Ser Gly Ser Ser Arg Ala Arg Arg
         1               5                  10                  15

Ser Val Leu Ser Tyr Gly Thr Thr Glu Thr Gly Ser Asp Arg Tyr Thr
                        20                  25                  30

Glu Asn Ser Asn Ile Ala Thr Glu Asn Gly Val Asp Thr Ala Ser Ser
                        35                  40                  45

Met Ile Asp Gly Ile Gln Ser Gly Phe Pro Gln Pro Arg His Gly Phe
                50                  55                  60

Glu Glu Glu Tyr Asn Asn Ala Glu Tyr Ile Asn Met Leu Glu Gln Val
        65                  70                  75                  80

Phe Tyr Met Tyr Tyr Thr Asp Lys Arg His Arg Gly Val Ile Ser Lys
                        85                  90                  95

Lys Asn Ala Glu Pro Thr Glu Thr Ile His Asp Trp Arg Met Arg Glu
                        100                 105                 110

Arg Leu Lys Thr Val Ser Ala Ala Leu Leu Val Cys Leu Asn Ile Gly
                        115                 120                 125

Val Asp Pro Pro Asp Val Ile Lys Pro Asn Pro Ala Ala Lys Tyr Glu
                130                 135                 140

Cys Trp Ile Asp Pro Phe Ser Leu Pro Ala Ser Lys Ala Leu Glu Ala
        145                 150                 155                 160

Ile Gly Lys Asn Leu Gln Gln Gln Tyr Glu Thr Leu Ser Met Arg Thr
                        165                 170                 175

Arg Tyr Arg His Tyr Leu Asp Pro Ala Ile Glu Glu Val Lys Lys Leu
```

-continued

```
            180                 185                 190
Cys Ile Gly Gln Arg Arg Asn Ala Lys Glu Glu Arg Ile Leu Phe His
            195                 200                 205
Tyr Asn Gly His Gly Val Pro Met Pro Thr Ala Ser Gly Glu Ile Trp
        210                 215                 220
Val Phe Asn Lys Asn Tyr Thr Gln Tyr Ile Pro Val Ser Leu Tyr Asp
225                 230                 235                 240
Leu Gln Ser Trp Leu Gly Ala Pro Cys Ile Tyr Val Tyr Asp Cys Ser
                245                 250                 255
Ala Ala Gly Asn Ile Ile Val Asn Phe Asn Arg Phe Ala Glu Gln Arg
            260                 265                 270
Asp Lys Glu Ala Leu Arg Ile Ala Lys Gln Asn Pro Asn Val Leu Ala
        275                 280                 285
Met Pro Ser His Thr Ser Cys Ile Gln Leu Ala Ala Cys Gly Pro Lys
290                 295                 300
Glu Thr Leu Pro Met Asn Pro Asp Leu Pro Ala Asp Leu Phe Thr Ser
305                 310                 315                 320
Cys Leu Thr Ser Pro Ile Glu Ile Ser Val Arg Trp Tyr Val Leu Gln
                325                 330                 335
Asn Pro Phe Pro Asn Lys Leu Asn Leu Asn Met Leu Leu Lys Ile Pro
            340                 345                 350
Gly Arg Leu Gln Asp Arg Arg Thr Pro Leu Gly Glu Leu Asn Trp Ile
        355                 360                 365
Phe Thr Ala Ile Thr Asp Thr Ile Ala Trp Asn Val Phe Pro Lys His
        370                 375                 380
Leu Phe Arg Arg Leu Phe Arg Gln Asp Leu Met Val Ala Ala Leu Phe
385                 390                 395                 400
Arg Asn Phe Leu Leu Ala Glu Arg Ile Met Leu Val His Ser Cys His
                405                 410                 415
Pro Gln Ser Ser Pro Glu Leu Pro Pro Thr His Asp His Pro Met Trp
            420                 425                 430
Asn Ser Trp Asp Leu Ala Ile Asp Asn Cys Leu Ser Gln Leu Pro Asp
        435                 440                 445
Met Leu Asp Ala Glu Ser Lys Gly Ile Ala Tyr Glu Tyr Lys His Ser
        450                 455                 460
Thr Phe Phe Ser Glu Gln Leu Thr Ala Phe Glu Val Trp Leu Ser Gln
465                 470                 475                 480
Gly Leu Ile Ser Arg Lys Pro Pro Asp Gln Leu Pro Leu Val Leu Gln
                485                 490                 495
Val Leu Leu Ser Gln Val His Arg Leu Arg Ala Leu Ile Leu Leu Ser
            500                 505                 510
Lys Phe Leu Asp Leu Gly Val Trp Ala Val Asp Leu Ala Leu Ser Ile
        515                 520                 525
Gly Ile Phe Pro Tyr Val Leu Lys Leu Gln Ser Pro Ala Ile Glu
        530                 535                 540
Leu Lys Pro Val Leu Val Phe Ile Trp Ala Arg Ile Leu Ala Val Asp
545                 550                 555                 560
Asp Ser Cys Gln Ala Asp Leu Leu Lys Asp Asn Gly Tyr Gly Tyr Phe
                565                 570                 575
Val Gln Ile Leu Asn Pro Asn Ser Ser Ile Phe Pro Ser Ser Asn Ile
            580                 585                 590
Ser Glu His Arg Ala Met Cys Ala Phe Ile Leu Ser Val Phe Cys Arg
        595                 600                 605
```

```
Gly Phe Pro Gln Gly Gln Leu Ala Cys Leu Asn Pro Gln Val Leu Ser
    610                 615                 620

His Cys Leu Ser His Leu Asn Ser Pro Asp Ser Leu Leu Arg Gln Trp
625                 630                 635                 640

Ala Cys Leu Cys Ile Ser Gln Leu Trp Glu Asn Tyr Ser Glu Ala Lys
                645                 650                 655

Trp Ser Gly Thr Arg Asp Asn Ala His Val Lys Leu Ala Glu Ile Ile
                660                 665                 670

Val Asp Ser Val Pro Glu Val Arg Ala Ser Val Leu Thr Ala Phe Thr
            675                 680                 685

Thr Phe Leu Gly Phe Pro Glu Lys Thr Glu Val Val Ala Val Glu
690                 695                 700

Thr Tyr Ile Ala Ile Ala Ala Leu Ala Ala Leu Ser Asp Ala Ser Pro
705                 710                 715                 720

Leu Val Arg His Glu Leu Val Ile Phe Leu Ser His Phe Val Asn
                725                 730                 735

Tyr Lys Lys Gln Leu Met Val Val Ala Tyr Glu Ser Ser Leu Ala Asp
                740                 745                 750

Ile Leu Glu Lys Lys Asn His Asn Ser Ile Ser Ala Ser Thr Ile Tyr
            755                 760                 765

Glu Thr Val Trp Gln Ala Val Leu Val Leu Ala Ala Asp Pro Ser Ile
770                 775                 780

Glu Ile Ser Leu Ala Ala Glu Ala Ile Ile Asn Tyr Val Tyr Gln Ser
785                 790                 795                 800

Met Leu Asn Ser Glu Leu Arg Glu Ser Phe Leu Ala Phe Leu Leu Gln
                805                 810                 815

His Leu Pro Ala Leu His Lys Ala Ser Leu Ser Lys Asp Thr Asp Thr
            820                 825                 830

Asn Ser Val Thr Ser Asp Pro Lys Pro His Pro Phe Val Pro Ser Val
            835                 840                 845

Ser Glu Asn Lys Ile Leu Asn Arg Ser Phe Ser Leu Thr Arg Ser Leu
850                 855                 860

Lys Gly Leu Ala Leu Ser Leu Ala Gly Ser Asp Arg Ala Ser Glu Leu
865                 870                 875                 880

Leu Ser Leu Asn Gly Glu Asn Lys Pro Ala Glu Ser Asn Leu Asn His
                885                 890                 895

Leu Thr Ser Ala Lys Val Pro Gly Pro Pro Ala Phe Asn Glu Leu Glu
            900                 905                 910

Tyr Gln Ser Glu Leu Asp Met Pro Leu Thr Ser Tyr Leu Phe Asp Trp
            915                 920                 925

Ser Arg Lys Tyr Phe Thr Glu Pro Gln Met Arg Pro Asn Glu Asp Asp
930                 935                 940

Glu Pro Gly Ser Ile Cys Tyr Asn Gln Arg Leu Trp Arg Arg Asn Arg
945                 950                 955                 960

Asn Glu Lys Leu Ile Tyr Arg Thr Arg Pro Leu Ala Glu Tyr Ser Thr
                965                 970                 975

Asn Gly Arg Trp Asn Gln Gln Leu Met Thr Phe Asn Asn Thr Ile Ala
            980                 985                 990

Pro Arg Lys Leu Met Phe His Gln Phe Glu Asp Gln Leu Ile Thr Leu
        995                 1000                1005

Gly Asp Lys Asp Ile Ile Gln Val Trp Asp Trp Arg Arg Asn Arg Cys
    1010                1015                1020
```

Leu Asn Ser Phe Lys Thr Ser Ala Ser Ala Thr Thr Asn Val Thr Asp
1025                1030                1035                1040

Met Gln Leu Leu Asn Glu Asp Val Ala Leu Leu Met Thr Gly Ser
        1045                1050                1055

Ser Asp Gly Thr Ile Lys Leu Tyr Arg Asp Tyr Glu Asn Glu Lys Val
            1060                1065                1070

Glu Leu Val Thr Ser Trp Asn Ser Leu Ser Asp Leu Val Phe Gly Asp
        1075                1080                1085

Arg Asn Ala Ser Leu Leu Met Ser Trp Gln Gln Asn Cys Gly His Leu
        1090                1095                1100

Leu Val Ala Gly Asp Val Arg Val Ile Arg Ile Trp Asp Ala Ser Lys
1105                1110                1115                1120

Glu Ile Cys Tyr Ala Asn Leu Pro Val Arg Ser Ser Asn Ser Ile Thr
            1125                1130                1135

Ser Leu Thr Ser Asp Leu Val Gly Cys Asn Ile Ile Val Ala Gly Phe
        1140                1145                1150

Ser Asp Gly Val Leu Arg Val Tyr Asp Lys Arg Leu Pro Ala Arg Asp
        1155                1160                1165

Ser Leu Thr Asp Val Trp Lys Glu His Ser Ser Glu Ile Val Asn Val
    1170                1175                1180

Glu Met Gln Ser Ser Gly Met Arg Glu Leu Ile Ser Ala Ser Ser Asp
1185                1190                1195                1200

Gly Glu Val Lys Leu Trp Asp Ile Arg Met Asn His Ser Leu Gln Thr
            1205                1210                1215

Phe Ser Thr Asp Asn Ser Gly Leu Thr Ser Leu Thr Val His Ser His
        1220                1225                1230

Ala Pro Val Tyr Ala Thr Gly Ser Ser Asn Gln Ser Ile Lys Ile Trp
        1235                1240                1245

Asp Thr Leu Gly Gln Asn Ile Asn Thr Phe Arg Glu Asn Pro Arg Phe
    1250                1255                1260

Leu Asn Gln Pro Lys Pro Ser Leu Met Cys Leu Lys Phe His Pro
1265                1270                1275                1280

His His Leu Leu Leu Ala Cys Gly Asp Asn Thr Asp Ser Arg Val Asn
            1285                1290                1295

Leu Tyr Ser Cys Thr Lys Asn Glu Ile His Thr Asp Ser Pro Asn Glu
        1300                1305                1310

Phe

<210> SEQ ID NO 23
<211> LENGTH: 1527
<212> TYPE: PRT
<213> ORGANISM: S. cerevisiae

<400> SEQUENCE: 23

Met Arg His Gly Phe Glu Glu Gln Tyr Gln Ser Asp Gln Leu Leu Gln
1               5                   10                  15

Ser Leu Ala Asn Asp Phe Ile Phe Tyr Phe Asp Asp Lys Arg His Lys
            20                  25                  30

Thr Asn Gly Asn Pro Ile Pro Glu Glu Asp Lys Gln Arg Asp Val Asn
        35                  40                  45

Arg Tyr Tyr Gln Pro Ile Thr Asp Trp Lys Ile Met Lys Asp Arg Gln
    50                  55                  60

Lys Thr Val Ser Ala Ala Leu Leu Leu Cys Leu Asn Leu Gly Val Asp
65                  70                  75                  80

```
Pro Pro Asp Val Met Lys Thr His Pro Cys Ala Arg Val Glu Ala Trp
                85                  90                  95

Val Asp Pro Leu Asn Phe Gln Asp Ser Lys Lys Ala Ile Glu Gln Ile
            100                 105                 110

Gly Lys Asn Leu Gln Ala Gln Tyr Glu Thr Leu Ser Leu Arg Thr Arg
            115                 120                 125

Tyr Lys Gln Ser Leu Asp Pro Cys Val Glu Asp Val Lys Arg Phe Cys
130                 135                 140

Asn Ser Leu Arg Arg Thr Ser Lys Glu Asp Arg Ile Leu Phe His Tyr
145                 150                 155                 160

Asn Gly His Gly Val Pro Lys Pro Thr Lys Ser Gly Glu Ile Trp Val
                165                 170                 175

Phe Asn Arg Gly Tyr Thr Gln Tyr Ile Pro Val Ser Leu Tyr Asp Leu
            180                 185                 190

Gln Thr Trp Leu Gly Ala Pro Cys Ile Phe Val Tyr Asp Cys Asn Ser
            195                 200                 205

Ala Glu Asn Ile Leu Ile Asn Phe Gln Lys Phe Val Gln Lys Arg Ile
            210                 215                 220

Lys Asp Asp Glu Glu Gly Asn His Asp Val Ala Ala Pro Ser Pro Thr
225                 230                 235                 240

Ser Ala Tyr Gln Asp Cys Phe Gln Leu Ala Ser Cys Thr Ser Asp Glu
                245                 250                 255

Leu Leu Leu Met Ser Pro Glu Leu Pro Ala Asp Leu Phe Ser Cys Cys
            260                 265                 270

Leu Thr Cys Pro Ile Glu Ile Ser Ile Arg Ile Phe Leu Met Gln Ser
            275                 280                 285

Pro Leu Lys Asp Ser Lys Tyr Lys Ile Phe Phe Glu Phe Lys Ser Lys
290                 295                 300

Ile Pro Asn Val Asn Ile Pro Gly Met Leu Ser Asp Arg Arg Thr Pro
305                 310                 315                 320

Leu Gly Glu Leu Asn Trp Ile Phe Thr Ala Ile Thr Asp Thr Ile Ala
            325                 330                 335

Trp Thr Ser Leu Pro Arg Pro Leu Phe Lys Lys Leu Phe Arg His Asp
            340                 345                 350

Leu Met Ile Ala Ala Leu Phe Arg Asn Phe Leu Leu Ala Lys Arg Ile
            355                 360                 365

Met Pro Trp Tyr Asn Cys His Pro Val Ser Asp Pro Glu Leu Pro Asp
            370                 375                 380

Ser Ile Thr Thr His Pro Met Trp Lys Ser Trp Asp Leu Ala Met Asp
385                 390                 395                 400

Glu Val Leu Thr Lys Ile Val Ile Asp Leu Lys Asn Ala Pro Pro Ala
                405                 410                 415

Thr Ala Leu Glu Ser Gln Met Ile Leu Gln Gln Glu Thr Leu Gln
            420                 425                 430

Asn Gly Gly Ser Ser Lys Ser Asn Ala Gln Asp Thr Lys Ala Gly Ser
            435                 440                 445

Ile Gln Thr Gln Ser Arg Phe Ala Val Ala Asn Leu Ser Thr Met Ser
            450                 455                 460

Leu Val Asn Asn Pro Ala Leu Gln Ser Arg Lys Ser Ile Ser Leu Gln
465                 470                 475                 480

Ser Ser Gln Gln Gln Leu Gln Gln Gln Gln Gln Gln Gln Gln Gln Phe
                485                 490                 495

Thr Gly Phe Phe Glu Gln Asn Leu Thr Ala Phe Glu Leu Trp Leu Lys
```

```
                500                 505                 510
Tyr Ala Ser Asn Val Arg His Pro Pro Glu Gln Leu Pro Ile Val Leu
            515                 520                 525

Gln Val Leu Leu Ser Gln Val His Arg Ile Arg Ala Leu Val Leu Leu
        530                 535                 540

Ser Arg Phe Leu Asp Leu Gly Pro Trp Ala Val Tyr Leu Ser Leu Ser
545                 550                 555                 560

Ile Gly Ile Phe Pro Tyr Val Leu Lys Leu Leu Gln Ser Pro Ala Pro
            565                 570                 575

Glu Leu Lys Pro Ile Leu Val Phe Ile Trp Ala Arg Ile Met Ser Ile
        580                 585                 590

Asp Tyr Lys Asn Thr Gln Ser Glu Leu Ile Lys Glu Lys Gly Tyr Met
            595                 600                 605

Tyr Phe Val Thr Val Leu Val Pro Asp Trp Gly Val Asn Gly Met Ser
        610                 615                 620

Ala Thr Asn Gly Ser Ala Met Ile Asn Ser Gly Asn Pro Leu Thr Met
625                 630                 635                 640

Thr Ala Ser Gln Asn Ile Asn Gly Pro Ser Ser Arg Tyr Tyr Glu Arg
            645                 650                 655

Gln Gln Gly Asn Arg Thr Ser Asn Leu Gly His Asn Asn Leu Pro Phe
        660                 665                 670

Tyr His Ser Asn Asp Thr Thr Asp Glu Gln Lys Ala Met Ala Val Phe
            675                 680                 685

Val Leu Ala Ser Phe Val Arg Asn Phe Pro Leu Gly Gln Lys Asn Cys
        690                 695                 700

Phe Ser Leu Glu Leu Val Asn Lys Leu Cys Phe Tyr Ile Asp Asn Ser
705                 710                 715                 720

Glu Ile Pro Leu Leu Arg Gln Trp Cys Val Ile Leu Gly Leu Leu
            725                 730                 735

Phe Ala Asp Asn Pro Leu Asn Arg Phe Val Cys Met Asn Thr Gly Ala
            740                 745                 750

Val Glu Ile Leu Leu Lys Ser Leu Lys Asp Pro Val Pro Glu Val Arg
        755                 760                 765

Thr Ala Ser Ile Phe Ala Leu Lys His Phe Ile Ser Gly Phe Gln Asp
        770                 775                 780

Ala Glu Val Ile Leu Arg Leu Gln Gln Glu Phe Glu Glu Gln Tyr Gln
785                 790                 795                 800

Gln Leu His Ser Gln Leu Gln His Leu Gln Asn Gln Ser His Leu Gln
            805                 810                 815

Gln Gln Gln Ser Gln Gln Gln Gln His Leu Glu Gln Gln Gln Met
        820                 825                 830

Lys Ile Glu Lys Gln Ile Arg His Cys Gln Val Met Gln Asn Gln Leu
            835                 840                 845

Glu Val Ile Asp Leu Arg Lys Leu Lys Arg Gln Glu Ile Gly Asn Leu
        850                 855                 860

Ile Ser Ile Leu Pro Leu Ile Asn Asp Gly Ser Ser Leu Val Arg Lys
865                 870                 875                 880

Glu Leu Val Val Tyr Phe Ser His Ile Val Ser Arg Tyr Ser Asn Phe
            885                 890                 895

Phe Ile Val Val Val Phe Asn Asp Leu Leu Glu Glu Ile Lys Leu Leu
        900                 905                 910

Glu Lys Ser Asp Ile Asn Thr Arg Asn Thr Ser Asp Lys Tyr Ser Val
            915                 920                 925
```

```
Ser Gln Gly Ser Ile Phe Tyr Thr Val Trp Lys Ser Leu Ile Leu
        930                 935                 940

Ala Glu Asp Pro Phe Leu Glu Asn Lys Glu Leu Ser Lys Gln Val Ile
945                 950                 955                 960

Asp Tyr Ile Leu Leu Glu Leu Ser Ala His Lys Glu Leu Gly Gly Pro
                965                 970                 975

Phe Ala Val Met Glu Lys Phe Leu Leu Lys Arg Ser Ser Lys Ala His
                980                 985                 990

Gln Thr Gly Lys Phe Gly Phe Asn Ser Ser Gln Val Gln Phe Val Lys
                995                 1000                1005

Ser Ser Leu Arg Ser Phe Ser Pro Asn Glu Arg Val Asp Asn Asn Ala
        1010                1015                1020

Phe Lys Lys Glu Gln Gln Gln His Asp Pro Lys Ile Ser His Pro Met
1025                1030                1035                1040

Arg Thr Ser Leu Ala Lys Leu Phe Gln Ser Leu Gly Phe Ser Glu Ser
                1045                1050                1055

Asn Ser Asp Ser Asp Thr Gln Ser Ser Asn Thr Ser Met Lys Ser His
                1060                1065                1070

Thr Ser Lys Lys Gly Pro Ser Gly Leu Tyr Leu Leu Asn Gly Asn Asn
        1075                1080                1085

Asn Ile Tyr Pro Thr Ala Glu Thr Pro Arg Phe Arg Lys His Thr Glu
        1090                1095                1100

Pro Leu Gln Leu Pro Leu Asn Ser Ser Phe Leu Asp Tyr Ser Arg Glu
1105                1110                1115                1120

Tyr Phe Gln Glu Pro Gln Met Lys Lys Gln Glu Ala Asp Glu Pro Gly
                1125                1130                1135

Ser Val Glu Tyr Asn Ala Arg Leu Trp Arg Arg Asn Arg Asn Glu Thr
                1140                1145                1150

Ile Ile Gln Glu Thr Gln Gly Glu Lys Lys Leu Ser Ile Tyr Gly Asn
        1155                1160                1165

Trp Ser Lys Lys Leu Ile Ser Leu Asn Asn Lys Ser Gln Pro Lys Leu
        1170                1175                1180

Met Lys Phe Ala Gln Phe Glu Asp Gln Leu Ile Thr Ala Asp Asp Arg
1185                1190                1195                1200

Ser Thr Ile Thr Val Phe Asp Trp Glu Lys Gly Lys Thr Leu Ser Lys
                1205                1210                1215

Phe Ser Asn Gly Thr Pro Phe Gly Thr Lys Val Thr Asp Leu Lys Leu
                1220                1225                1230

Ile Asn Glu Asp Asp Ser Ala Leu Leu Leu Thr Gly Ser Ser Asp Gly
        1235                1240                1245

Val Ile Lys Ile Tyr Arg Asp Tyr Gln Asp Val Asp Thr Phe Lys Ile
        1250                1255                1260

Val Ser Ala Trp Arg Gly Leu Thr Asp Met Leu Leu Thr Pro Arg Ser
1265                1270                1275                1280

Thr Gly Leu Leu Thr Glu Trp Leu Gln Ile Arg Gly Ser Leu Leu Thr
                1285                1290                1295

Thr Gly Asp Val Lys Val Ile Arg Val Trp Asp Ala His Thr Glu Thr
                1300                1305                1310

Val Glu Val Asp Ile Pro Ala Lys Thr Ser Ser Leu Ile Thr Ser Leu
        1315                1320                1325

Thr Ala Asp Gln Leu Ala Gly Asn Ile Phe Val Ala Gly Phe Ala Asp
        1330                1335                1340
```

Gly Ser Leu Arg Val Tyr Asp Arg Arg Leu Asp Pro Arg Asp Ser Met
1345                1350                1355                1360

Ile Arg Arg Trp Arg Ala Gly Asn Asp Lys Gln Gly Val Trp Ile Asn
            1365                1370                1375

Asn Val His Leu Gln Arg Gly Gly Tyr Arg Glu Leu Val Ser Gly Ala
            1380                1385                1390

Thr Asn Gly Val Val Glu Leu Trp Asp Ile Arg Ser Glu Asp Pro Val
            1395                1400                1405

Glu Ser Phe Val Asp Gln Asn Val Thr Ser Gln Tyr Gly Ser Gln Gln
            1410                1415                1420

Lys Pro Thr Thr Met Thr Cys Met Gln Val His Glu His Ala Pro Ile
1425                1430                1435                1440

Ile Ala Thr Gly Thr Lys Gln Ile Lys Ile Trp Thr Thr Ser Gly Asp
            1445                1450                1455

Leu Leu Asn Ser Phe Lys Asn Ser His Asn Asn Gly Val Thr Ser Thr
            1460                1465                1470

Leu Ala Ala Thr Gly Ile Pro Lys Ser Leu Ser Tyr Ser Ser Thr Ser
            1475                1480                1485

Asp Ala Phe Leu Ser Ser Met Ala Phe His Pro His Arg Met Met Ile
            1490                1495                1500

Ala Ala Thr Asn Ser His Asp Ser Ile Val Asn Ile Tyr Lys Cys Glu
1505                1510                1515                1520

Asp Glu Arg Ile Asp Tyr Phe
            1525

<210> SEQ ID NO 24
<211> LENGTH: 1683
<212> TYPE: PRT
<213> ORGANISM: C. elegans

<400> SEQUENCE: 24

Glu Cys Val Asn Arg Arg Lys Gly Ser Asp Arg Leu Arg Thr Ala Ser
 1               5                  10                  15

Val Ala Ile Ile Met Cys Leu His Leu Gly Val Asp Pro Pro Glu Ala
            20                  25                  30

Pro Ser Arg Lys Asp Ala Pro Ser Arg Leu Leu Ser Trp Val Asp Pro
        35                  40                  45

Tyr Lys Cys Gly Ala His Lys Ala Ala Ile Glu Ile Gly Leu Ser Thr
    50                  55                  60

Gln Arg Ala Tyr Glu Lys Trp Gln Pro Lys Ser Lys Thr Arg Tyr Lys
65                  70                  75                  80

Ile Cys Thr Asp Pro Pro Ile Asp Asp Val Arg Lys Val Ala Thr Asn
                85                  90                  95

Leu Arg Arg Ile Ser Gly Asn Asp Arg Val Leu Phe His Tyr Asn Gly
            100                 105                 110

His Gly Val Pro Lys Pro Thr Asp Asn Gly Glu Ile Trp Val Phe Asn
        115                 120                 125

Lys Ser Phe Thr Gln Tyr Ile Pro Leu Ser Ile Phe Asp Leu Gln Gly
    130                 135                 140

Trp Leu Asp Tyr Pro Thr Ile Tyr Ile Trp Glu Thr Ser Ala Glu
145                 150                 155                 160

Thr Ile Leu His Asn Tyr Arg Arg Phe Gly Glu Asp Gln Lys Ile Ser
                165                 170                 175

Trp Gln Ser Arg Phe Asp Arg Trp Gln Glu Glu Gln Arg Asn Leu Pro
            180                 185                 190

```
Pro Ile Ser Ser Lys Met Thr Asp Ala Asp Gln Ala Glu Ala Leu Gly
    195                 200                 205

Phe Pro Glu Lys Tyr Pro Arg Tyr Asn Asp Cys Ile His Leu Ala Ala
    210                 215                 220

Cys Ser Ala Gly Gln Trp Leu Pro Met Ser Asn Pro His Leu Pro Ala
225                 230                 235                 240

Asp Leu Phe Thr Ser Cys Leu Thr Thr Pro Ile Arg Thr Ser Leu Ala
                245                 250                 255

Phe His Leu Ser His Ser Glu His Arg Asp Glu Tyr Pro Glu Asn Ile
            260                 265                 270

Leu Asp Met Ile Pro Gly Asn Leu Ala Glu Arg Arg Thr Val Leu Gly
        275                 280                 285

Glu Leu Asn Trp Ile Phe Thr Ala Ile Thr Asp Thr Ile Ala Phe Thr
    290                 295                 300

Ser Ile Asp Arg Asp Ser Phe Gln Lys Leu Phe Arg Gln Asp Leu Leu
305                 310                 315                 320

Leu Ala Thr Leu Phe Arg Ser Phe Leu Leu Ala Gln Arg Val Met Ser
                325                 330                 335

Lys Phe Asn Val Leu Pro Val Ser Gln Pro Pro Leu Lys Asp Thr Ser
            340                 345                 350

Met His Asp Leu Trp Arg Cys Trp Asp Gln Thr Met Asp Met Val Leu
        355                 360                 365

Asp Tyr Cys Arg Glu Leu Ile Tyr Val Lys Glu Cys Glu Arg Ala Leu
    370                 375                 380

Phe Cys Gly Arg Asp Val Ile Asn Arg Ser Asn Val Phe Pro Phe Leu
385                 390                 395                 400

Val Leu Ile Asp Phe Glu His Val Leu Thr Tyr Asn Glu Thr His Gln
                405                 410                 415

Tyr Asn Thr Phe Phe Thr Glu Gln Leu Gln Ala Phe Glu Leu Trp Leu
            420                 425                 430

Asp Tyr Gly Val Asp Glu Gly Thr Pro Pro Leu Gln Leu Pro Met Val
        435                 440                 445

Leu Gln Val Leu Ser Gln Ala His Arg Val Arg Ala Leu Arg Leu
    450                 455                 460

Leu Ala Arg Phe Leu Asp Phe Gly Arg Trp Ala Ile Gly Tyr Ser Leu
465                 470                 475                 480

Ala Val Gly Ile Phe Pro Tyr Val Leu Lys Leu Leu Gln Ser Asn Ile
                485                 490                 495

Ser Asp Leu Lys Ile Ser Leu Ala Phe Ile Trp Ala Lys Ile Leu Ala
            500                 505                 510

Val Asp Pro Ser Cys Gln Met Glu Leu Phe Asn Glu Cys Ile Asp Glu
        515                 520                 525

Ser Ala Thr Gln Gln Gln Ser Pro Ala Gln Ser Gln Pro Ser Val
    530                 535                 540

Ala Leu Lys Pro Ser Ser Met Phe Ala Asn His Pro Pro Ala Gln
545                 550                 555                 560

Leu Thr Met Asp Lys Arg Ala Leu Gln Ile Asn Thr Gln Thr Gly Gly
                565                 570                 575

Arg Phe Gln Thr Asn Gln Asn Gln Ala Leu Asp Met Gln Leu Gln Tyr
            580                 585                 590

Ala Gln Gln Gln Ala His Gln Arg Gln Met Asp Pro Ser Gly Gly Gln
        595                 600                 605
```

-continued

His Ser Pro Asn Ala Gln Pro Arg Gln Pro Gln Pro Gln
610             615             620

Gln Leu Gln Gln Gln Pro Ser Gln Gln Gln Gln Ser Arg Gln
625             630             635             640

Pro Gln Gly Ile Met Lys Pro Thr Asn Ala Gln Pro Glu Lys Lys
            645             650             655

Thr Met Leu Arg Phe Gln Tyr Phe Leu Gln Leu Leu Gly Asp Pro Glu
            660             665             670

Ile Lys Pro Lys Gln Lys Thr Val Ala Phe Val Leu Ala Gln Leu
            675             680             685

Thr Ser Asn Asn Phe Lys Leu Ala Gln Lys Glu Leu Thr Asn Lys Gly
690             695             700

Tyr Met Gly Ile Cys Thr Glu Leu Met Val Asp Asp Thr Ala Arg Ser
705             710             715             720

Val Lys Leu Leu Lys Leu Trp Ile Leu Ile Gly Leu Gly Arg Leu Trp
            725             730             735

Ser Asp Tyr Asp Val Ala Arg Trp Gln Gly Ile Arg Leu Met Ala His
            740             745             750

Asp Lys Met Ile Leu Glu Leu Ser Asp Glu Ser Ala Glu Val Arg Ala
            755             760             765

Ala Ala Val Phe Ala Leu Gly Ser Leu Leu Arg Asn Ser Ser Arg Ser
770             775             780

Asn Glu His Ala Ser Ala Val Glu Glu Asn Leu Ala Gly Glu Leu Cys
785             790             795             800

Ser Gln Cys Val Phe Asp Ser Ser Val Leu Val Arg Glu Glu Leu Ile
            805             810             815

Val Ala Leu Gln Trp Phe Val Phe Asp Phe Glu Lys Arg Phe Val Lys
            820             825             830

Phe Leu Leu Glu Leu Ser Asn Gln Ile Lys Phe Lys Leu Pro Arg Lys
            835             840             845

Arg Asn Ser Ser Glu Asn Leu Ser Glu Gln Gly Leu Asp Ile Ala Ala
850             855             860

Glu Met Pro Ser Asn His Arg Arg Pro Arg Ala Pro Pro Val Asn Glu
865             870             875             880

Phe Met Gln Pro Ser Val Ile Arg Lys Lys Met Ser Thr Ser Val Phe
            885             890             895

Ser Thr Ala Val Glu Glu Thr Val His Glu Asp Gly Ile Gly Asn Val
            900             905             910

Tyr His Ile Ala His Glu Ala Gly Asn Arg Val Glu Gln Glu Ser Glu
            915             920             925

Asp Ile Glu Tyr Arg Glu Arg Ala Lys Val Gln Ile Lys His Leu Glu
            930             935             940

Ala Lys Thr Phe Asn Glu Ala Val Ala Lys Thr Trp Leu Ser Leu Leu
945             950             955             960

Ile Leu Ser Leu Asp Pro Ile Glu Arg Val Ala Arg Met Ala Gln Lys
            965             970             975

Ile Val His Arg Val Glu Ala Gly Met Pro Glu Met Gln Ala Asn Ile
            980             985             990

Asp Asn Thr Met Ala His Leu Ser Arg Lys Met Ile Ala Arg Lys Asn
            995             1000            1005

Ser Lys Ala Thr Val Glu Met Pro Arg Lys Pro Val Gly Pro Ser Glu
            1010            1015            1020

Glu Val Ser Thr Leu Ser Glu Arg Ile Lys Arg Asn Leu Glu Val Glu

-continued

```
            1025                1030                1035                1040
Lys Glu Ser Gly Val Ser Ala Asp Gly Ile Asp Phe Thr Lys Leu Asn
                    1045                1050                1055
Met Gln Lys Ala Lys Glu Gln Arg Lys Gly Lys Gly Gln Ile
            1060                1065                1070
Lys Lys Leu Gln Asp Glu Ser Lys Val Lys Phe Gln Val Gly Ser Pro
            1075                1080                1085
Gly Asp Val Asn Gln Gln His Lys Asn Ala Leu Ser Pro Gly Ser Ser
            1090                1095                1100
Phe Thr Asp Glu Thr Gln Ser Ser Glu Leu Phe Ser Lys Asp Ser
1105                1110                1115                1120
Ser Asp Asp Asp Glu Asn Lys Ser Ala Asn Asp Glu Lys Asp Arg Ala
                    1125                1130                1135
Thr Thr Ala Ser Gly Lys Thr Val Lys Gly Ala Phe Arg Lys Ser Asp
                    1140                1145                1150
Ile Met Asp Ala Ala Leu Met Glu Phe Thr Pro Arg Arg Thr Lys Ala
            1155                1160                1165
Val Pro Gly Asp Phe Ala Val Lys Glu Glu Ser Lys Thr Leu Arg Thr
            1170                1175                1180
Val Ile Glu Asn Pro Ile Val Ser Thr Gln Phe Val Ala Trp Cys Ser
1185                1190                1195                1200
Lys Val Phe Val Glu Pro Ile Leu His Val Ile Thr Leu Asp Glu Glu
                    1205                1210                1215
Lys Ser Glu Asp Trp Glu His Glu Asp Glu Asp Glu Phe Met Pro Glu
            1220                1225                1230
Gln Phe Arg Glu Lys Ile Lys Asp Ile Gln Lys Gln Asp Arg Lys Met
            1235                1240                1245
His Glu Glu Lys Arg Ala Arg Asp Lys Lys Glu Gly Lys Lys Glu Lys
            1250                1255                1260
Ser Gln Glu Asp Val Val Val Thr Thr Thr Ile Ser Asp Trp Ala
1265                1270                1275                1280
Ile His Ala Met Glu Gly Met Leu Gln Ser Ala Asp Ile Glu Gly Arg
            1285                1290                1295
Asp Phe Gln Ser Cys Lys Tyr Asp Glu Cys Leu Trp Arg Val Lys Leu
            1300                1305                1310
Thr His Pro Ala Arg Ser Leu Thr Thr Ser Lys Leu Arg Arg Cys Met
            1315                1320                1325
Tyr Ala Ser Asp Gly Arg Leu Met Thr Ile Ile Arg Gln Asp Thr Asp
            1330                1335                1340
Thr Arg Ser Phe Arg Arg Phe Asp Leu Thr Ala Ser Asn Pro Phe Cys
1345                1350                1355                1360
Pro Ser Tyr Val Ser Gln Leu Ile Leu Ile Asn Asp Met Ser Arg Glu
                    1365                1370                1375
Met Val Ile Ala Cys Ser Thr Asn Gly Val Val Arg Ile Trp Asp Pro
            1380                1385                1390
Tyr Phe Leu Gly Trp Cys Asp Asp Tyr Glu Lys Pro Pro Glu Leu Val
            1395                1400                1405
Ser Ala Ser Phe Pro Leu Glu Ser Gln Met Lys Ile Ser Asp Glu Thr
            1410                1415                1420
Asn Arg Cys Leu Phe Asp Trp Asn Gln Gln Asn Gly Lys Leu Leu Cys
1425                1430                1435                1440
Thr Gly Thr Arg Ser Val Arg Ile Trp Asp Ala His Cys Glu Lys Val
                    1445                1450                1455
```

Cys His Asp Val Met Tyr Ser Pro Gly Ser Lys Gln Gln Thr Gly Pro
            1460                1465                1470

Gly Ala Lys Leu Asn Thr Asn Thr Leu Pro Thr Ala Met Ser Gly Asn
        1475                1480                1485

Leu Asp Glu Glu Gly Asn Met Val Ala Val Gly Tyr Ala Asp Gly Arg
    1490                1495                1500

Val Asp Tyr Phe Asp Met Arg Met Ala Asn Pro Lys Ala Ala Arg Cys
1505                1510                1515                1520

Asn Leu Ala Pro Val Asn Met Ser Lys Gln Phe Asn Asp Arg Pro Pro
                1525                1530                1535

Gly Ile Met His Leu Arg Val Asn Arg Gln Gly Phe Gly Thr Glu Leu
            1540                1545                1550

Phe Ala Gly Ser Gln Asp Gly Ser Ile Tyr Lys Leu Gln Leu Arg Met
        1555                1560                1565

Phe Lys Glu Ala Thr Pro Ser Ile Val Thr Pro Trp Glu Tyr Gly Ala
    1570                1575                1580

His Ser His Met Phe Val His Glu Asp Ser Arg Ile Leu Ala Ser Ala
1585                1590                1595                1600

Gly Gly Gly Glu Leu Ala Ile Tyr Asp Val Ala Gln Asn Lys Leu Met
                1605                1610                1615

Ala Arg Ile Leu Pro Pro Gly Glu Pro Asn Ser Met Arg Arg Asp Lys
            1620                1625                1630

Asn Ser Ser Thr Phe Gly Leu Phe Ser Ser Gln Arg Lys Leu Ser Gln
        1635                1640                1645

Val Gln Met Ser Gly Arg Met Ser Ser Met Ser Ser Ala Thr Val Gly
    1650                1655                1660

Glu Asp Arg Gln Pro Lys Val Ile Ser Leu Thr Met His Gln Met Arg
1665                1670                1675                1680

Leu Val Asp

<210> SEQ ID NO 25
<211> LENGTH: 1384
<212> TYPE: PRT
<213> ORGANISM: A. thaliana

<400> SEQUENCE: 25

Met Ala Leu Gly Asp Leu Met Val Ser Arg Phe Ser Gln Ser Ser Val
1               5                   10                  15

Ser Leu Val Ser Asn His Arg Tyr Asp Glu Asp Cys Val Ser Ser His
            20                  25                  30

Asp Asp Gly Asp Ser Arg Arg Lys Asp Ser Glu Ala Lys Ser Ser Ser
        35                  40                  45

Ser Tyr Gly Asn Gly Thr Thr Glu Gly Ala Ala Thr Ala Thr Ser Met
    50                  55                  60

Ala Tyr Leu Pro Gln Thr Ile Val Leu Cys Glu Leu Arg His Asp Ala
65                  70                  75                  80

Ser Glu Ala Ser Ala Pro Leu Gly Thr Ser Glu Ile Val Leu Val Pro
                85                  90                  95

Lys Trp Arg Leu Lys Glu Arg Met Lys Thr Gly Cys Val Ala Leu Val
            100                 105                 110

Leu Cys Leu Asn Ile Thr Val Asp Pro Pro Asp Val Ile Lys Ile Ser
        115                 120                 125

Pro Cys Ala Arg Ile Glu Ala Trp Ile Asp Pro Phe Ser Met Ala Pro
    130                 135                 140

```
Pro Lys Ala Leu Glu Thr Ile Gly Lys Asn Leu Ser Thr Gln Tyr Glu
145                 150                 155                 160

Arg Trp Gln Pro Arg Ala Arg Tyr Lys Val Gln Leu Asp Pro Thr Val
            165                 170                 175

Asp Glu Val Arg Lys Leu Cys Leu Thr Cys Arg Lys Tyr Ala Lys Thr
        180                 185                 190

Glu Arg Val Leu Phe His Tyr Asn Gly His Gly Val Pro Lys Pro Thr
    195                 200                 205

Ala Asn Gly Glu Ile Trp Val Phe Asn Lys Ser Tyr Thr Gln Tyr Ile
210                 215                 220

Pro Leu Pro Ile Ser Glu Leu Asp Ser Trp Leu Lys Thr Pro Ser Ile
225                 230                 235                 240

Tyr Val Phe Asp Cys Ser Ala Ala Arg Met Ile Leu Asn Ala Phe Ala
                245                 250                 255

Glu Leu His Asp Trp Gly Ser Ser Gly Ser Ser Gly Ser Ser Arg Asp
            260                 265                 270

Cys Ile Leu Leu Ala Ala Cys Asp Val His Glu Thr Leu Pro Gln Ser
        275                 280                 285

Val Glu Phe Pro Ala Asp Val Phe Thr Ser Cys Leu Thr Thr Pro Ile
    290                 295                 300

Lys Met Ala Leu Lys Trp Phe Cys Arg Arg Ser Leu Leu Lys Glu Ile
305                 310                 315                 320

Ile Asp Glu Ser Leu Ile Asp Arg Ile Pro Gly Arg Gln Asn Asp Arg
                325                 330                 335

Lys Thr Leu Leu Gly Glu Leu Asn Trp Ile Phe Thr Ala Val Thr Asp
            340                 345                 350

Thr Ile Ala Trp Asn Val Leu Pro His Glu Leu Phe Gln Arg Leu Phe
        355                 360                 365

Arg Gln Asp Leu Leu Val Ala Ser Leu Phe Arg Asn Phe Leu Leu Ala
    370                 375                 380

Glu Arg Ile Met Arg Ser Ala Asn Cys Asn Pro Ile Ser His Pro Met
385                 390                 395                 400

Leu Pro Pro Thr His Gln His His Met Trp Asp Ala Trp Asp Met Ala
                405                 410                 415

Ala Glu Ile Cys Leu Ser Gln Leu Pro Gln Leu Val Leu Asp Pro Ser
            420                 425                 430

Thr Glu Phe Gln Pro Ser Pro Phe Phe Thr Glu Gln Leu Thr Ala Phe
        435                 440                 445

Glu Val Trp Leu Asp His Gly Ser Glu His Lys Lys Pro Pro Glu Gln
    450                 455                 460

Leu Pro Ile Val Leu Gln Val Leu Leu Ser Gln Cys His Arg Phe Arg
465                 470                 475                 480

Ala Leu Val Leu Leu Gly Arg Phe Leu Asp Met Gly Ser Trp Ala Val
                485                 490                 495

Asp Leu Ala Leu Ser Val Gly Ile Phe Pro Tyr Val Leu Lys Leu Leu
            500                 505                 510

Gln Thr Thr Thr Asn Glu Leu Arg Gln Ile Leu Val Phe Ile Trp Thr
        515                 520                 525

Lys Ile Leu Ala Leu Asp Lys Ser Cys Gln Ile Asp Leu Val Lys Asp
    530                 535                 540

Gly Gly His Thr Tyr Phe Ile Arg Phe Leu Asp Ser Ser Gly Ala Phe
545                 550                 555                 560
```

```
Pro Glu Gln Arg Ala Met Ala Ala Phe Val Leu Ala Val Ile Val Asp
            565                 570                 575
Gly His Arg Arg Gly Gln Glu Ala Cys Leu Glu Ala Asn Leu Ile Gly
        580                 585                 590
Val Cys Leu Gly His Leu Glu Ala Ser Arg Pro Ser Asp Pro Gln Pro
        595                 600                 605
Glu Pro Leu Phe Leu Gln Trp Leu Cys Leu Cys Leu Gly Lys Leu Trp
    610                 615                 620
Glu Asp Phe Met Glu Ala Gln Ile Met Gly Arg Glu Ala Asn Ala Phe
625                 630                 635                 640
Glu Lys Leu Ala Pro Leu Leu Ser Glu Pro Gln Pro Glu Val Lys Phe
                645                 650                 655
Arg Phe Leu Tyr Asn Val Leu Arg Val Arg Ala Ala Val Phe Ala
                660                 665                 670
Leu Gly Thr Leu Leu Asp Ile Gly Phe Asp Ser Asn Lys Ser Val Val
            675                 680                 685
Glu Asp Glu Phe Asp Asp Glu Lys Ile Arg Ala Gly Asp Ala Ile
    690                 695                 700
Ile Lys Ser Leu Leu Asp Val Val Ser Asp Gly Ser Pro Leu Val Arg
705                 710                 715                 720
Ala Glu Val Ala Val Ala Leu Ala Arg Phe Ala Phe Gly His Lys Gln
                725                 730                 735
His Leu Lys Leu Ala Ala Ala Ser Tyr Trp Lys Pro Gln Ser Ser Ser
            740                 745                 750
Leu Leu Thr Ser Leu Pro Ser Ile Ala Lys Phe His Asp Pro Gly Ser
        755                 760                 765
Ala Thr Ile Val Ser Leu His Met Ser Pro Leu Thr Arg Ala Ser Thr
    770                 775                 780
Asp Ser Gln Pro Val Ala Arg Glu Ser Arg Ile Ser Ser Ser Pro Leu
785                 790                 795                 800
Gly Ser Ser Gly Leu Met Gln Gly Ser Pro Leu Ser Asp Ser Ser
                805                 810                 815
Leu His Ser Asp Ser Gly Met Met His Asp Ser Val Ser Asn Gly Ala
            820                 825                 830
Val His Gln Pro Arg Leu Leu Asp Asn Ala Val Tyr Ser Gln Cys Val
        835                 840                 845
Arg Ala Met Phe Ala Leu Ala Lys Asp Pro Ser Pro Arg Ile Ala Ser
    850                 855                 860
Leu Gly Arg Arg Val Leu Ser Ile Ile Gly Ile Glu Gln Val Val Ala
865                 870                 875                 880
Lys Pro Ser Lys Pro Thr Gly Arg Pro Gly Glu Ala Ala Thr Thr Ser
                885                 890                 895
His Thr Pro Leu Ala Gly Leu Ala Arg Ser Ser Ser Trp Phe Asp Met
            900                 905                 910
His Ala Glu Phe Phe Lys Val Leu Arg Asn Leu Arg Met Leu Phe Ile
        915                 920                 925
Leu Glu Met Leu Val Asn Ser Asn Leu Thr Leu Leu Thr Thr Gly
    930                 935                 940
Asn Leu Pro Leu Ser Phe Arg Thr Pro Val Ser Pro Pro Arg Thr
945                 950                 955                 960
Asn Tyr Leu Ser Gly Leu Arg Arg Val Cys Ser Leu Glu Phe Arg Pro
                965                 970                 975
His Leu Leu Gly Ser Pro Asp Ser Gly Leu Ala Asp Pro Leu Leu Gly
```

```
              980                 985                 990
Ala Ser Gly Ser Glu Arg Ser Leu Leu Pro Leu Ser Thr Ile Tyr Gly
            995                1000                1005

Trp Ser Cys Gly His Phe Ser Lys Pro Leu Leu Gly Gly Ala Asp Ala
        1010                1015                1020

Ser Gln Glu Ile Ala Ala Lys Arg Glu Glu Lys Lys Phe Ala Leu
1025                1030                1035                1040

Glu His Ile Ala Lys Cys Gln His Ser Ser Ile Ser Lys Leu Asn Asn
                    1045                1050                1055

Asn Pro Ile Ala Asn Trp Asp Thr Arg Phe Glu Thr Gly Thr Lys Thr
            1060                1065                1070

Ala Leu Leu His Pro Phe Ser Pro Ile Val Val Ala Ala Asp Glu Asn
        1075                1080                1085

Glu Arg Ile Arg Val Trp Asn Tyr Glu Glu Ala Thr Leu Leu Asn Gly
    1090                1095                1100

Phe Asp Asn His Asp Phe Pro Asp Lys Gly Ile Ser Lys Leu Cys Leu
1105                1110                1115                1120

Ile Asn Glu Leu Asp Asp Ser Leu Leu Leu Val Ala Ser Cys Asp Gly
                    1125                1130                1135

Ser Val Arg Ile Trp Lys Asn Tyr Ala Thr Lys Gly Lys Gln Lys Leu
            1140                1145                1150

Val Thr Gly Phe Ser Ser Ile Gln Gly His Lys Pro Gly Ala Arg Asp
        1155                1160                1165

Leu Asn Ala Val Val Asp Trp Gln Gln Gln Ser Gly Tyr Leu Tyr Ala
    1170                1175                1180

Ser Gly Glu Thr Ser Thr Val Thr Leu Trp Asp Leu Glu Lys Glu Gln
1185                1190                1195                1200

Leu Val Arg Ser Val Pro Ser Glu Ser Glu Cys Gly Val Thr Ala Leu
                    1205                1210                1215

Ser Ala Ser Gln Val His Gly Gly Gln Leu Ala Ala Gly Phe Ala Asp
            1220                1225                1230

Gly Ser Leu Arg Leu Tyr Asp Val Arg Ser Pro Glu Pro Leu Val Cys
        1235                1240                1245

Ala Thr Arg Pro His Gln Lys Val Glu Arg Val Val Gly Leu Ser Phe
    1250                1255                1260

Gln Pro Gly Leu Asp Pro Ala Lys Val Val Ser Ala Ser Gln Ala Gly
1265                1270                1275                1280

Asp Ile Gln Phe Leu Asp Leu Arg Thr Thr Arg Asp Thr Tyr Leu Thr
                    1285                1290                1295

Ile Asp Ala His Arg Gly Ser Leu Thr Ala Leu Ala Val His Arg His
            1300                1305                1310

Ala Pro Ile Ile Ala Ser Gly Ser Ala Lys Gln Leu Ile Lys Val Phe
        1315                1320                1325

Ser Leu Gln Gly Glu Gln Leu Gly Ile Ile Arg Tyr Tyr Pro Ser Phe
    1330                1335                1340

Met Ala Gln Lys Ile Gly Ser Val Ser Cys Leu Thr Phe His Pro Tyr
1345                1350                1355                1360

Gln Val Leu Leu Ala Ala Gly Ala Ala Asp Ser Phe Val Ser Ile Tyr
                    1365                1370                1375

Thr His Asp Asn Ser Gln Ala Arg
            1380

<210> SEQ ID NO 26
```

```
-continued

<211> LENGTH: 9
<212> TYPE: PRT
<213> ORGANISM: Unknown
<220> FEATURE:
<223> OTHER INFORMATION: Peptide within KIAA1303, a partial ORF for a
      human protein of unknown function.

<400> SEQUENCE: 26

Ser Val Ser Ser Tyr Gly Asn Ile Arg
 1               5

<210> SEQ ID NO 27
<211> LENGTH: 9
<212> TYPE: PRT
<213> ORGANISM: Unknown
<220> FEATURE:
<223> OTHER INFORMATION: Peptide within KIAA1303, a partial ORF for a
      human protein of unknown function.

<400> SEQUENCE: 27

Leu Asp Asp Gln Ile Phe Leu Asn Arg
 1               5

<210> SEQ ID NO 28
<211> LENGTH: 12
<212> TYPE: PRT
<213> ORGANISM: Unknown
<220> FEATURE:
<223> OTHER INFORMATION: Peptide within KIAA1303, a partial ORF for a
      human protein of unknown function.

<400> SEQUENCE: 28

Ile Pro Glu Glu His Asp Leu Glu Ser Gln Ile Arg
 1               5                  10
```

COMPLEXES COMPRISING MAMMALIAN RAPTOR POLYPEPTIDE AND MAMMALIAN MTOR POLYPEPTIDE

RELATED APPLICATIONS

This application is a continuation of U.S. application Ser. No. 12/900,289 filed Oct. 7, 2010, which is a continuation of U.S. application Ser. No. 11/788,024 filed Apr. 18, 2007, which is a continuation of U.S. application Ser. No. 10/437,421, filed May 13, 2003, which claims the benefit of U.S. Provisional Application No. 60/378,153, filed May 14, 2002. The entire teachings of the above applications are incorporated herein by reference.

GOVERNMENT SUPPORT

The invention was supported, in whole or in part, by a grant R01 AI47389 from the National Institutes of Health. The Government has certain rights in the invention.

INCORPORATION BY REFERENCE OF MATERIAL IN ASCII TEXT FILE

This application incorporates by reference the Sequence Listing contained in the following ASCII text file being submitted concurrently herewith:
  a) File name: 03992043006SEQLIST.txt; created Sep. 9, 2013, 100 KB in size.

BACKGROUND OF THE INVENTION

Increasing evidence indicates that in eukaryotes cell growth (mass accumulation) is finely regulated in response to environmental and developmental conditions and can be deranged in human diseases such as cancer and diabetes (reviewed by Dixon and Fordham-Skelton, *Curr. Opin. Plant Biol.* 1:1 (1998); Johnston and Gallant, *Bioessays* 24: 54-64 (2002); Katso et al., *Annu. Rev. Cell Dev. Biol.* 17:615-75 (2001); Kozma and Thomas, *Bioessays* 24:65-71 (2002); Schmelzle and Hall, *Cell* 103:253-62 (2000)). The rate of mass accumulation is controlled not simply by the availability of nutrients, but by signaling pathways that coordinate the activity of the cell growth machinery with nutritional, hormonal and mitogenic signals. Studies into the mechanism of action of rapamycin, an immunosuppressive and anti-cancer drug, led to the discovery of an evolutionarily conserved regulator of cell growth, the TOR (Target of Rapamycin) pathway (Brown et al., *Nature* 369:756-758 (1994); Chiu et al., *Proc. Natl. Acad. Sci. USA* 91:12574-12578 (1994); Kunz et al., *Cell* 73:585-596 (1993); Oldham et al., *Genes Dev* 14:2689-94 (2000); Sabatini et al., *Cell* 78:35-43 (1994); Sabers et al., *J. Biol. Chem.* 270:815-822. (1995); Zhang et al., *Genes Dev* 14:2712-24 (2000)). The complex of rapamycin with its receptor, FKBP12, binds directly to TOR and perturbs its function in a poorly understood fashion (Brown et al., *Nature* 377:441-446 (1995); Burnett et al., *PNAS* 95:1432-1437 (1998); Peterson et al., *Biol Chem* 275:7416-23 (2000); Zheng et al., *Cell* 82:121-130 (1995)). TOR is a member of the PIK-related family of proteins (Keith and Schreiber, *Science* 270:50-5 (1995)) that share homology with the catalytic domain of phosphatidylinositol 3-kinase (PI-3K), but appear to function as serine/threonine rather than lipid kinases. Studies in several organisms have shown that the TOR pathway regulates a variety of processes contributing to cell growth, including initiation of mRNA translation, ribosome synthesis, expression of metabolism-related genes, autophagy and cytoskeletal reorganization (recently reviewed by Schmelzle and Hall, *Cell* 103:253-62 (2000) and by Gingras et al., *Genes Dev* 15:807-26 (2001)). By interfering with the function of mammalian TOR, rapamycin inhibits progression through the G1 phase of the cell cycle in various cell types. Because of these anti-proliferative effects, rapamycin is a clinically valuable drug that is currently used to block immune rejection of transplanted organs (Saunders et al., *Kidney Int.* 59:3-16 (2001)) and in trials for the treatment of cancer (Dudkin et al., *Clin. Cancer Res* 7:1758-64 (2001); Hidalgo and Rowinsky, *Oncogene* 19, 6680-6 (2000)) and for the prevention of restenosis after angioplasty (Sousa et al., *Circulation* 104:2007-11 (2001)).

Mammalian TOR, mTOR (also known as RAFT1 or FRAP), phosphorylates at least two regulators of protein synthesis: S6K1 (formerly called p70 ribosomal S6 kinase) and an inhibitor of translation initiation, the eIF-4E binding protein 1 (4E-BP1) (Brunn et al., *Science* 277, 99-101 (1997); Burnett et al., *PNAS* 95:1432-1437 (1998); Hara et al., *J. Biol. Chem.* 272, 26457-63 (1997); Isotani et al., *J Biol Chem* 274:34493-8 (1999)). In mammalian cells, amino-acid deprivation leads to the dephosphorylation of both S6K1 and 4E-BP1 and to decreased rates of protein synthesis, effects that are rapidly reversed by the re-addition of amino acids (Fox et al., *American Journal of Physiology Cell Physiology* 274:43-1 (1998); Hara et al., *J Biol Chem* 273:14484-94 (1998)). Among amino acids, changes in leucine levels alone are sufficient to regulate the phosphorylation state and activity of both downstream components of the mTOR pathway (Hara et al., *J Biol Chem* 273:14484-94 (1998); Lynch et al., *J. Cell Biochem.* 77:234-51 (2000)). In addition to amino acid levels, mitochondrial function (Xu et al., *Diabetes* 50:353-60 (2001)), glycolysis (Dennis et al., *Science* 294:1102-5 (2001)), and cell stress (Parrott and Templeton, *J. Biol. Chem.* 274:24731-6. (1999)) regulate S6K1, as do growth factors, such as insulin (Lawrence and Brunn, *Prog. Mol. Subcell. Biol.* 26:1-31 (2001)).

Despite extensive efforts, how nutrients regulate the mTOR signaling pathway remains poorly understood. In particular, stimuli that activate (e.g. amino acids) or inhibit (e.g. mitochondrial uncouplers) downstream effectors of mTOR, such as S6K1 and 4E-BP1, fail to change the in vitro kinase activity of mTOR (Dennis et al., *Science* 294:1102-5 (2001); Hara et al., *J. Biol. Chem.* 272:26457-63 (1997)).

Thus, a greater understanding of mTOR/RAFT1/FRAP, a central component of a signaling pathway that modulates cell growth in response to nutrients and hormones and which is the target of the immunosuppressive drug rapamycin, would be useful in the diagnosis and treatment of cell growth disorders such as cancer.

SUMMARY OF THE INVENTION

As shown herein, in vivo mTOR exists in a stoichiometric complex with raptor, a novel, evolutionarily conserved protein that plays at least two roles in the mTOR pathway. Raptor is required for mTOR protein expression, nutrient-stimulated signaling to the downstream effector S6K1, and maintenance of cell size. The association of raptor with mTOR also negatively regulates the mTOR kinase activity. Conditions that repress the pathway, such as nutrient deprivation and mitochondrial uncoupling, stabilize the mTOR-raptor association and inhibit the kinase activity. Overexpression of wild-type raptor mimics nutrient deprivation, causing the formation of a stable mTOR-raptor complex with decreased mTOR kinase activity. Thus, raptor is a missing component of the TOR pathway that through its association with mTOR adjusts the rate cell of growth to nutrient levels.

Accordingly, the present invention relates to an isolated nucleic acid molecule comprising SEQ ID NO: 1 or the complement of SEQ ID NO: 1. In one embodiment, the isolated nucleic acid molecule that encodes an amino acid sequence comprises SEQ ID NO: 2. In another embodiment, the isolated nucleic acid molecule comprises a sequence that hybridizes under highly stringent conditions to SEQ ID NO: 1 or a complement of SEQ ID NO: 1. In a particular embodiment, the isolated nucleic acid molecule that comprises a sequence that hybridizes under highly stringent conditions to a complement of SEQ ID NO: 1, encodes a mammalian raptor protein.

The present invention also relates to an isolated polypeptide encoded by a nucleic acid comprising SEQ ID NO: 1. In one embodiment, the isolated polypeptide has an amino acid sequence comprising SEQ ID NO: 2.

The present invention also relates to an expression construct comprising SEQ ID NO:1. In one embodiment, SEQ ID NO: 1 in the expression construct is operably linked to a regulatory sequence.

Another aspect of the invention is a host cell comprising an isolated nucleic acid described herein. In one embodiment, the isolated nucleic acid is operably linked to a regulatory sequence.

Mammalian raptor polypeptide can be produced in a method comprising culturing a host cell comprising an isolated nucleic acid described herein under conditions in which the raptor polypeptide is produced. The method can further comprise isolating the raptor polypeptide from the cell. The present invention also relates to an isolated raptor polypeptide produced by the method.

The present invention also relates to an antibody (e.g., polyclonal antibody, monoclonal antibody) or antigen binding fragment thereof that specifically binds to a mammalian raptor polypeptide, wherein the mammalian raptor polypeptide is encoded by an isolated nucleic acid that encodes SEQ ID NO: 2. In one embodiment, the antibody recognizes an epitope from about amino acid 985 to about amino acid 1001 of SEQ ID NO: 2.

The present invention also relates to a method of identifying a nucleic acid that encodes a mammalian raptor polypeptide in a sample comprising contacting the sample with a nucleotide sequence comprising SEQ ID NO: 1 under conditions in which hybridization occurs between SEQ ID NO: 1 and the nucleic acid in the sample using high stringency conditions. The nucleic acid which hybridizes to SEQ ID NO: 1 under high stringency conditions is identified, thereby identifying a nucleic acid that encodes a mammalian raptor polypeptide in a sample.

The present invention also relates to a method of identifying a mammalian raptor polypeptide in a sample comprising contacting the sample with an antibody or antigen binding fragment thereof that specifically binds to a mammalian raptor polypeptide wherein the mammalian raptor polypeptide is encoded by an isolated nucleic acid that encodes SEQ ID NO: 2. The polypeptide which specifically binds to the antibody is identified, thereby identifying a mammalian raptor polypeptide in a sample.

The present invention also relates to a method of identifying an agent that alters interaction of a mammalian raptor protein with mammalian target of rapamycin (mTOR) protein comprising contacting a raptor protein having an amino acid sequence comprising SEQ ID NO: 2 with mTOR protein under conditions in which the raptor protein interacts with the mTOR protein, with an agent to be assessed. The extent to which raptor interacts with mTOR in the presence of the agent to be assessed is determined, wherein if the extent to which raptor interacts with mTOR is altered in the presence of the agent compared to the extent to which raptor interacts with mTOR in the absence of the agent, then the agent alters interaction of a mammalian raptor protein with mTOR protein.

The present invention also relates to a method of identifying an agent that alters interaction of a mammalian raptor protein with mammalian target of rapamycin (mTOR) protein comprising contacting a host cell which comprises isolated nucleic acid that encodes a raptor protein having an amino acid sequence comprising SEQ ID NO: 2 wherein the raptor protein, when expressed, interacts with mTOR protein in the cell, with an agent to be assessed. The growth rate and/or size of the host cell can then be assessed, wherein an altered growth rate and/or size of the host cell compared to growth rate and/or size of a control cell indicates that the agent alters interaction of a mammalian raptor protein with mTOR protein.

The present invention also relates to a method of identifying an agent that inhibits interaction of a mammalian raptor protein with mammalian target of rapamycin (mTOR) protein comprising contacting a host cell which comprises isolated nucleic acid that encodes a raptor protein having an amino acid sequence comprising SEQ ID NO: 2 wherein the raptor protein, when expressed, interacts with mTOR protein in the cell, with an agent to be assessed. The growth rate and/or size of the host cell is then assessed, wherein a decrease in growth rate and/or size of the host cell compared to growth rate and/or size of a control cell indicates that the agent inhibits interaction of a mammalian raptor protein with mTOR protein. In one embodiment, the growth rate or size of the cell can be assessed by measuring phosphorylation of a regulator of protein synthesis selected from the group consisting of: S6 kinase 1, 4E-BP1 and combinations thereof. In another embodiment, the growth rate or size is assessed by measuring binding of the mammalian raptor protein with mTOR protein.

The present invention also relates to a method of identifying an agent that enhances interaction of a mammalian raptor protein with mammalian target of rapamycin (mTOR) protein comprising contacting a host cell which comprises isolated nucleic acid that encodes a raptor protein having an amino acid sequence comprising SEQ ID NO: 2 wherein the raptor protein, when expressed, interacts with mTOR protein in the cell, with an agent to be assessed. The growth rate and/or size of the host cell is then assessed, wherein an increase in growth rate and/or size of the host cell compared to growth rate and/or size of a control cell indicates that the agent enhances interaction of a mammalian raptor protein with mTOR protein.

The present invention provides a method of altering the growth and/or size of a cell comprising introducing into the cell an agent that alters interaction of raptor protein with mTOR protein. In one embodiment, the present invention provides a method of enhancing growth rate and/or size of a cell comprising introducing into the cell an agent that inhibits interaction of mammalian raptor protein with mammalian TOR protein. The agent can be, for example, exogenous nucleic acid that inhibits activity of a mammalian raptor protein. In one embodiment, the exogenous nucleic acid can result in overexpression of mammalian raptor protein in the cell. In one embodiment, the exogenous nucleic acid is mRNA that specifically targets and destroys the mammalian raptor protein. In a particular embodiment, the mRNA that specifically targets and destroys the mammalian raptor protein comprises pairs of oligoribonucleotides which correspond to nucleotides from about nucleotide 1531 to about nucleotide 1551 of SEQ ID NO: 1.

In another embodiment, the present invention provides a method of inhibiting growth rate and/or size of a cell comprising introducing into the cell an agent that enhances interaction of mammalian raptor protein with mammalian TOR protein. The agent can be, for example, exogenous nucleic acid that enhances activity of a mammalian raptor protein.

The present invention also relates to a method of altering kinase activity of mTOR protein in a cell comprising introducing into the cell an agent that alters interaction of a mammalian raptor protein with the mTOR. In one embodiment, the invention relates to a method of enhancing kinase activity of mTOR protein in a cell comprising introducing into the cell an agent that inhibits interaction of a mammalian raptor protein with the mTOR. In another embodiment, the invention relates to a method of inhibiting kinase activity of mTOR protein in a cell comprising introducing into the cell an agent that enhances interaction of a mammalian raptor protein with the mTOR.

The present invention also relates to a method of treating cancer in an individual comprising administering to the individual an agent that enhances an interaction of raptor protein with mTOR protein.

Another aspect of the present invention is a method of identifying proteins that associate with mTOR within a cell comprising contacting a lysate of the cell with a reversible crosslinker (e.g., dithiobis(succinmidylpropionate) (DSP)) thereby forming a crosslink between proteins that associate with mTOR within the cell. Proteins that are associated by the crosslink are separated from the lysate, thereby identifying proteins that associate with mTOR within a cell. In one embodiment, the proteins that are associated by the crosslink are separated from the lysate using an antibody that specifically binds one of the proteins (e.g., mTOR). The method can further comprise reducing the crosslink between the proteins using a reducing agent (e.g., dithiothreitol) and isolating the proteins.

The present invention also relates to a method of identifying proteins that associate with mTOR within a cell, comprising preparing a lysate of the cell with a buffer comprising a detergent other than Triton (e.g., CHAPS), thereby preserving an association between the proteins. The proteins that are associated are then separated from the lysate, thereby identifying proteins that associate with mTOR within a cell. The method can further comprise isolating the proteins that are associated from one another. In one embodiment, the buffer comprises about 0.05% to about 2% CHAPS. In a particular embodiment, the buffer comprises about 0.3% CHAPS and can further comprise 120 mM NaCl. In one embodiment a crosslinker is not used.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A-1C are the nucleotide sequence (SEQ ID NO: 1) of human raptor.

FIG. 2 is the amino acid sequence (SEQ ID NO: 2) of human raptor.

FIG. 3A is an autoradiograph of SDS-PAGE analysis of mTOR immunoprecipitates prepared from metabolically labeled HEK293T cells lysed in the absence (−) or presence (+) of the chemical cross-linker DSP, or from lysates treated with DSP 30 minutes after lysis (30'+). A 150 kDa protein is present only in immunoprecipitates prepared with an anti-mTOR antibody and not with antibodies recognizing the EGF receptor (EGFR), the 110 kDa catalytic subunit of PI-3-kinase (PI3K p110), the ribosomal S6 kinase (S6K1), actin, or lamin. Bands representing EGFR and PIK3 are visible on the autoradiograph, while S6K1, actin and lamin have run off the gel.

FIG. 3B is a silver stained SDS-PAGE analysis of mTOR immunoprecipitates isolated from cells lysed in the absence (−) or presence (+) of DSP. Quantitation of the bands corresponding to mTOR and p150 reveals a ratio of 1.0 mTOR to 0.84 p150.

FIG. 3C is a gel showing near stoichiometric amounts of mTOR and p150 in mTOR immunoprecipitates prepared from cells metabolically labeled to equilibrium. Quantitation of the bands correspond to mTOR and p150 reveals, after normalization to the methionine content of each protein, a ratio of 0.92 mTOR to 1.0 p150.

FIGS. 4A-4E show that raptor is an evolutionarily conserved protein and is widely expressed in human tissues in a similar pattern to mTOR.

FIG. 4A is a schematic representation of structural features of Raptor showing the conserved domain organization of raptor homologues from five eukaryotic species. Boxes labeled 1, 2, and 3 are sequence blocks that make up the Raptor N-terminal Conserved (RNC) domain and are 67-79% similar in the species shown. Block 2 of the *S. cerevisiae* raptor has a small insertion that makes it slightly larger than the same block in the other species. The seventh WD-40 repeat of *C. elegans* raptor is indicated with an empty green box because it lacks the prototypical Trp/Asp pattern. The accession numbers for the raptor homologues are: *D. melanogaster* (AAF46122), *S. pombe* (P87141), *S. cerevisiae* (P38873), *C. elegans* (T19183), *A. thaliana* (NP_187497).

FIGS. 4B-4D is an amino acid sequence alignment of the sequence blocks (labeled Block 1, Block 2, and Block 3) of the RNC domain from the *H. sapiens* (SEQ ID NO: 3 (Block 1); SEQ ID NO: 4 (Block 2); SEQ ID NO: 5 (Block 3)), *D. melanogaster* (SEQ ID NO: 6 (Block 1); SEQ ID NO: 7 (Block 2); SEQ ID NO: 8 (Block 3)), *S. pombe* (SEQ ID NO: 9 (Block 1); SEQ ID NO: 10 (Block 2); SEQ ID NO: 11 (Block 3)), *S. cerevisiae* (SEQ ID NO: 12 (Block 1); SEQ ID NO: 13 (Block 2); SEQ ID NO: 14 (Block 3)), *C. elegans* (SEQ ID NO: 15 (Block 1); SEQ ID NO: 16 (Block 2); SEQ ID NO: 17 (Block 3)), and *A. thaliana* (SEQ ID NO: 18 (Block 1); SEQ ID NO: 19 (Block 2); SEQ ID NO: 20 (Block 3)) species in FIG. 4A, showing identical (*), conserved (double dot) and partially conserved (single dot) residues. A ClustalX color scheme is used to depict characteristics of amino acids (Thompson et al., *Nucleic Acids Res.*, 25:4876-4882, (1997)).

FIG. 4E is a northern blot analysis of a multiple human tissue blot (Clontech) for raptor, mTOR and β-actin showing similar patterns of expression for raptor and mTOR.

FIG. 5A is a western blot analysis showing levels of raptor (bottom panel) and mTOR (top panel) in immunoprecipitates prepared with two different mTOR antibodies or 5 control antibodies. mTOR Ab1 and Ab2 are anti-peptide antibodies produced against amino acids 1-18 and 221-237, respectively, of human mTOR.

FIG. 5B is a western blot showing that in the absence of the cross-linker, cell lysis conditions affect the mTOR-raptor association. Western blot showing levels of raptor (bottom panel) and mTOR (top panel) in mTOR immunoprecipitates from cells lysed in buffers containing the indicated concentrations of Triton X-100 or CHAPS. Increasing concentrations (100, 200, 300 mM) of NaCl in the lysis buffer dissociate raptor from mTOR.

FIG. 5C is a western blot showing that Raptor and mTOR associate in cell lines derived from several human tissues. mTOR immunoprecipitates prepared from lysates (1 mg total protein) of the indicated cell types were analyzed as in FIG. 5B.

FIG. 5D is a western blot showing that endogenous mTOR interacts with recombinant raptor but not γ-tubulin. Western blot showing levels of mTOR (top panel) and myc-raptor and myc-tubulin (bottom panel) in anti-myc immunoprecipitates from HEK293T cells transfected with 100 ng of either a myc-raptor- or a myc-γ-tubulin-encoding plasmid.

FIG. 5E is a western blot showing that recombinant mTOR and raptor interact in transfected HEK293T cells. Western blot showing levels of HA-raptor (top panel) and myc-mTOR and myc-γ-tubulin (middle panel) in anti-myc immunoprecipitates prepared from HEK293T cells transfected with 1 ug of a plasmid encoding HA-raptor and 100 ng of either a myc-raptor- or a myc-γ-tubulin-encoding plasmid. HA-raptor expression levels in the cell lysates used for immunoprecipitations (bottom panel).

FIG. 6A is a gel showing that Raptor interacts with the N-terminal portion of mTOR containing the HEAT repeats. Myc-tagged full-length mTOR, its indicated fragments or γ-tubulin were co-expressed in HEK293T cells with HA-raptor, and anti-myc immunoprecipitates analyzed by SDS-PAGE and anti-HA immunoblotting (top panel). Western blot showing amounts of mTOR, its fragments or γ-tubulin in the immunoprecipitates (middle panel). HA-raptor expression levels in the cell lysates used for the immunoprecipitations (bottom panel).

FIG. 6B is a schematic and a western blot showing the requirement of the complete raptor protein for the interaction with mTOR and identification of raptor mutants incapable of binding mTOR. Raptor fragments and location of raptor mutations used in this study are indicated in the schematic. Western blot analysis showing levels of mTOR (top panel) in anti-HA immunoprecipitates prepared from HEK293T cells transfected with 1 μg of plasmids encoding HA-tagged raptor, its fragments or the mutants shown in the schematic. Anti-HA western blot analysis showing levels of full-length raptor or fragments in the immunoprecipitates (bottom panel).

FIG. 7A is a western blot showing that siRNA-induced reductions in raptor levels inhibit leucine-stimulated signaling to S6K1. HEK293T cells transfected with siRNAs targeting lamin, mTOR, or raptor, were incubated in leucine-free RPMI for 50 minutes. Cells were left unstimulated (first lane in each group of four) or stimulated for 10 minutes with increasing amounts of leucine (5.2, 16, and 52 μg/ml). Cell lysates were prepared and 20 μg of each analyzed by western blotting to determine levels of indicated proteins or protein phosphorylation states. P—S6K1 and P-PKB/Akt indicate S6K1 phosphorylated on T389 and PKB/Akt on 5473, respectively.

FIG. 7B is a bar graph showing reductions in raptor or mTOR inhibit leucine-stimulated S6K1 phosphorylation and lower protein levels of both mTOR and raptor. The graph shows mean±S.D. derived from three independent experiments performed as in FIG. 5A and quantitated by densitometry. Table shows means±S.D. (n=4) of protein levels of mTOR, raptor, S6K1, PkB/Akt, and ATM determined by densitometry from immunoblots in FIG. 5A.

FIG. 7C is a western blot and graphs showing that in actively growing HEK293T cells, reductions in the levels of raptor or mTOR reduce the phosphorylation state of S6K1 and cell size. Cells were transfected with siRNAs and the cell lysates analyzed by western blotting for mTOR, raptor, phospho-S6K1, and S6K1. Cell diameters and volumes were determined three days after transfection using a particle size counter (Coulter Multisizer II). Graphs show size distributions of cells transfected with the indicated siRNAs or treated with 20 nM rapamycin for 48 hours (red lines) overlaid on size distribution of non-transfected cells (black line). The mean±S.D. (μm) cell diameters are: non-transfected cells 15.92±0.11 (n=5); lamin siRNA cells 15.89±0.10 (n=5); mTOR siRNA 15.43±0.09 (n=6); raptor siRNA 15.45±0.07 (n=6); rapamycin treated cells 14.61±0.10 (n=5). The mean±S.D. (μL) for the cell volumes are: non-transfected cells 2111±44 (n=5); lamin siRNA cells 2099±39 (n=5); mTOR siRNA 1922±33 (n=6); raptor siRNA 1930±26 (n=6); rapamycin treated cells 1632±33 (n=5). Mean±S.D. values were obtained from the indicated numbers of independent trials in which at least 10,000 cells were analyzed per trial. The reductions in size caused by the raptor and mTOR siRNA and by rapamycin are significant to $p<0.001$.

FIG. 7D is a graph showing transfection of HEK293T cells with siRNA targeting raptor or mTOR reduces the capacity of cells to attain a normal mean size after emerging from a confluence-induced shrinking in cell size. Cells transfected with the indicated siRNA were grown to confluence, induced into active growth by dilution into fresh media and cell volumes determined at 1, 2, and 3 days after dilution. For comparison, non-transfected cells were treated with 20 nM rapamycin at 1 day after dilution. Shown are mean±S.D. from three independent experiments. The reductions in size caused by the raptor and mTOR siRNA are significant to $p<0.01$ and 0.05 at the 2 and 3 day time points, respectively.

FIG. 7E is a graph showing that transfection of HEK293T cells with siRNA targeting raptor or mTOR or treatment with rapamycin inhibits leucine-induced increases in cell size. Cells were transfected with the indicated siRNAs and the experiment performed as described herein. The growth rates were estimated as 1.85, 1.06, 1.03, and 1.02% volume per hour for the cells transfected with the lamin, mTOR, and raptor siRNAs, and for cells treated with rapamycin, respectively. Shown are mean±S.D. from samples for each time point. The reductions in size caused by the raptor and mTOR siRNAs and by rapamycin at 10 hours are significant to $p<0.05$.

FIG. 8A is a gel showing deprivation of amino acids, leucine, or glucose increases the stability of raptor-mTOR complex and decreases mTOR kinase activity, effects reversed by stimulation with leucine or glucose. HEK293T cells were incubated for 50 minutes in RPMI lacking amino acids (−amino acids), leucine (−leucine), or glucose (−glucose) or left untreated (control). Duplicate plates of cells deprived of leucine or glucose were stimulated for 10 minutes with 52 μg/ml leucine (−leu+leu) or 11 mM glucose (−gluc+gluc), respectively. Cells were lysed, anti-mTOR immunoprecipitates prepared, and mTOR kinase activity determined with in vitro kinase assays containing ATP-[γ-$^{32}$P] and a GST-S6K1 fusion protein (Burnett et al., *PNAS* 95:1432-1437 (1998)). Kinase reactions were resolved by SDS-PAGE, proteins transferred to PVDF, $^{32}$P-incorporation into GST-S6K1 detected with autoradiography (third panel from top) and levels of mTOR (top panel) and raptor (middle panel) determined by immunoblotting. Western blot analyses of cell lysates used to prepare mTOR immunoprecipitates showing effects of nutrient conditions on the phosphorylation state and gel mobility of S6K1 in vivo (bottom two panels).

Figure 8A:
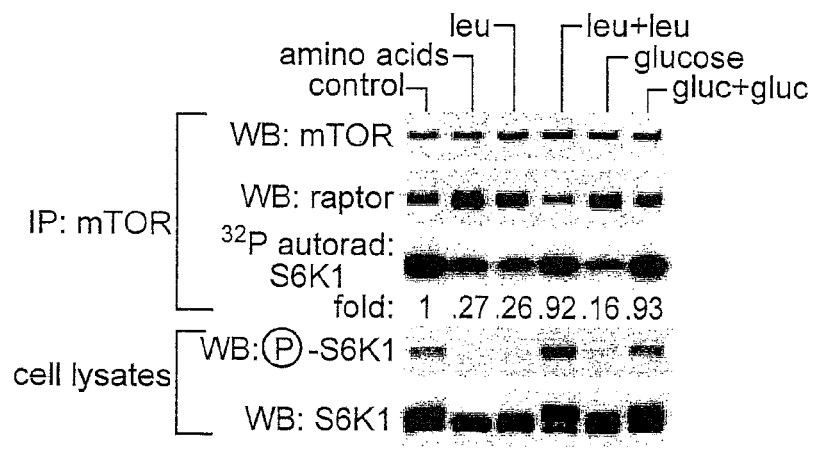
FIGS. 8A-8E are gels showing that nutrients, mitochondrial function, and glycolysis regulate both the mTOR-raptor interaction and mTOR kinase activity.
Figure 8B:
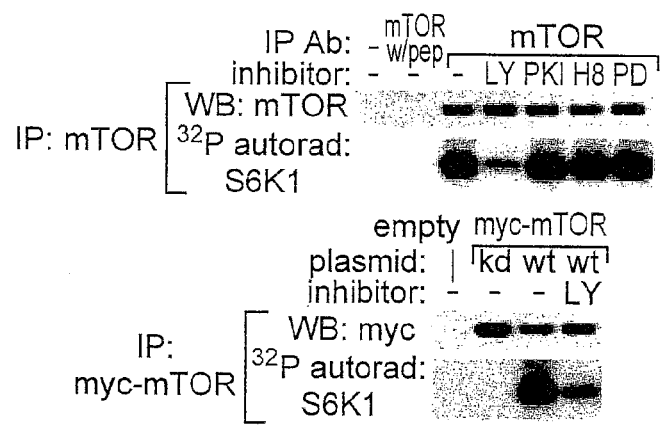

FIG. 8B is a gel showing that the kinase activity of immunoprecipitates of endogenous mTOR depends on the presence of mTOR and is sensitive to 20 µM LY294002 (LY) but not to 40 nM Protein Kinase A Inhibitor (PKI), 20 µM H-8 (H8), and 20 µM PD98059 (PD). The kinase activity of recombinant, myc-tagged mTOR (wt) is absent in the D2357E mutant (kd) and is sensitive to 20 µM LY294002 (LY).

Figure 8C:
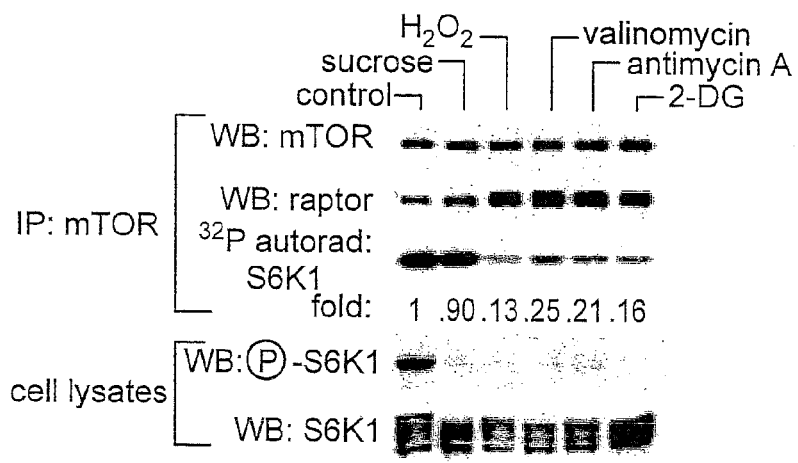

FIG. 8C is a gel showing that mitochondrial function, glycolysis and oxidative stress regulate the mTOR-raptor interaction and the mTOR kinase activity. Cells were treated for 10 minutes with 500 mM sucrose, 1 mM $H_2O_2$, 1 µm valinomycin A, or 100 mM 2-deoxyglucose (2-DG) or left untreated (control). mTOR kinase activity, the amounts of mTOR and raptor in mTOR immunoprecipitates, and the in vivo phosphorylation states of S6K1 were analyzed as in FIG. 8A.

Figure 8D:
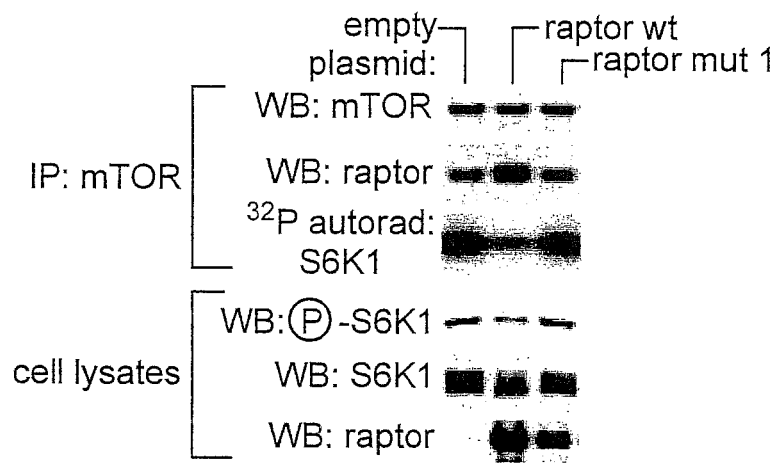

FIG. 8D is a gel showing that overexpression of wild-type raptor increases the amount of the stable mTOR-raptor complex, leading to decreases in the in vitro kinase activity of mTOR and in the in vivo phosphorylation state of S6K1. HEK293T cells were transfected with 5 µg of an empty vector (prk5), a mammalian expression vector encoding wild-type raptor (raptor wt) or a mutant incapable of interacting with mTOR (raptor mut 1). mTOR activity and levels of the mTOR-raptor interaction were analyzed as in FIG. 8A. Western analyses of cell lysates used to prepare mTOR immunoprecipitates shows the effects of overexpression of wild type raptor on the phosphorylation state and gel mobility of S6K1 and amounts of expressed wild-type and mutant raptor (bottom panel).

Figure 8E:
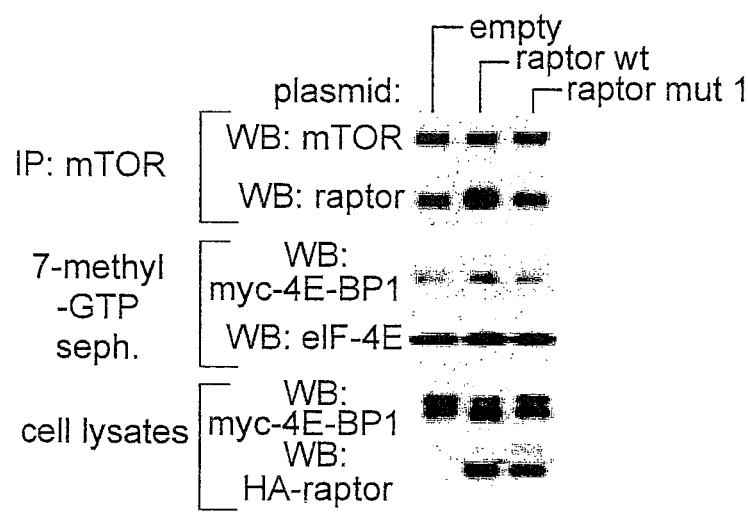

FIG. 8E is a gel showing that overexpression of wild-type raptor increases the amount of 4E-BP1 bound to eIF-4E. Experiments were performed as in FIG. 8D except the cells were also transfected with 50 ng of a plasmid encoding myc-4E-BP1. 7-methyl-GTP-affinity chromatography and eIF-4E western blotting were performed as described in Burnett et al., *PNAS*, 95:1432-1437 (1998).

Figure 9A:
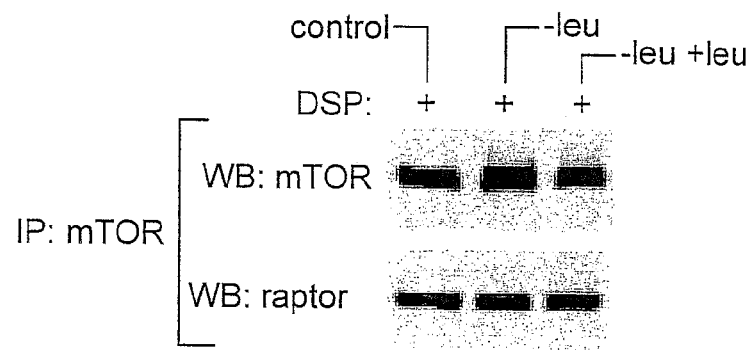
Figure 9B:
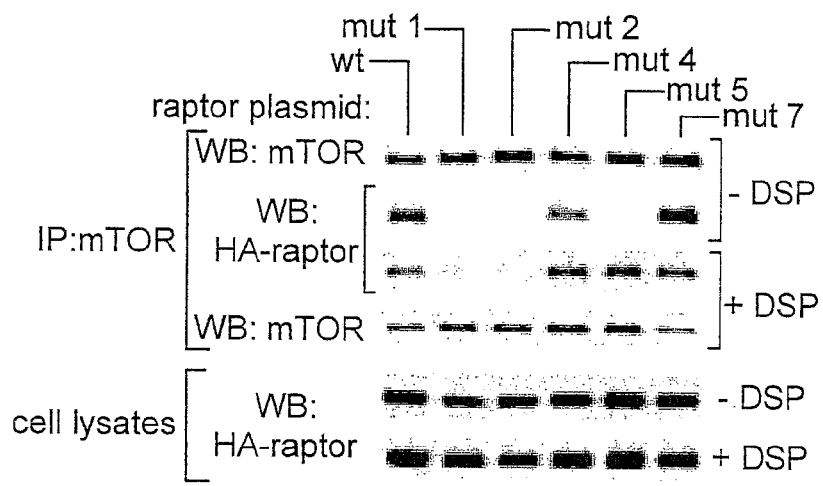
Figure 9C:
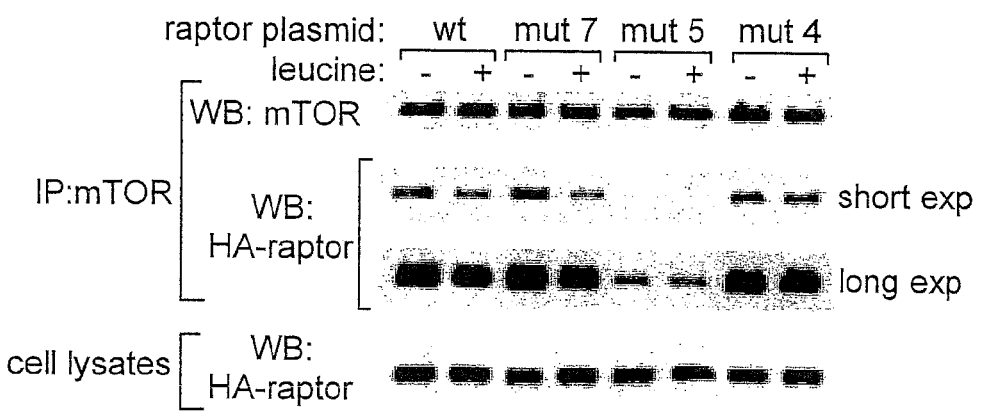

FIGS. 9A-9C are gels that provide evidence that the mTOR-raptor complex exists in two binding states.

FIG. 9A is a gel showing that raptor amounts in mTOR immunoprecipitates prepared from cells grown in leucine-rich or -poor conditions are similar when cells are lysed in the presence of cross-linker DSP.

FIG. 9B is a gel showing that raptor mutant 5 forms an unstable complex with mTOR. Experiments were performed under nutrient-rich conditions as in FIG. 9A except that cells were transfected with 10 ng of the indicated raptor plasmid 24 hours before mTOR immunoprecipitations. Western blots show amounts of mTOR and indicated HA-raptors recovered in mTOR immunoprecipitates (top panels) prepared from cells lysed in the absence or presence of the cross-linker DSP and expression levels of the raptor mutants in the cell lysates (bottom panels).

FIG. 9C is a gel showing that the interactions of raptor mutants 4 and 5 with mTOR are not regulated by nutrients. HEK293T cells transfected with 10 ng of the indicated raptor plasmids were incubated for 50 minutes in leucine-free (–) or rich (+) media. The amounts of mTOR and HA-raptor in the mTOR immunoprecipitates were analyzed as in FIG. 9B (short exp). A longer exposure of the western blot was necessary to see that leucine levels do not regulate the residual interaction between raptor mutant 5 and mTOR (long exp).

Figure 10A:
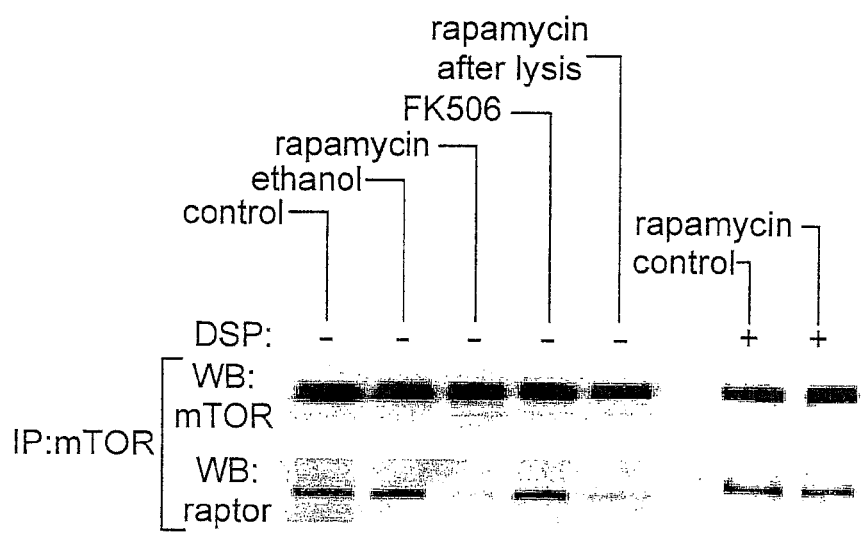
Figure 10B:
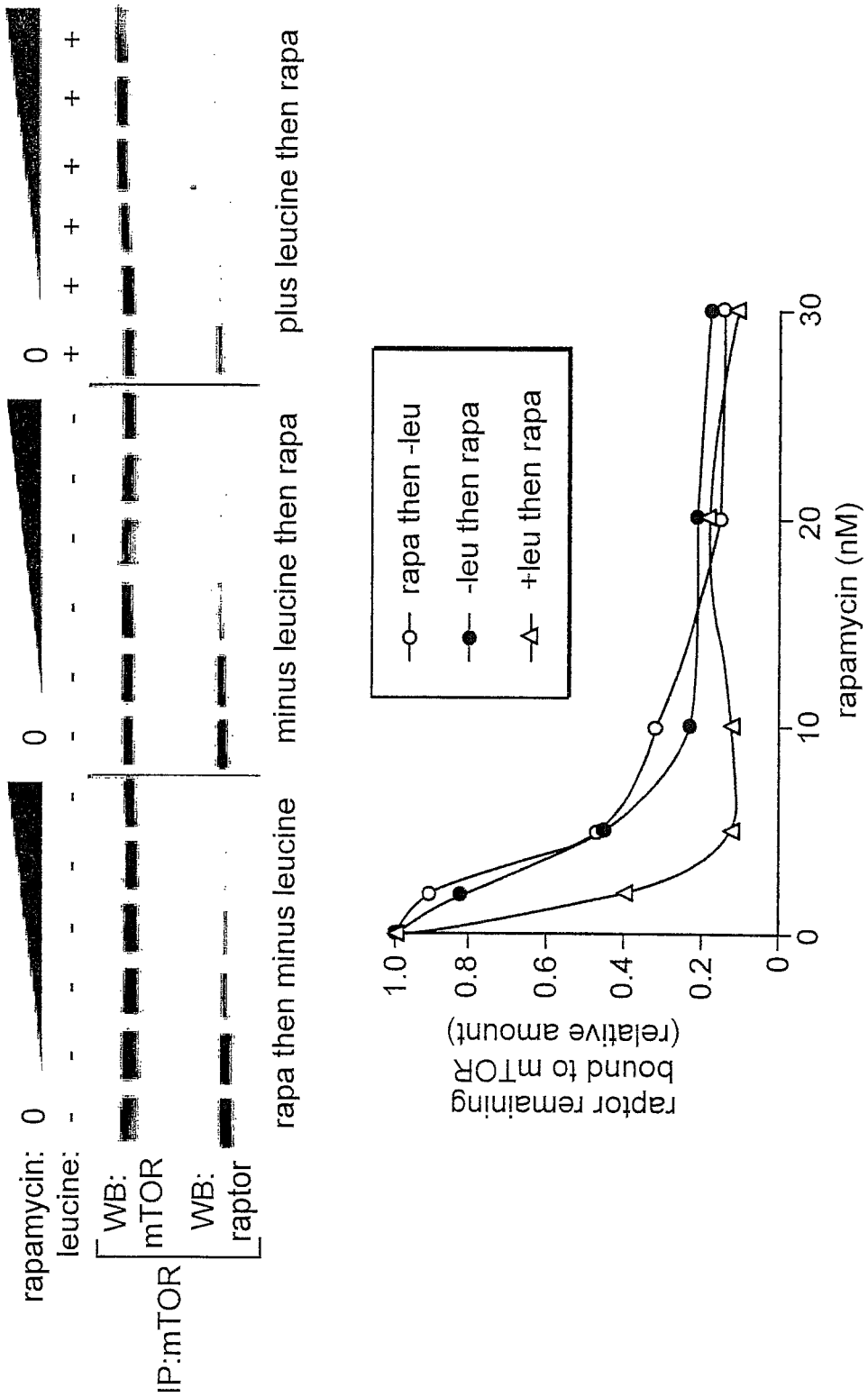
Figure 10C:
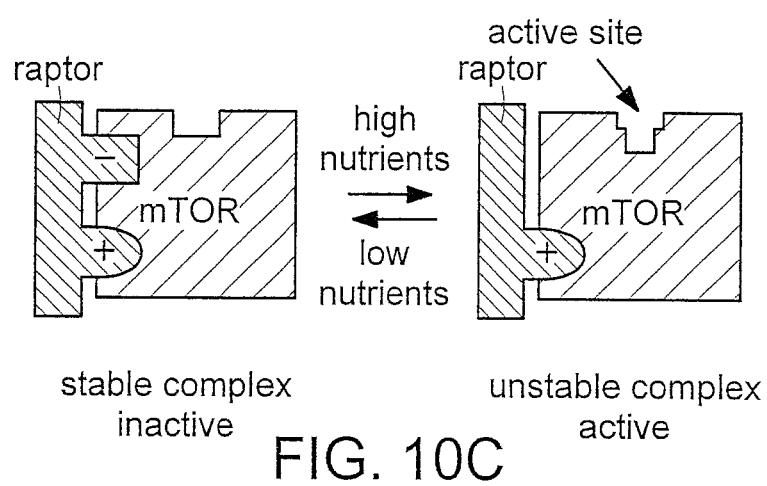
Figure 11B:
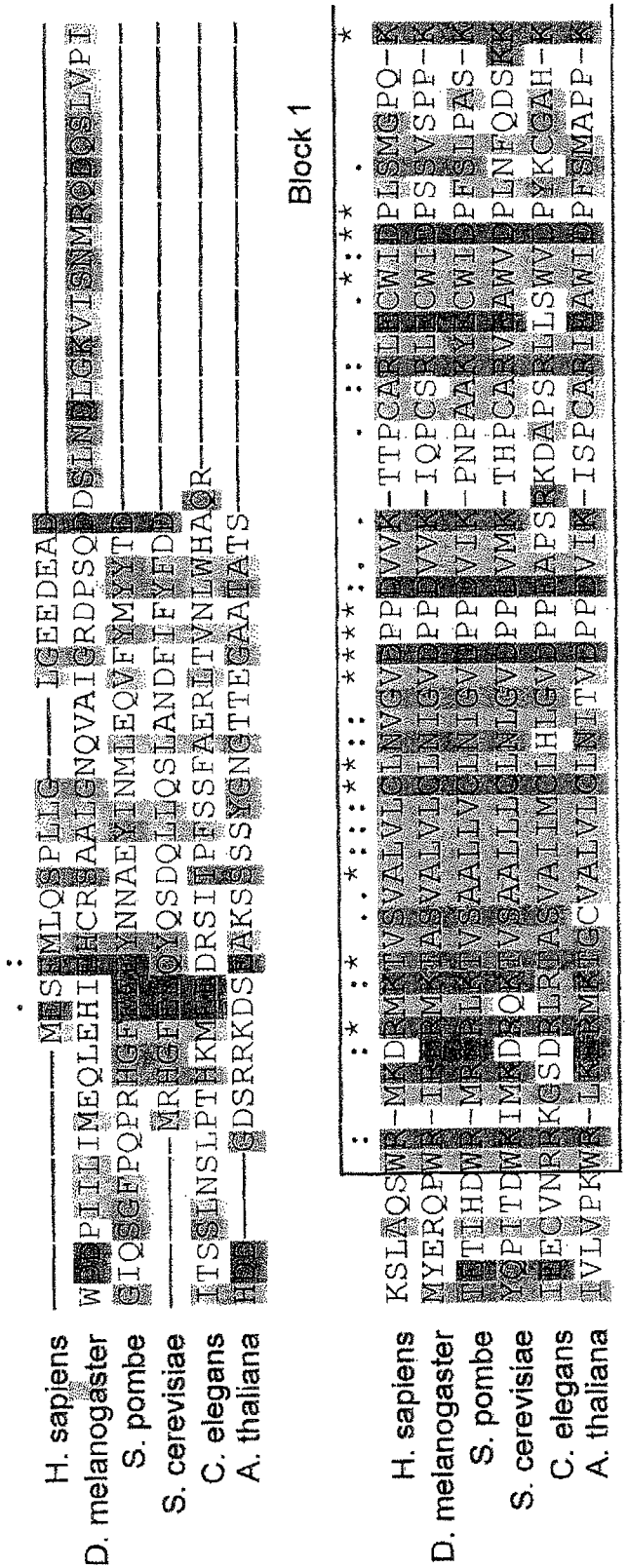

FIGS. 10A-10C show that rapamycin destabilizes the mTOR-raptor interaction under either leucine-rich or poor conditions.

FIG. 10A is a gel showing that rapamycin added before or after cell lysis disrupts the mTOR-raptor interaction. HEK293 cells were treated for 10 min with 10 nM rapamycin, 10 nM FK506, or appropriate amounts of ethanol vehicle before cell lysis or with 10 nM rapamycin for 30 minutes after lysis. mTOR immunoprecipitates were obtained and the amounts of mTOR (top panel) and co-precipitating Raptor determined (bottom panel). The inclusion of the DSP cross-linker in the lysis buffer maintains the mTOR-raptor interaction even with rapamycin treatment.

FIG. 10B is a gel showing that rapamycin destabilizes the mTOR-raptor interaction in leucine-poor or rich conditions. HEK293 cells were treated with increasing concentrations of rapamycin (0, 2, 5, 10, 20, or 30 nM) for 20 min before (leftmost panels) or after (middle panels) incubation of cells for 30 minutes in leucine-free RPMI or after incubation for 30 minutes in leucine-rich RPMI (rightmost panels). The amount of raptor (bottom panels) coprecipitated with mTOR was quantitated, normalized to the amount obtained in the absence of rapamycin (first lane in each group) and plotted against the rapamycin concentration. The EC50 of rapamycin for dissociation of raptor from mTOR decreases from about 5 nM in the absence of leucine (irrespective of order of rapamycin addition or leucine deprivation) to about 1.5 nM in the presence of leucine (graph).

FIG. 10C is a model to explain effects of nutrients on the mTOR-raptor complex and the mTOR activity. It is propose that raptor makes a constitutive interaction with mTOR that provides a positive input to mTOR function (+) and a nutrient-sensitive interaction that inhibits the mTOR kinase activity (–). In the model, high nutrient conditions lead to the formation of the 'unstable complex' from the 'stable complex' by displacing the nutrient-sensitive interaction.

Figure 11D:
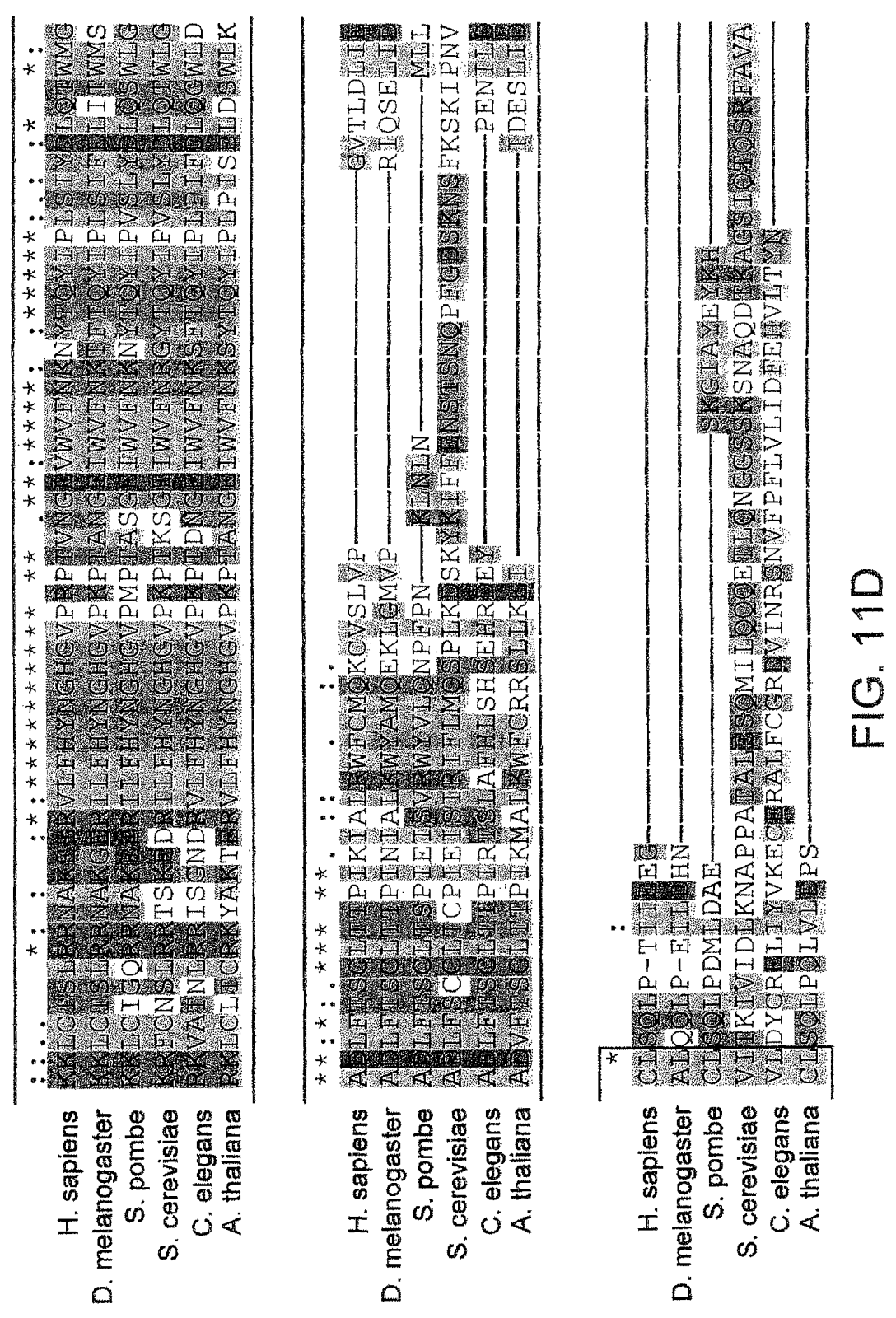
Figure 11E:
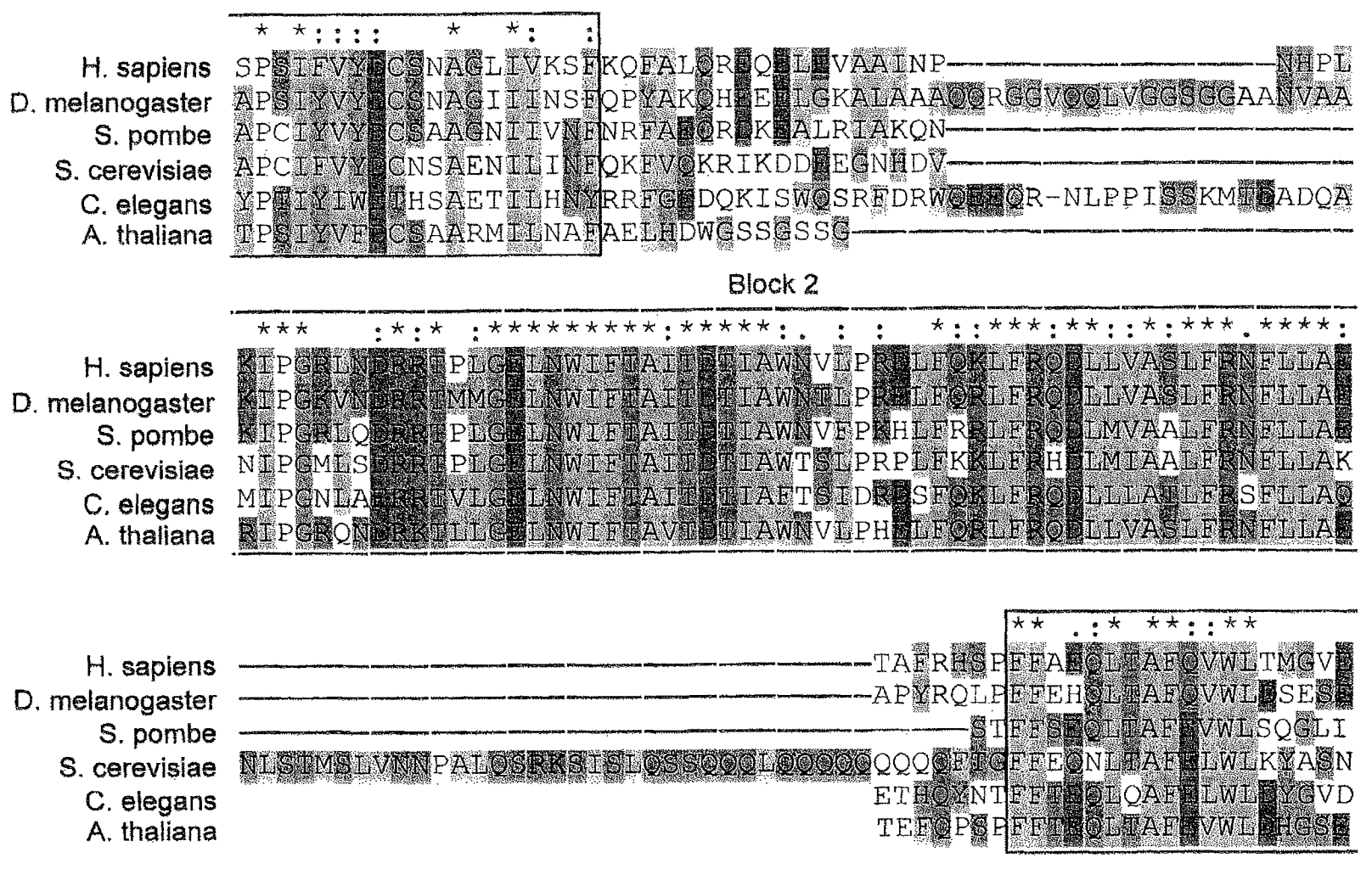
Figure 11G:
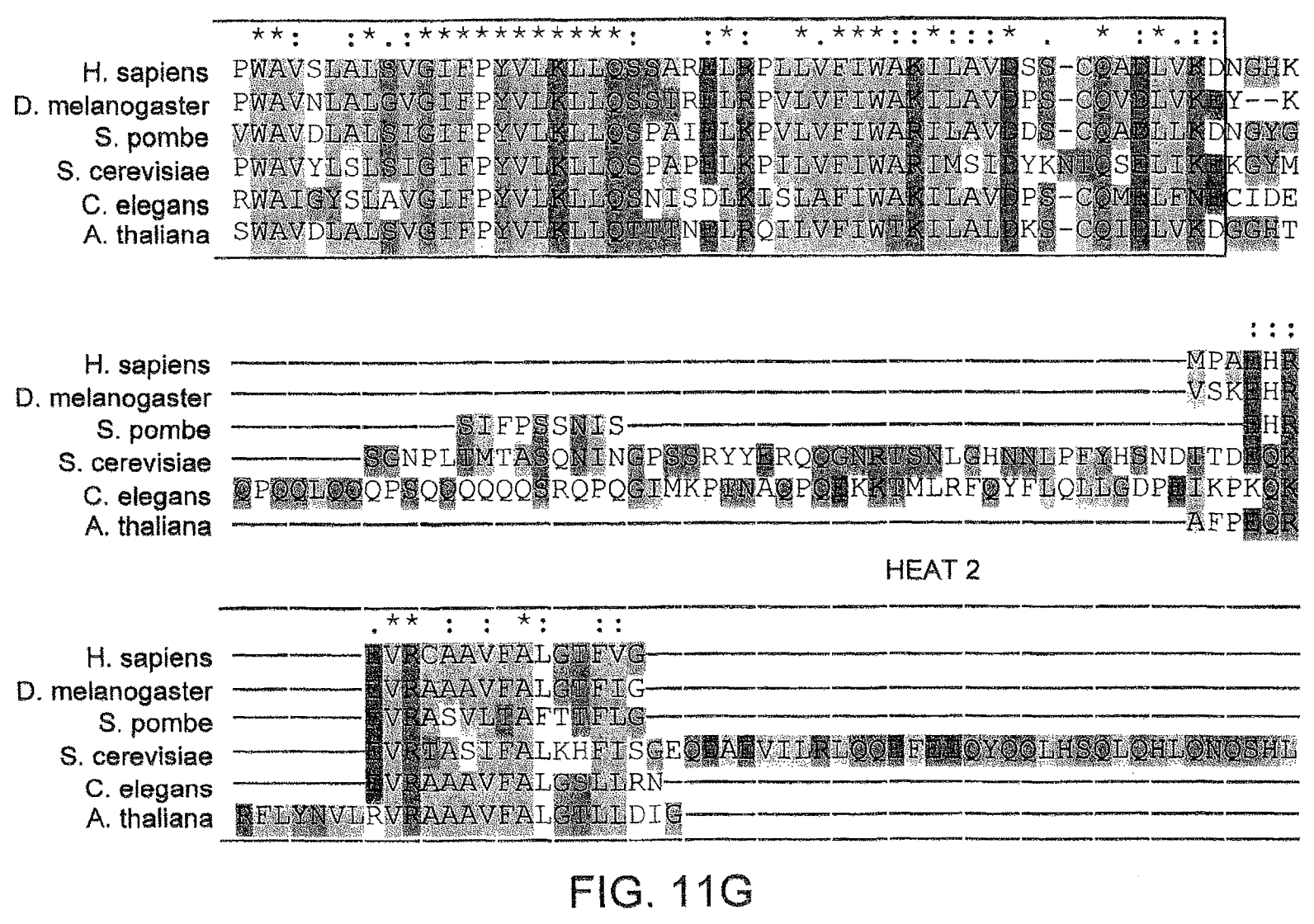
Figure 11H:
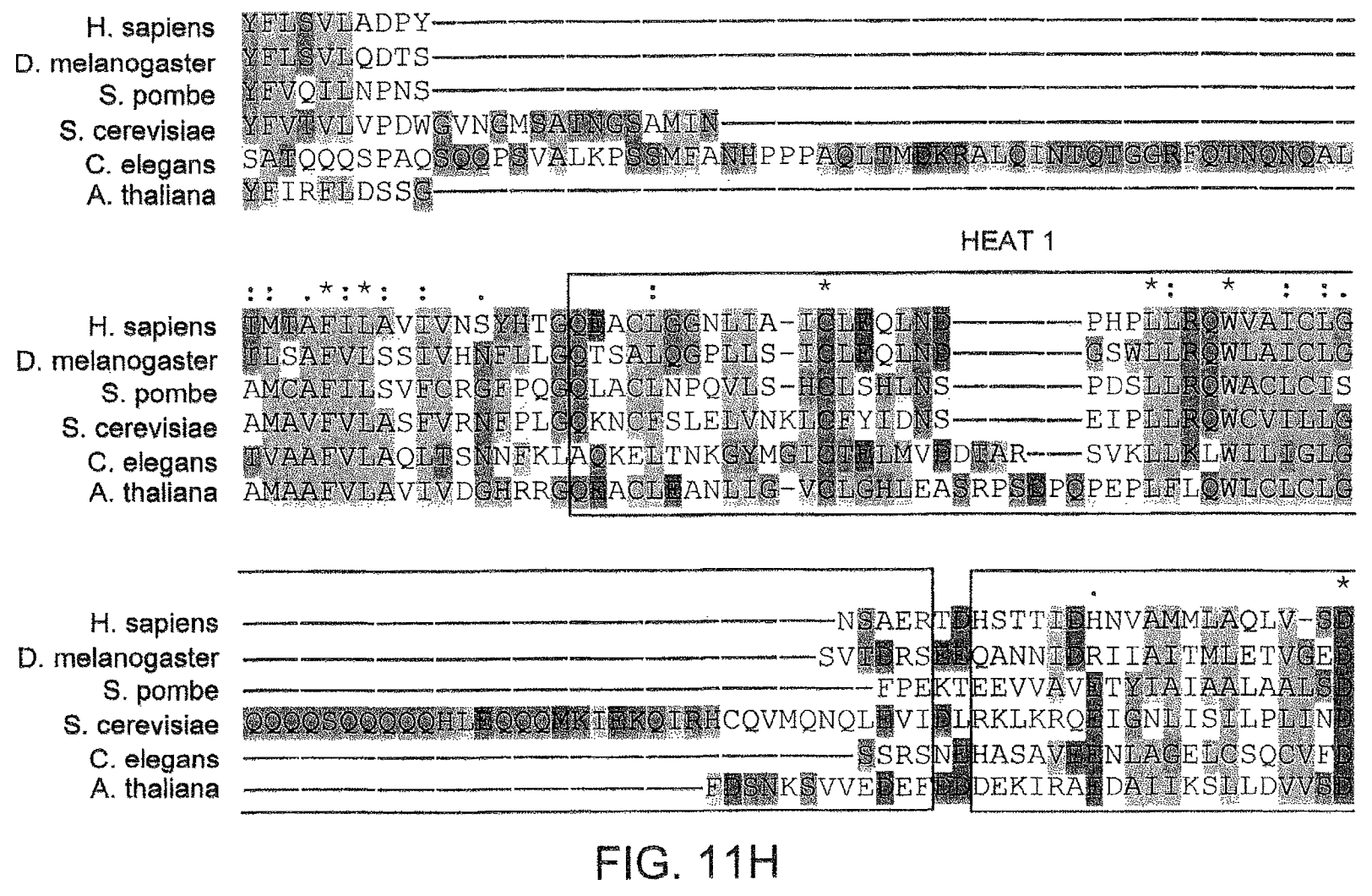
Figure 11I:
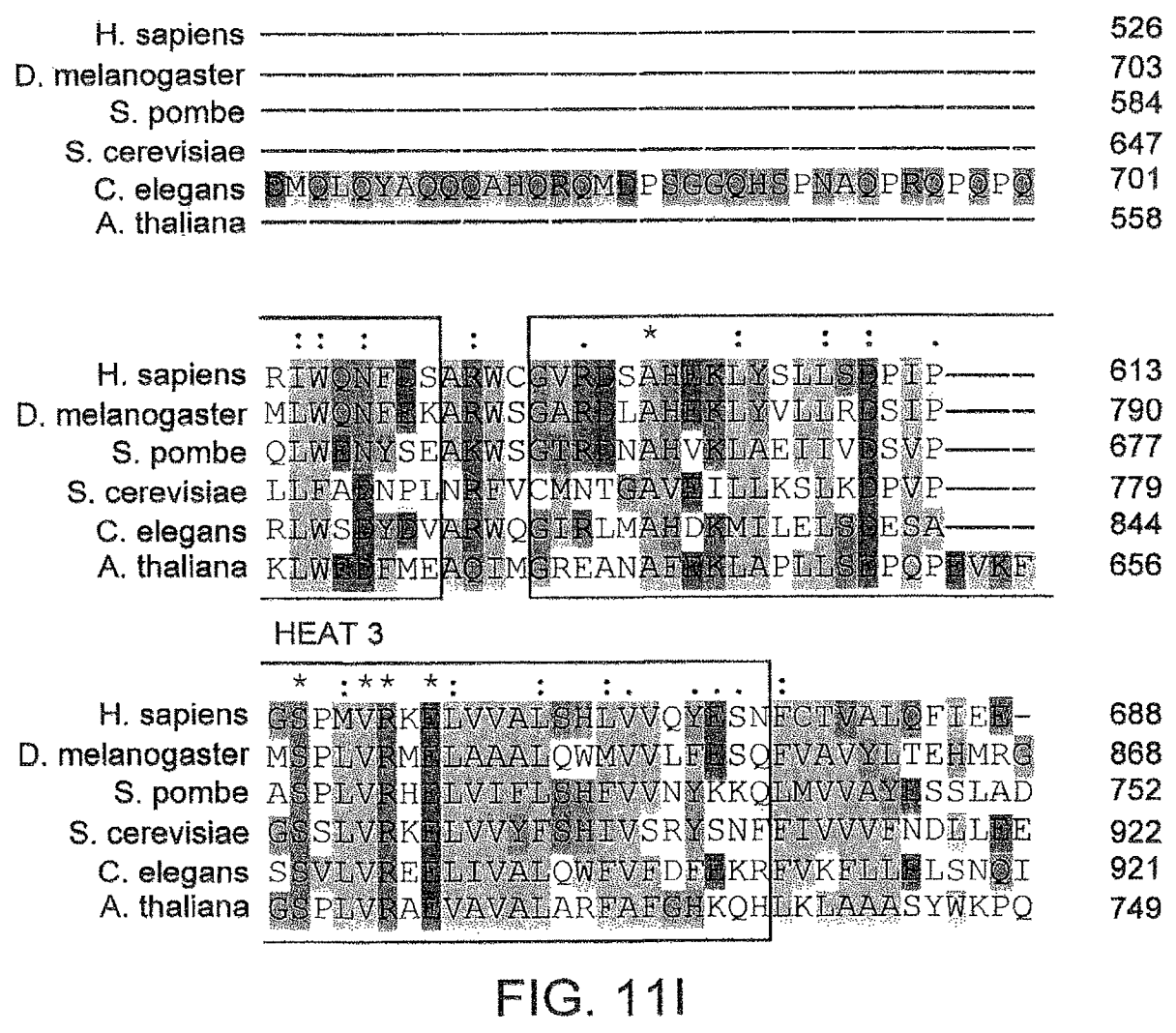

FIGS. 11A-11I show a sequence alignment of full-length sequences of raptor homologues *H. sapiens* (SEQ ID NO: 2), *D. melanogaster* (SEQ ID NO: 21), *S. pombe* (SEQ ID NO: 22), *S. cerevisiae* (SEQ ID NO: 23), *C. elegans* (SEQ ID NO: 24), and *A. thaliana* (SEQ ID NO: 25). Sequences were aligned with ClustalX v1.81 (Thompson et al., *Nucleic Acids Res.* 25:4876-82 (1997)) using the Gonnet series weight matrix. Both pairwise gap opening and gap extension penalties were set at 10.00 and 0.10, respectively. Multiple alignment gap opening and gap extension penalties were set at 10.00 and 0.20. Black boxes frame regions of sequence similarity. Three sequence blocks were found to be common among all six sequences, as described in FIGS. 4A-4C. Three HEAT and seven WD40-like repeats were aligned between most of the sequences. However, alignment of several of the repeats did require minor manual adjustments.

Figure 12:
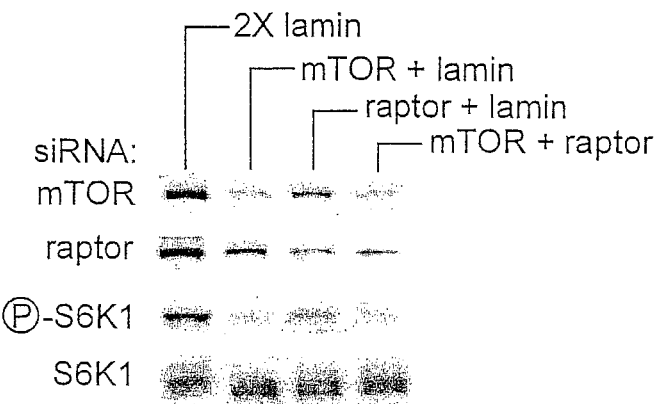

FIG. 12 is a gel showing that transfections into the same cells of the siRNAs targeting both mTOR and raptor do not have additive effects on the phosphorylation state of S6K1. Experiment was performed and analyzed as in FIG. 7C except that each plate was transfected with equal amounts of the two indicated siRNAs. For the negative control twice the total amount of lamin siRNA was used (2× lamin).

Figure 13:
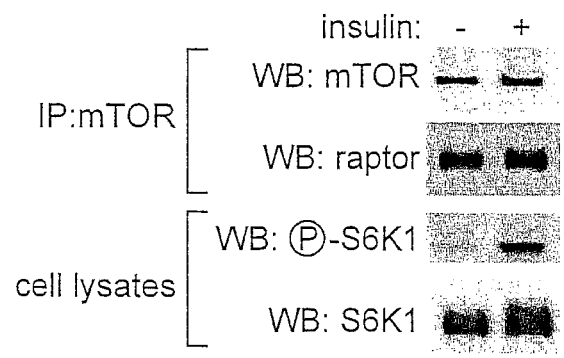

FIG. 13 is a gel showing that stimulation with insulin (200 nM for 25 minutes) of HEK293T cells cultured in serum-free media for 24 hours does not affect the mTOR-raptor association but does increase the phosphorylation level of S6K1. The amounts of mTOR and raptor in mTOR immunoprecipitates, and the in vivo phosphorylation state of S6K1 were analyzed as in FIG. 8A.

Figure 14:
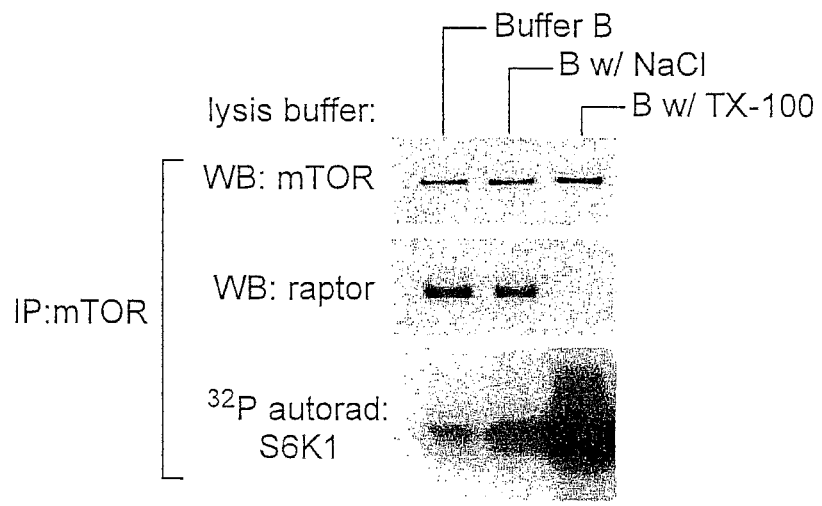

FIG. 14 is a gel showing that cell lysis conditions that destabilize the mTOR-raptor interaction increase mTOR kinase activity. mTOR kinase activity was determined in mTOR immunoprecipitates prepared from cells lysed in unmodified Buffer B (see methods), or Buffer B with 200 mM NaCl (B w/NaCl), or with 0.5% Triton X-100 (B w/TX-100). Although the amounts of mTOR are the same in all the immunoprecipitates (top panel), there is an inverse correlation between the levels of raptor (middle panel) and mTOR kinase activity (bottom panel).

DETAILED DESCRIPTION OF THE INVENTION

The present invention is based, at least in part, on the discovery that in vivo mTOR exists as a complex with one or more regulatory subunits that are lost during isolation of mTOR for in vitro assays. As shown herein, several lines of evidence support the notion that mTOR associates with other proteins: mTOR contains HEAT repeats, which are known protein-protein interaction domains; it migrates at a disproportionately large apparent molecular weight (1.5-2.0 mDa) in gel filtration chromatography; and the expression in transfected cells of mTOR fragments lacking the catalytic site has dominant negative effects on the pathway. However, conventional biochemical attempts to purify mTOR-interacting proteins have been fruitless, since, as shown herein mTOR-containing complexes are unstable under standard purification conditions.

As described herein, a purification scheme that uses a reversible chemical cross-linker to stabilize putative mTOR-containing complexes was devised. Using this strategy, raptor (Regulatory Associated Protein of mTOR), a protein that is required for nutrient signaling to S6K1 and for control of cell growth, has been discovered. The mTOR-raptor interaction also regulates the kinase activity of mTOR and is sensitive to conditions, such as nutrient availability, that signal through the pathway. Thus, provided herein is a mechanism for how nutrients regulate mTOR activity in vivo. Although rapamycin has been generally regarded as mimicking the effects of nutrient deprivation, it was found that the two conditions have opposite effects on the mTOR-raptor interaction.

As shown herein, in vivo mTOR exists in a stoichiometric complex with raptor, a novel, evolutionarily conserved protein that plays at least two roles in the mTOR pathway. Raptor is required for mTOR protein expression, nutrient-stimulated signaling to the downstream effector S6K1, and maintenance of cell size. The association of raptor with mTOR also negatively regulates the mTOR kinase activity. Conditions that repress the pathway, such as nutrient deprivation and mitochondrial uncoupling, stabilize the mTOR-raptor association and inhibit the kinase activity. Overexpression of wild-type raptor mimics nutrient deprivation, causing the formation of a stable mTOR-raptor complex with decreased mTOR kinase activity. Thus, raptor is a missing component of the TOR pathway that through its association with mTOR adjusts the rate cell of growth to nutrient levels.

Accordingly, the present invention relates to isolated raptor nucleic acid molecules of mammalian origin (e.g., human, murine (rat, mouse), bovine, feline, canine) and complements, portions and variants thereof. The present invention also relates to isolated raptor polypeptides of mammalian origin and portions thereof, and antibodies or antigen binding fragments thereof that specifically bind a raptor polypeptide. The present invention also relates to constructs and host cells comprising the nucleic acid molecules described herein. In addition, the present invention relates to uses of the nucleic acid and polypeptide molecules provided herein.

In one embodiment, the present invention relates to an isolated nucleic acid sequence comprising SEQ ID NO: 1. In another embodiment, the isolated nucleic acid molecule encodes an amino acid sequence comprising SEQ ID NO: 2. The Genbank Accession number for the human raptor cDNA is AY090663

As used herein "nucleic acid molecule" includes DNA (e.g., cDNA, genomic DNA, a gene), RNA (e.g., mRNA) and analogs thereof. The nucleic acid molecule can be single stranded or double stranded and can be the coding strand (sense strand) or the noncoding strand (antisense strand). The nucleic acid can include all or a portion of the coding strand and can further comprise additional non-coding sequences such as introns and non-coding 5' and 3' sequences (e.g., regulatory sequences).

An "isolated" nucleic acid molecule indicates that the nucleic acid molecule is in a form that is distinct from the form in which it occurs in nature. Isolated nucleic acid molecules of the present invention are separated from other nucleic acid molecules which are present in its natural state (e.g., free of sequences which normally flank the nucleic acid in the genome of the organism from which it is derived). In one embodiment, the isolated nucleic acid molecule is part of a composition (e.g., a crude extract). In another embodiment, the isolated nucleic acid molecule is substantially free from the cellular material in which it occurs, and in yet another embodiment, the isolated nucleic acid molecule is purified to homogeneity. Various methods, such as gel electrophoresis or chromatography can be used to identify nucleic acid molecules that are substantially free from cellular materials or purified to homogeneity.

A nucleic acid molecule of the present invention can be isolated using standard recombinant or chemical methods and the sequences provided herein. For example, using all or a portion of SEQ ID NO: 1 as a hybridization probe, a raptor sequence can be isolated using standard hybridization and cloning methods (Sambrook et al., eds., *Molecular Cloning: A Laboratory Manual*, $2^{nd}$ ed., Cold Spring Harbor Laboratory, Cold Spring Harbor Laboratory Press, Cold Spring Harbor, N.Y., 1989). A nucleic acid of the invention can be amplified using cDNA, mRNA or genomic DNA as a template and appropriate primers according to standard polymerase chain reaction (PCR) methodology. The amplified nucleic acid can then be cloned into an appropriate vector and characterized using DNA sequence analysis. Raptor nucleic acids can also be prepared using, for example, an automated DNA synthesizer.

In another embodiment, the invention relates to an isolated nucleic acid molecule which is the complement of SEQ ID NO:1 or a portion thereof. A complement of SEQ ID NO: 1 is a sequence which is sufficiently complementary so that it hybridizes to SEQ ID NO: 1, thereby forming a stable duplex. In a particular embodiment, the complement hybridizes to SEQ ID NO: 1 and encodes a raptor polypeptide.

The nucleic acid molecule of the invention can comprise a portion of a nucleic acid sequence encoding raptor. In one embodiment, the portion is a fragment that can be used as a probe or primer. In another embodiment, the portion encodes a biologically active portion of a raptor protein. The portion of a nucleic acid sequence encoding raptor can include all or a portion of the raptor coding sequence and can further include non-coding sequences such as introns and 5' and 3' sequences (e.g., regulatory sequences). The nucleotide sequence determined from the cloning of the human raptor gene allows for the generation of probes and primers designed for use in identifying and/or cloning raptor homologues in other cell types, e.g., from other tissues, as well as raptor homologues from other mammals. The portion (e.g., probe/primer) can comprise a substantially purified raptor oligonucleotide. The portion is generally of a length and composition that hybridizes to all or a characteristic portion of a nucleic acid sequence under stringent conditions. The portion typically comprises a region of nucleotide sequence that hybridizes under stringent conditions to at least about 10, and more particularly about 25, 50, 100, 150, 200, 250, 300, 350, 400, 450, 500, 550 or 1000 contiguous nucleotides of the sense or anti-sense sequence of SEQ ID NO:1 or of a naturally occurring mutant of SEQ ID NO:1.

Probes based on the human raptor nucleotide sequence can be used to detect transcripts or genomic sequences encoding the same or identical proteins, or splice variants or polymorphisms of raptor. A label group (e.g., a radioisotope, a fluorescent compound, an enzyme) can be attached to the probe. Such probes can be used as a part of a diagnostic test kit to assess expression (e.g., aberrant expression) of a raptor protein in a cell or tissue sample by measuring a level of a raptor-encoding nucleic acid in a sample from an individual (e.g., detecting raptor mRNA levels or determining whether a genomic raptor gene has been mutated or deleted). For example, a nucleic acid fragment of the raptor nucleic acid sequence that can be used as a probe or primer includes the raptor N-terminal conserved (RNC) domain and/or one or more of the WD40 repeats.

A nucleic acid fragment encoding a "biologically active portion of raptor" can be prepared by isolating a portion of SEQ ID NO:1 which encodes a polypeptide having a raptor biological activity, expressing the encoded portion of raptor protein (e.g., by recombinant expression in vitro) and assessing the activity of the encoded portion of raptor. A biologically active portion of raptor includes portion which, for example, interact with mTOR, participate in nutrient signaling, participate in maintenance of cell size and negatively regulate the mTOR kinase activity.

The invention further encompasses nucleic acid molecules that differ from the nucleotide sequence of SEQ ID NO:1 due to degeneracy of the genetic code and thus encode the same raptor protein as that encoded by the nucleotide sequence shown in SEQ ID NO:1. For example, the present invention relates to nucleic acid sequence polymorphisms that lead to changes in the amino acid sequences of raptor which exist within a population (e.g., the human population). Such genetic polymorphism in the raptor gene may exist among individuals within a population due to natural allelic variation. As used herein, the terms "gene" and "recombinant gene" refer to nucleic acid molecules comprising an open reading frame encoding a raptor polypeptide (e.g., a mammalian raptor polypeptide). Such nucleotide variations and resulting amino acid polymorphisms in raptor that are the result of natural allelic variation and that do not alter the functional activity of raptor are within the scope of the invention.

Moreover, nucleic acid molecules encoding raptor proteins from other species (raptor homologues), which have a nucleotide sequence which differs from that of a human raptor, are within the scope of the invention. Nucleic acid molecules corresponding to natural allelic variants and homologues of the raptor cDNA of the invention can be isolated based on their identity to the human raptor nucleic acids disclosed herein using the human cDNAs, or a portion thereof, as a hybridization probe according to standard hybridization techniques under stringent hybridization conditions. In one embodiment, the nucleic acid molecule of the present invention comprises a nucleotide sequence that is at least about 50%, 60%, 70%, 75%, 80%, 85%, 90%, 95% or 99% identical to SEQ ID NO: 1 or a complement thereof.

Accordingly, in another embodiment, an isolated nucleic acid molecule of the invention is at least about 100, 150, 200, 250, 300, 350, 400, 450, 500, 550, 600, 650, 700, 800, 900, 1000 or 1300 nucleotides in length and hybridizes under stringent conditions to the nucleic acid molecule comprising the nucleotide sequence, and in a particular embodiment the coding sequence, of SEQ ID NO:1 or the complement thereof. In one embodiment, the nucleic acid molecule hybridizes to the coding sequence of SEQ ID NO: 1. In a particular embodiment, the nucleic acid molecule hybridizes to SEQ ID NO: 1 and encodes a raptor polypeptide.

As used herein, the term "hybridizes under stringent conditions" is intended to describe conditions for hybridization and washing under which nucleotide sequences at least 60%, 65%, 70%, 75%, 80%, 85%, 90%, 95% or 99% identical to each other typically remain hybridized to each other. Such stringent conditions are known to those skilled in the art and can be found in Current Protocols in Molecular Biology, John Wiley & Sons, N.Y. (1989), 6.3.1-6.3.6. One example of stringent hybridization conditions is hybridization in 6× sodium chloride/sodium citrate (SSC) at about 45° C., followed by one or more washes in 0.2×SSC, 0.1% SDS at 50-65° C. In one embodiment, an isolated nucleic acid molecule of the invention that hybridizes under stringent conditions to the sequence of SEQ ID NO:1 corresponds to a naturally-occurring nucleic acid molecule. As used herein, a "naturally-occurring" nucleic acid molecule refers to a nucleic acid molecule having a nucleotide sequence that occurs in nature (e.g., encodes a natural protein).

In addition to naturally-occurring allelic variants of the raptor sequence that may exist in the population, it is known in the art that changes can be introduced by mutation into the nucleotide sequence of SEQ ID NO:1, thereby leading to changes in the amino acid sequence of the encoded raptor protein, without altering the functional (biological) ability of the raptor protein. For example, nucleotide substitutions leading to amino acid substitutions at "non-essential" amino acid residues can be made. Alteration of a "non-essential" amino acid residue in the wild-type sequence of raptor (e.g., the sequence of SEQ ID NO:2) will not affect the biological activity of raptor. Conversely, an "essential" amino acid residue is required for biological activity of raptor. Therefore, alteration of an essential amino acid in the wild-type sequence of raptor will affect the biological activity of raptor. Amino acid residues that are conserved among the raptor proteins of various species will likely be essential amino acids. For example, as described herein, several mutations in the RNC or WD40 domains of raptor, generated by changing evolutionarily conserved residues (FIG. 6B), eliminated the interaction with mTOR, whereas other RNC domain mutants, as well as a mutation in the region between the HEAT and WD40 repeats, did not affect it.

In one embodiment, raptor proteins of the present invention, contain at least one RNC domain. Additionally, a raptor protein also contains at least one WD40 repeat. As shown herein, such conserved domains contain essential or conserved amino acids. Other amino acid residues, however, (e.g., those that are not conserved or only semi-conserved among raptor of various species) are likely not essential for activity and thus can be altered without altering the biological activity of raptor.

Accordingly, another aspect of the invention pertains to nucleic acid molecules encoding raptor proteins that contain changes in amino acid residues that are not essential for activity. Such raptor proteins differ in amino acid sequence from SEQ ID NO:2 and retain raptor biological activity (e.g., interaction with mTOR, participation in nutrient signaling, participation in maintenance of cell size and negative regulation of the mTOR kinase activity). In one embodiment, the isolated nucleic acid molecule includes a nucleotide sequence encoding a protein that includes an amino acid sequence that is at least about 45%, 50%, 60%, 75%, 85%, 95%, or 98% identical to the amino acid sequence of SEQ ID NO:2.

An isolated nucleic acid molecule encoding a raptor protein having a sequence which differs from that of SEQ ID NO:2 can be created by introducing one or more nucleotide substitutions, additions or deletions into the nucleotide sequence of raptor nucleic acid molecule (SEQ ID NO:1) such that one or more amino acid substitutions, additions or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. A predicted nonessential amino acid residue in raptor is preferably replaced with another amino acid residue from the same side chain family. Alternatively, mutations can be introduced randomly along all or part of a raptor coding sequence, and the resultant mutants can be screened for raptor biological activity to identify mutants that retain activity. Following mutagenesis, the encoded protein can be expressed recombinantly and the activity of the protein can be determined using methods described herein.

In a preferred embodiment, a mutant Raptor protein can be assayed for the ability to interact with mTOR, participate in nutrient signaling, participate in maintaining cell size and negatively regulate the mTOR kinase activity.

The present invention also encompasses antisense nucleic acid molecules, i.e., molecules which are complementary to a sense nucleic acid encoding a raptor polypeptide, e.g., complementary to the coding strand of a double-stranded cDNA raptor molecule or complementary to an mRNA raptor sequence. The antisense nucleic acid can be complementary to an entire raptor coding strand, or to only a portion thereof, e.g., all or part of the protein coding region (or open reading frame). An antisense nucleic acid molecule can be antisense to a noncoding region of the coding strand of a nucleotide sequence encoding raptor. The noncoding regions (5' and 3' untranslated regions) are the 5' and 3' sequences which flank the coding region and are not translated into amino acids. The antisense nucleic acid molecule can be complementary to the entire coding region of raptor mRNA, but more preferably is an oligonucleotide which is antisense to only a portion of the coding or noncoding region of raptor mRNA. An antisense oligonucleotide can be, for example, about 5, 10, 15, 20, 25, 30, 35, 40, 45 or 50 nucleotides in length. An antisense nucleic acid of the invention can be constructed using procedures known in the art (e.g., using chemical synthesis and enzymatic ligation reactions).

The invention also relates to isolated raptor protein or polypeptides, and portions (e.g., biologically active portions) thereof. An "isolated" or "purified" (e.g., partially or substantially) polypeptide or biologically active portion thereof is in a form that is distinct from the form in which it occurs in nature. In one embodiment, the polypeptide is part of a composition (crude extract). In another embodiment, the polypeptide is substantially free of cellular material or other contaminating proteins from the cell or tissue source from which the raptor protein is derived, or substantially free from chemical precursors or other chemicals when chemically synthesized. The language "substantially free of cellular material" includes preparations of raptor protein in which the protein is separated from cellular components of the cells from which it is isolated, recombinantly produced or chemically synthesized. Such preparations of raptor protein have less than about 30%, 20%, 10%, 5% (by dry weight) of chemical precursors or non-raptor chemicals. Various methods, such as gel electrophoresis or chromatography can be used to identify polypeptides that are substantially free of cellular material. In one embodiment, the present invention relates to an isolated polypeptide encoded by a nucleic acid comprising SEQ ID NO:1. In another embodiment, the present invention relates to an isolated polypeptide having an amino acid sequence comprising SEQ ID NO: 2.

The present invention also relates to portions of a raptor polypeptide. In one embodiment, the portions are biologically active portions of a raptor protein and include peptides comprising amino acid sequences sufficiently identical to or derived from the amino acid sequence of the raptor protein (e.g., the amino acid sequence shown in SEQ ID NO:2). Biologically active portions include a portion of the full length raptor proteins, and exhibit at least one activity of a raptor protein (e.g., interaction with mTOR, participation in nutrient signaling, participation in maintenance of cell size and negative regulation of the mTOR kinase activity). Typically, biologically active portions comprise one or more domains or regions with at least one activity of the raptor protein. A biologically active portion of a raptor protein can be a polypeptide which is, for example, at least about 10, 25, 50, 100, 200, 300, 400, 500, 600, 700, 800, 900, 1000 or more amino acids in length. Biologically active polypeptides include one or more identified raptor domains, e.g., RNC domain. Other biologically active portions can be prepared by recombinant techniques and evaluated for one or more of the functional activities of a native raptor protein.

Other raptor polypeptides of the present invention are substantially identical to SEQ ID NO:2, retain the functional activity of the protein of SEQ ID NO:2, yet differ in amino acid sequence due to natural allelic variation or mutagenesis. Raptor is involved in nutrient signaling and cell growth. Accordingly, a useful raptor polypeptide includes an amino acid sequence at least about 45%, preferably 55%, 65%, 75%, 85%, 95%, or 99% identical to the amino acid sequence of SEQ ID NO:2 and retains the functional activity of the raptor polypeptide of SEQ ID NO:2. In other instances, the raptor polypeptide has an amino acid sequence 55%, 65%, 75%, 85%, 95%, or 98% identical to the raptor RNC domain. In one embodiment, the raptor polypeptide retains a functional activity of the Raptor protein of SEQ ID NO:2.

To determine the percent identity of two amino acid sequences or of two nucleic acids, the sequences are aligned for optimal comparison purposes, wherein gaps are introduced in the sequences being compared. The amino acid residues at corresponding amino acid positions or nucleotides at corresponding nucleotide positions are then compared. When a position in a first sequence is occupied by the same amino acid residue or nucleotide as the corresponding position in a second sequence, then the molecules are identical at that position. The percent identity between the two sequences is a function of the number of identical positions shared by the sequences (e.g., % identity=# of identical positions/total # of positions×100).

As described herein, the determination of percent homology between two sequences can be accomplished using a mathematical algorithm. Examples of a mathematical algorithm utilized for the comparison of two sequences is the algorithm of Karlin and Altschul (1993) *Proc. Nat'l Acad. Sci. USA* 90: 5873-5877 and the algorithm incorporated into the NBLAST and XBLAST programs of Altschul, et al. (1990) *J. Mol. Biol.* 215:403-410. Another example of a mathematical algorithm utilized for the comparison of sequences is the algorithm of Myers and Miller, CABIOS (1989).

Native raptor polypeptides can be isolated from cells or tissue sources using the purification schemes described herein. In one embodiment, the present invention relates to a method of identifying proteins that associate with mTOR within a cell comprising contacting a lysate of the cell with a reversible crosslinker (e.g., dithiobis(succinmidylpropionate) (DSP)) thereby forming a crosslink between proteins that associate within the cell. Proteins that are associated by the crosslink from the lysate are then separated, thereby identifying proteins that associate within a cell. The method can further comprising reducing the crosslink (e.g., using a reducing agent such as dithiothreitol) between the proteins and isolating the proteins. In addition, the method can further comprise separating the proteins that are associated by the crosslink from the lysate using an antibody that specifically binds one of the proteins.

The present invention also relates to a method of identifying proteins that associate with mTOR within a cell, comprising preparing a lysate of the cell with a buffer comprising a detergent other than Triton, thereby preserving an association between the proteins. The proteins that are associated are separated from the lysate, thereby identifying proteins that associate within a cell under conditions in which a crosslinker is not used. The method can further comprising isolating the proteins that are associated from one another. In one embodiment, the buffer comprises CHAPS at a concentration from about 0.05% to about 2% CHAPS. In a particular embodiment, the buffer comprises about 0.3% CHAPS. In addition, the buffer can further comprise 120 mM NaCl. In another embodiment, the method of identifying proteins that associate with mTOR within a cell is performed without the use of a crosslinker.

The present invention also provides a method of producing raptor polypeptides using recombinant DNA techniques. Alternative to recombinant expression, a raptor protein or polypeptide can be synthesized chemically using standard peptide synthesis techniques.

The invention also provides raptor chimeric or fusion proteins. As used herein, a raptor "chimeric protein" or "fusion protein" comprises a raptor polypeptide fused in-frame to an additional component (a non-raptor polypeptide). Within a raptor fusion protein, the raptor polypeptide can correspond to all or a portion of a raptor protein, preferably at least one biologically active portion of a raptor protein. The additional component can be fused to the N-terminus or C-terminus of the raptor polypeptide. An example of a fusion protein is a GST-raptor fusion protein in which the raptor sequences are fused to the C-terminus of the GST sequences. Such fusion proteins can facilitate the purification of recombinant raptor. Another example of a fusion protein is a raptor-immunoglobulin fusion protein in which all or part of raptor is fused to sequences derived from a member of the immunoglobulin protein family. The raptor-immunoglobulin fusion proteins of the invention can be used as immunogens to produce anti-raptor antibodies in a subject, to purify raptor ligands and in screening assays to identify molecules which inhibit the interaction of raptor with a raptor ligand (e.g., mTOR).

A raptor chimeric or fusion protein of the invention can be produced by standard recombinant DNA techniques. For example, DNA fragments coding for the different polypeptide sequences are ligated together in-frame in accordance with conventional techniques (e.g., using blunt-ended or staggered-ended termini for ligation, restriction enzyme digestion, and enzymatic ligation). In another embodiment, conventional techniques such as an automated DNA synthesizer can be used. Alternatively, PCR amplification of gene fragments can be carried out using anchor primers which give rise to complementary overhangs between two consecutive gene fragments which can subsequently be annealed and reamplified to generate a chimeric gene sequence (see, e.g., Current Protocols in Molecular Biology, Ausubel et al. eds., John Wiley & Sons: 1992). Moreover, many expression vectors are commercially available that already encode a fusion moiety (e.g., a GST polypeptide). A raptor-encoding nucleic acid can be cloned into such an expression vector such that the fusion moiety is linked in-frame to the raptor protein.

The present invention also pertains to variants of raptor proteins or polypeptides which function as either raptor agonists (mimetics) or as raptor antagonists. Variants of the raptor protein can be generated by mutagenesis (e.g., discrete point mutation or truncation of the raptor protein).

Variants of the raptor polypeptide which function as either raptor agonists or as raptor antagonists can be identified by screening combinatorial libraries of mutants, e.g., truncation mutants of the raptor polypeptide for raptor polypeptide agonist or antagonist activity. There are a variety of methods which can be used to produce libraries of potential raptor variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes provides, in one mixture, of all of the sequences encoding the desired set of potential raptor sequences. Methods for synthesizing degenerate oligonucleotides are known in the art (see, e.g., Narang (1983) *Tetrahedron* 39:3; Itakura et al. (1984) *Annu. Rev. Biochem.* 53:323; Itakura et al. (1984) *Science* 198: 056; Ike et al. (1983) *Nucleic Acid Res.* 11:477). Several techniques are known in the art for screening gene products of combinatorial libraries made by point mutations or truncation, and for screening cDNA libraries for gene products having a selected property (e.g., a biased library).

The present invention also relates to an antibody or antigen binding fragment thereof that specifically binds to a mammalian raptor polypeptide. In one embodiment, the antibody or antigen binding fragment thereof specifically binds to mammalian raptor polypeptide encoded by an isolated nucleic acid that encodes SEQ ID NO: 2. In another embodiment, the antibody or antigen binding fragment thereof specifically binds to mammalian raptor polypeptide comprising SEQ ID NO: 2. An isolated raptor protein, or a portion or fragment thereof, can be used as an immunogen to generate antibodies that bind raptor using standard techniques for polyclonal and monoclonal antibody preparation. The full-length raptor protein or antigenic peptide fragments of the raptor protein can be used as immunogens. For example, an antigenic peptide of raptor can comprise at least about 10, 12, 15, 20, 30, 50 or 100 amino acid residues of the amino acid sequence shown in SEQ ID NO:2 and encompass an epitope of raptor such that an antibody raised against the peptide forms a specific immune complex with raptor. Particular epitopes encompassed by the antigenic peptide are regions of raptor that are located on the surface of the protein, e.g., hydrophilic regions.

Generally, a suitable subject, (e.g., rabbit, goat, mouse, rat, hamster or other mammal) is immunized with a raptor immunogen to prepare antibodies or antigen binding fragments thereof that specifically bind raptor. The raptor immunogen can further include an adjuvant, such as Freund's complete or incomplete adjuvant, or similar immunostimulatory agent. Immunization of a suitable subject with an immunogenic raptor preparation induces a polyclonal anti-raptor antibody response.

A molecule which specifically binds to raptor is a molecule which binds raptor, but does not substantially bind other molecules in a sample, e.g., a biological sample, which contains raptor. As used herein "antibody" includes full length antibodies or immunoglobulin molecules and immunologically active portions of immunoglobulin molecules. Immunologically active portions of immunoglobulin molecules include, for example, F(ab) and F(ab')$_2$ fragments which can be generated by treating the antibody with an enzyme such as pepsin. The term "antibody" also includes polyclonal and monoclonal antibodies that bind raptor.

Polyclonal anti-raptor antibodies can be prepared as described above by immunizing a suitable subject with a raptor immunogen. The antibody molecules directed against raptor can be isolated from the mammal (e.g., from the blood) and further purified by well-known techniques (e.g., protein A chromatography). In addition, antibody-producing cells can be obtained from the subject and used to prepare monoclonal antibodies by standard techniques, such as the hybridoma technique originally described by Kohler and Milstein (1975) *Nature* 256:495-497. The technology for producing various antibodies monoclonal antibody hybridomas is well known (see generally Current Protocols in Immunology (1994) Coligan et al. (eds.) John Wiley & Sons, Inc., New York, N.Y.). A monoclonal anti-raptor antibody can also be identified and isolated by screening a recombinant combinatorial immunoglobulin library (e.g., an antibody phage display library) with raptor to thereby isolate immunoglobulin library members that bind raptor. Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612).

The term "antibody" also includes chimeric and humanized monoclonal antibodies, comprising both human and non-human portions, which can be made using standard recombinant DNA techniques. Such chimeric and humanized monoclonal antibodies can be produced by recombinant DNA techniques known in the art.

An anti-raptor antibody (e.g., monoclonal antibody) can be used to isolate raptor by standard techniques, such as affinity chromatography or immunoprecipitation. An anti-raptor antibody can facilitate the purification of natural raptor from cells, recombinantly produced raptor expressed in host cells and chemically synthesized raptor. Moreover, an anti-raptor antibody can be used to detect raptor protein in a sample (e.g., in a cellular lysate or cell supernatant) and also to evaluate the quantity and expression pattern of the raptor protein. Anti-raptor antibodies can be used diagnostically to monitor protein levels in tissue as part of a clinical testing procedure (e.g., to determine the efficacy of a given treatment regimen). A detectable substance or tag can be coupled to the antibody to facilitate detection. Examples of detectable substances include enzymes, prosthetic groups, fluorescent materials, luminescent materials, bioluminescent materials, and radioactive materials.

The present invention also provides expression constructs (expression vectors) containing a nucleic acid encoding a raptor polypeptide or a portion thereof. Examples of vectors include plasmids and viral vector (e.g., replication defective retroviruses, adenoviruses and adeno-associated viruses).

The expression constructs of the invention comprise a raptor nucleic acid of the invention operably linked to one or more regulatory sequences. In one embodiment, the expression construct comprises SEQ ID NO: 1. The regulatory sequence is selected based on the vector and host cell used for expression of raptor. As used herein "operably linked" indicates that the raptor nucleic acid is linked to the regulatory sequence(s) in a manner which allows for expression of the nucleotide sequence (e.g., in an in vitro transcription/translation system or in a host cell when the vector is introduced into the host cell). As used herein, a "regulatory sequence" includes promoters, enhancers and other expression control elements such as polyadenylation signals which direct constitutive expression or tissue-specific expression of a nucleic acid. Such regulatory sequences are described, for example, in Goeddel; Gene Expression Technology: Methods in Enzymology 185, Academic Press, San Diego, Calif. (1990). The vector used in the present invention depends on several factors such as the choice of the host cell to be transformed, the level of expression of protein desired, etc. When introduced into a host cell the vectors of the invention can be used to produce raptor proteins or peptides, including fusion proteins or peptides, encoded by nucleic acids as described herein (e.g., raptor proteins, mutant forms of raptor, fusion proteins).

The vectors of the invention can be designed for expression of raptor in prokaryotic or eukaryotic cells, e.g., bacterial cells such as *E. coli*, insect cells (using baculovirus expression vectors), yeast cells or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase. The vectors described herein can also comprise a nucleic acid molecule of the invention cloned into the vector in an antisense orientation.

Another aspect of the invention pertains to host cells into which an expression vector of the invention has been introduced (recombinant cells). In one embodiment, a host cell of the present invention comprises a nucleic acid molecule that encodes the amino acid sequence of SEQ ID NO: 2. The term "host cell" refers to the particular subject cell and to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be a prokaryotic or eukaryotic cell. For example, raptor protein can be expressed in bacterial cells (e.g., *E. coli*), insect cells, yeast cells or mammalian cells (e.g., Chinese hamster ovary cells (CHO) or COS cells). Other suitable host cells are known to those skilled in the art.

Vector DNA can be introduced into prokaryotic or eukaryotic cells using a variety of art-recognized techniques for introducing foreign nucleic acid (e.g., DNA) into a host cell. For example, calcium phosphate or calcium chloride co-precipitation, DEAE-dextran-mediated transfection, lipofection, or electroporation can be used. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. Optionally, a selectable marker (e.g., resistance to antibiotics) can be introduced into the host cells along with the nucleic acid encoding raptor to identify and select cells that include the nucleic acid. Examples of selectable markers include G418, hygromycin and methotrexate. Nucleic acid encoding a selectable marker can be introduced into a host cell on the same vector as that encoding raptor or can be introduced on a separate vector.

A host cell of the invention, such as a prokaryotic or eukaryotic host cell in culture, can be used to produce a (i.e., express) raptor polypeptide. Accordingly, the invention further provides methods for producing a raptor polypeptide using the host cells of the invention. In one embodiment, the method comprises culturing the host cell comprising nucleic acid encoding a raptor polypeptide or portion thereof under conditions in which (e.g., in a suitable medium) raptor polypeptide is produced. In another embodiment, the method further comprises isolating raptor polypeptide from the medium or the host cell. The present invention also relates to the isolated raptor polypeptide.

The raptor nucleic acid molecules, raptor proteins, and anti-raptor antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein, a "pharmaceutically acceptable carrier" includes solvents, dispersion media, coatings, antibacterial and antifungal agents, isotonic and absorption delaying agents, and the like, compatible with pharmaceutical administration. The use of such media and agents for pharmaceutically active substances is well known in the art.

A pharmaceutical composition of the invention is formulated to be compatible with its intended route of administration. Examples of routes of administration include parenteral, e.g., intravenous, intradermal, subcutaneous, oral, intranasal, transdermal (topical), transmucosal, and rectal administration (e.g., suppositories). The pharmaceutical compositions of the present invention can also include a sterile diluent such as water for injection, saline solution, fixed oils, polyethylene glycols, glycerine, propylene glycol or other synthetic solvents; antibacterial agents; antioxidants; chelating agents; buffers and agents for the adjustment of tonicity. The can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline or phosphate buffered saline (PBS). The carrier can be a solvent or dispersion medium containing, for example, water, ethanol and polyol (e.g., glycerol, propylene glycol). In addition, a coating (e.g., lecithin) or a surfactant can be used. Antibacterial and antifungal agents, (e.g., thimerosal) can also be included. Moreover, sugars, polyalcohols and sodium chloride can be included in the pharmaceutical composition. An agent which delays absorption, for example, aluminum monostearate and gelatin can also be used.

Oral compositions can include an inert diluent or an edible carrier and can be in the form of capsules (e.g., gelatin), pills or tablets. The tablets, pills or capsules, can contain a binder, an excipient, a lubricant, a sweetening agent or a flavoring agent. For administration by inhalation, the compounds are delivered in the form of an aerosol spray from pressured container or dispenser which contains a suitable propellant, e.g., a gas such as carbon dioxide, or a nebulizer.

In one embodiment, the active compounds can be administered as a controlled release formulation, including implants and microencapsulated delivery systems (e.g., biodegradable, biocompatible polymers can be used). Methods for preparation of such formulations will be apparent to those skilled in the art. The materials can also be obtained commercially.

The dosage of the pharmaceutical compositions of the invention depend on the unique characteristics of the active compound and the particular therapeutic effect to be achieved, and the limitations inherent in the art of compounding such an active compound for the treatment of individuals.

The pharmaceutical compositions can be included in a kit, container, pack, or dispenser together with instructions for administration.

The nucleic acid molecules, proteins, protein homologues, and antibodies described herein can be used in a variety of methods.

The isolated nucleic acid molecules of the invention can be used to express raptor protein (e.g., via a recombinant expression vector in a host cell), to detect raptor mRNA (e.g., in a biological sample) and to modulate raptor activity. In addition, the raptor proteins can be used to screen drugs or compounds which modulate the raptor activity or expression as well as to treat disorders characterized by a decreased or excessive production of raptor protein or production of raptor protein forms which have decreased or aberrant activity compared to raptor wild type protein. In addition, the anti-raptor antibodies of the invention can be used to detect and isolate raptor proteins and modulate raptor activity. This invention further pertains to novel agents identified by the above-described screening assays and their use for treatments as described herein.

Another aspect of the present invention relates to diagnostic assays for determining raptor polypeptide and/or nucleic acid expression as well as raptor activity, in the context of a biological sample (e.g., blood, serum, cells, tissue) to thereby determine whether an individual is afflicted with a disease or disorder, or is at risk of developing a disorder, associated with aberrant raptor expression or activity. The invention also provides for determining whether an individual is at risk of developing a disorder associated with raptor protein, nucleic acid expression or activity. For example, mutations in a raptor gene can be assayed in a biological sample. Such assays can be used for prognostic or predictive purpose to prophylactically treat an individual prior to the onset of a disorder characterized by or associated with raptor protein, nucleic acid expression or activity (e.g., cancer).

The present invention also pertains to a method for detecting the presence or absence of raptor in a sample (e.g., a biological sample) comprising contacting a sample with a compound or an agent capable of detecting raptor protein or nucleic acid (e.g., mRNA, genomic DNA) that encodes raptor protein such that the presence of raptor is detected in the sample. The method can further comprise obtaining the sample. In one embodiment, a labeled nucleic acid sequence (probe) capable of hybridizing to raptor mRNA or genomic DNA is used to detect raptor nucleic acid (e.g., mRNA or genomic DNA). The nucleic acid sequence can be, for example, a full-length raptor nucleic acid, such as the nucleic acid of SEQ ID NO: 1 or a portion thereof, such as an oligonucleotide of at least about 10, 20, 30, 50, 100, 350, 500, 1000 or 2000 nucleotides in length and sufficient to specifically hybridize under stringent conditions to raptor nucleic acid. Other suitable probes for use in the diagnostic assays of the invention are described herein.

In another embodiment, an antibody, preferably an antibody with a detectable label, capable of binding to raptor protein or a characteristic portion thereof is used. Thus, the present invention also provides a method of identifying a mammalian raptor polypeptide in a sample comprising contacting the sample with an antibody or antigen binding fragment thereof that specifically binds to a mammalian raptor polypeptide wherein the mammalian raptor polypeptide is encoded by an isolated nucleic acid that encodes SEQ ID NO: 2. The polypeptide which specifically binds to the antibody is identified, thereby identifying a mammalian raptor polypeptide in a sample.

Antibodies can be polyclonal, or more preferably, monoclonal. An intact antibody, or a fragment thereof (e.g., Fab or F(ab')$_2$) can be used. Examples of detectable labels include a fluorescently labeled secondary antibody, and biotin such that it can be detected with fluorescently labeled streptavidin.

A "sample" includes biological samples such as tissues, cells and biological fluids of a subject which contain raptor protein molecules, mRNA molecules or genomic DNA molecules from the test subject. The detection method of the invention can be used to detect raptor mRNA, protein, or genomic DNA in a biological sample in vitro as well as in vivo. For example, in vitro techniques for detection of raptor mRNA include Northern hybridizations and in situ hybridizations. In vitro techniques for detection of raptor protein include enzyme linked immunosorbent assays (ELISAs), Western blots, immunoprecipitations and immunofluorescence. In vitro techniques for detection of raptor genomic DNA include Southern hybridizations. Furthermore, in vivo techniques for detection of raptor protein include introducing into a subject a labeled anti-raptor antibody, wherein the antibody is labeled with a radioactive marker whose presence and location in a subject can be detected by standard imaging techniques.

In another embodiment, the methods further involve obtaining a control sample from a control subject, contacting the control sample with a compound or agent capable of detecting raptor protein, mRNA, or genomic DNA, such that the presence of raptor protein, mRNA or genomic DNA is detected in the biological sample, and comparing the presence of raptor protein, mRNA or genomic DNA in the control sample with the presence of raptor protein, mRNA or genomic DNA in the test sample.

The invention also encompasses kits for detecting the presence of raptor in a sample. Such kits can be used to determine if a subject is suffering from or is at increased risk of developing a disorder associated with aberrant expression of Raptor (e.g., a proliferative cell disorder such as cancer). For example, the kit can comprise a labeled compound or agent capable of detecting raptor protein or mRNA in a sample and means for determining the amount of raptor in the sample (e.g., an anti-raptor antibody or an oligonucleotide probe which binds to DNA encoding Raptor such as SEQ ID NO:1). Kits may also include instruction for observing that the tested subject is suffering from or is at risk of developing a disorder associated with aberrant expression of raptor if the amount of raptor protein or mRNA is above or below a normal level.

For antibody-based kits, the kit may comprise, for example: (1) a first antibody (e.g., attached to a solid support) which binds to raptor protein; and, optionally, (2) a second, different antibody which binds to raptor protein or the first antibody and is conjugated to a detectable agent. For oligonucleotide-based kits, the kit may comprise, for example: (1) a oligonucleotide, e.g., a detectably labelled oligonucleotide, which hybridizes to a raptor nucleic acid sequence or (2) a pair of primers useful for amplifying a raptor nucleic acid molecule.

The kit may also comprise, e.g., a buffering agent, a preservative, or a protein stabilizing agent. The kit may also comprise components necessary for detecting the detectable agent (e.g., an enzyme or a substrate). The kit may also contain a control sample or a series of control samples which can be assayed and compared to the test sample contained along with instructions for observing whether the tested subject is suffering from or is at risk of developing a disorder associated with aberrant expression of raptor.

The invention provides a method (also referred to herein as a "screening assay") for identifying agents that alter raptor expression and/or activity. For example, such agents (modulators) include candidate or test compounds or agents (e.g., peptides, peptidomimetics, small molecules such as small organic molecules or other drugs) which bind to a raptor polypeptide and/or inhibit or enhance (partially, completely) raptor expression or raptor activity. In one embodiment, the ability of an agent to alter raptor expression and/or activity is accomplished by determining the ability of the agent to alter the activity of (e.g., interaction of) raptor with a raptor target molecule. As used herein, a "target molecule" is a molecule with which a raptor protein binds to or interacts with in nature. In one embodiment, a raptor target molecule is mTOR. Thus, the present invention relates to a method of identifying an agent that alters interaction of a mammalian raptor protein with mammalian target of rapamycin (mTOR) protein comprising contacting a raptor protein having an amino acid sequence comprising SEQ ID NO: 2 with mTOR protein under conditions in which the raptor protein interacts with the mTOR protein, with an agent to be assessed. The extent to which raptor interacts with mTOR in the presence of the agent to be assessed is determined, wherein if the extent to which raptor interacts with mTOR is altered in the presence of the agent compared to the extent to which raptor interacts with mTOR in the absence of the agent, then the agent alters interaction of a mammalian raptor protein with mTOR protein.

Determining the ability of the raptor protein to bind to or interact with a raptor target molecule can be accomplished by methods which detect binding directly or indirectly. In one embodiment, determining the ability of the raptor protein to bind to or interact with a raptor target molecule can be accomplished by directly detecting the binding of raptor to the target molecule using, for example, one or more antibodies to detect raptor and/or its target molecule, or gel electrophoresis. In another embodiment, determining the ability of the raptor protein to bind to or interact with a raptor target molecule can be accomplished by determining the activity of raptor and/or the target molecule. For example, the activity of raptor or a raptor target molecule such as mTOR, can be determined by detecting interaction of raptor and mTOR, the ability of mTOR to participate in nutrient signaling, the ability of mTOR to participate in maintenance of cell size and the ability of raptor to negatively regulate the mTOR kinase activity.

In one embodiment, the method comprises contacting a raptor protein or biologically active portion thereof with an agent and determining the ability of the agent to bind to the raptor protein or biologically active portion thereof. Binding of the test compound to the raptor protein can be determined either directly or indirectly. In one embodiment, the assay includes contacting the raptor protein or biologically active portion thereof with a raptor target molecule which binds raptor (e.g., mTOR) to form an assay mixture; contacting the assay mixture with an agent; and determining the ability of the agent to interact with a raptor protein. In this embodiment, the ability of the agent to interact with a raptor protein comprises comparing the extent to which the agent binds to raptor or a biologically active portion thereof, to the extent to which mTOR binds to raptor or a biologically active portion thereof. If raptor preferentially binds the agent as compared to mTOR, then the agent alters raptor expression and/or activity.

In the screening methods of the present invention, the raptor or its target molecule can be immobilized to facilitate separation of complexed from uncomplexed forms of one or both of the proteins, as well as to accommodate automation of the assay. Binding of an agent to raptor, or interaction of raptor with a target molecule in the presence and absence of an agent to be assessed, can be accomplished using, for example, microtitre plates, test tubes, and micro-centrifuge tubes. Examples of methods for immobilizing proteins on matrices include the use of glutathione-S-transferase/raptor fusion proteins or glutathione-S-transferase/target fusion proteins adsorbed onto glutathione sepharose beads (Sigma Chemical; St. Louis, Mo.) or glutathione derivatized microtitre plates and the use biotin and streptavidin conjugation.

In another embodiment, modulators of raptor expression are identified in a method in which a cell is contacted with an agent and the expression of raptor mRNA or protein in the cell is determined. The level of expression of raptor mRNA or protein in the presence of the agent is compared to the level of expression of raptor mRNA or protein in the absence of the agent. The agent can then be identified as a modulator of raptor expression based on this comparison. For example, when expression of raptor mRNA or protein is greater in the presence of the agent than in its absence, the candidate compound is identified as a stimulator of raptor mRNA or protein expression. Alternatively, when expression of raptor mRNA or protein is less in the presence of the agent than in its absence, the candidate compound is identified as an inhibitor of raptor mRNA or protein expression. The level of raptor mRNA or protein expression in the cells can be determined by methods described herein for detecting raptor mRNA or protein.

In another embodiment, the present invention relates to a method of identifying an agent that alters interaction of a mammalian raptor protein with mammalian target of rapamycin (mTOR) protein comprising contacting a cell (e.g., a host cell) which comprises nucleic acid that encodes a raptor protein having an amino acid sequence comprising SEQ ID NO: 2 wherein the raptor protein, when expressed, interacts with mTOR protein in the cell, with an agent to be assessed. The growth rate and/or size of the cell is then determined, wherein an altered growth rate and/or size of the cell compared to growth rate and/or size of a control cell indicates that the agent alters interaction of a mammalian raptor protein with mTOR protein. In one embodiment, the present invention relates to a method of identifying an agent that inhibits an interaction of a mammalian raptor protein with mammalian target of rapamycin (mTOR) protein comprising contacting a cell which comprises nucleic acid that encodes a raptor protein having an amino acid sequence comprising SEQ ID NO: 2 wherein the raptor protein, when expressed, interacts with mTOR protein in the cell, with an agent to be assessed. The growth rate and/or size of the cell is assessed, wherein a decrease in growth rate or size of the cell compared to growth rate and/or size of a control cell indicates that the agent inhibits interaction of a mammalian raptor protein with mTOR protein.

In another embodiment, the invention relates to a method of identifying an agent that enhances an interaction of a mammalian raptor protein with mammalian target of rapamycin (mTOR) protein comprising contacting a cell which comprises nucleic acid that encodes a raptor protein having an amino acid sequence comprising SEQ ID NO: 2 wherein the raptor protein, when expressed, interacts with mTOR protein in the cell, with an agent to be assessed. The growth rate and/or size of the cell is assessed, wherein an increase in growth rate and/or size of the cell compared to growth rate and/or size of a control cell indicates that the agent enhances interaction of a mammalian raptor protein with mTOR protein.

In the methods of the present invention, the growth rate and/or size can be assessed by measuring phosphorylation of a regulator of protein synthesis (e.g., S6 kinase 1, 4E-BP1 and combinations thereof). The growth rate and/or size can also be assessed by measuring binding of the mammalian raptor protein with mTOR protein.

As shown herein, raptor forms a nutrient sensitive complex with mTOR and is necessary for the activity of the mTOR pathway. Specifically, it has been shown that two interactions exist between raptor and mTOR: a 'constitutive' interaction that is required for in vivo mTOR function and a 'nutrient sensitive' interaction that forms in the absence of nutrients and negatively regulates mTOR kinase activity. As also shown herein, growing cells transfected with interfering RNA (siRNA) targeting raptor were reduced in size.

Accordingly, the present invention provides a method of altering the growth and/or size of a cell comprising introducing into the cell an agent that alters interaction of raptor protein with mTOR protein.

In one embodiment, the present invention provides a method of enhancing growth rate and/or size of a cell comprising introducing into the cell an agent that inhibits interaction of mammalian raptor protein with mammalian TOR protein. The agent can be, for example, exogenous nucleic acid that inhibits activity of a mammalian raptor protein. In one embodiment, the exogenous nucleic acid results in overexpression of mammalian raptor protein in the cell. The exogenous nucleic acid can be, for example, mRNA that specifically targets and destroys the mammalian raptor protein (e.g., siRNA), such as mRNA comprising pairs of oligoribonucleotides which correspond to nucleotides from about nucleotide 1531 to about nucleotide 1551 of SEQ ID NO: 1.

In another embodiment, the present invention provides a method of inhibiting growth rate and/or size of a cell comprising introducing into the cell an agent that enhances interaction of mammalian raptor protein with mammalian TOR protein. The agent can be, for example, exogenous nucleic acid that enhances activity of a mammalian raptor protein.

The present invention also provides a method of altering in vivo activity of mTOR protein in a cell comprising introducing into the cell an agent that alters an interaction of a mammalian raptor protein with the mTOR. In one embodiment, the invention relates to a method of enhancing in vivo activity of mTOR protein in a cell comprising introducing into the cell an agent that inhibits interaction of a mammalian raptor protein with the mTOR. In another embodiment, the invention relates to a method of inhibiting in vivo activity of mTOR protein in a cell comprising introducing into the cell an agent that enhances constitutive interaction of a mammalian raptor protein with mTOR.

The present invention also relates to a method of altering kinase activity of mTOR protein in a cell comprising introducing into the cell an agent that alters interaction of a mammalian raptor protein with the mTOR. In one embodiment, the invention relates to a method of enhancing kinase activity of mTOR protein in a cell comprising introducing into the cell an agent that inhibits interaction of a mammalian raptor protein with the mTOR. In another embodiment, the invention relates to a method of inhibiting kinase activity of mTOR protein in a cell comprising introducing into the cell an agent that enhances interaction of a mammalian raptor protein with the mTOR.

The present invention also provides for prophylactic and therapeutic methods of treating a subject at risk of or susceptible to a disorder or having a disorder associated with aberrant raptor and/or mTOR expression or activity. In one aspect, the invention provides a method for preventing in a subject, a disease or condition associated with an aberrant raptor expression or activity, by administering to the subject an agent which alters raptor expression or at least one raptor activity. Subjects at risk for a disease which is caused or contributed to by aberrant raptor expression or activity can be identified by, for example, any of a combination of diagnostic or prognostic assays as described herein. Administration of a prophylactic agent can occur prior to the manifestation of symptoms characteristic of the raptor aberrancy, such that a disease or disorder is prevented or, alternatively, delayed in its progression. Depending on the type of raptor aberrancy, for example, a raptor agonist or raptor antagonist agent can be used for treating the subject. The appropriate agent can be determined based on screening assays described herein.

Another aspect of the invention pertains to methods of modulating raptor expression or activity for therapeutic purposes. The method of the invention involves contacting a cell with an agent that alters one or more of the activities of raptor protein activity associated with the cell. An agent that alters raptor protein activity can be an agent as described herein, such as a nucleic acid or a protein, a naturally-occurring cognate ligand of a raptor protein, a peptide, a raptor peptidomimetic, or other small molecule (e.g., small organic molecule). In one embodiment, the agent stimulates one or more of the biological activities of raptor protein. Examples of such stimulatory agents include active raptor protein and a nucleic acid molecule encoding raptor that has been introduced into the cell. In another embodiment, the agent inhibits one or more of the biological activities of raptor protein. Examples of such inhibitory agents include antisense raptor nucleic acid molecules and anti-raptor antibodies. These methods can be performed in vitro (e.g., by culturing the cell with the agent) or, alternatively, in vivo (e.g, by administering the agent to a subject). As such, the present invention provides methods of treating an individual afflicted with a disease or disorder characterized by aberrant expression or activity of a raptor protein or nucleic acid molecule. In one embodiment, the method involves administering an agent (e.g., an agent identified by a screening assay described herein), or combination of agents that modulates (e.g., upregulates or downregulates) raptor expression or activity. In another embodiment, the method involves administering a raptor protein or nucleic acid molecule as therapy to compensate for reduced or aberrant raptor expression or activity.

Stimulation of raptor activity is desirable in situations in which raptor is abnormally downregulated and/or in which increased raptor activity is likely to have a beneficial effect. Conversely, inhibition of raptor activity is desirable in situations in which raptor is abnormally upregulated, e.g., in cancer, and/or in which decreased raptor activity is likely to have a beneficial effect.

In a particular embodiment, the present invention relates to a method of treating cancer in an individual comprising administering to the individual an agent that enhances interaction of raptor protein with mTOR protein.

EXEMPLIFICATION

Materials and Methods

Materials

Reagents were obtained from the following sources: DSP and Protein G-Sepharose from Pierce; methionine-L-[$^{35}$S] and ATP-[$\gamma$-$^{32}$P] from NEN; mTOR, EGFR, S6K1, actin, lamin, and PI3-K antibodies as well as HRP-labeled anti-mouse, anti-goat and anti-rabbit secondary antibodies from Santa Cruz Biotechnology; Phospho-T389 S6K1 and Phospho-5473 PKB/Akt antibodies from Cell Signaling; HA monoclonal antibody from Covance; myc monoclonal antibody from Oncogene Research Products; myc rabbit polyclonal antibody from Upstate Biotechnology; eIF-4E antibody from Transduction Laboratories; DMEM, leucine, glucose, RPMI, and RPMI without amino acids, leucine, or glucose, from Life Technologies; and rapamycin, FK506, valinomycin, antimycin A, and 2-deoxyglucose from Calbiochem. Rabbit polyclonal anti-peptide antibodies recognizing mTOR (amino acids 221-237) and human raptor (amino acids 985-1001) were produced using the regular antibody service from Zymed.

Crosslinking Assay and Immunoprecipitations 3 million HEK293T cells growing in 6 cm dishes in DMEM with 10% dialyzed fetal calf serum were metabolically labeled by the addition of 0.4 mCi of [$^{35}$S] methionine for 2 hours. Cells were rinsed once with PBS and lysed in 300 µl of ice-cold Buffer A (40 mM Hepes pH 7.5, 120 mM NaCl, 1 mM EDTA, 10 mM pyrophosphate, 10 mM glycerophosphate, 50 mM NaF, 1.5 mM Na$_3$Vo$_4$, 1% Triton X-100, and one tablet EDTA-free protease inhibitors (Roche) per 10 ml) with or without 2.5 mg/ml DSP and incubated for 30 min on ice. Crosslinking reactions were quenched by adding 75 µl 1M Tris-HCl pH 7.4 followed by an additional 30 min incubation. After clearing the lysates by centrifugation at 10,000×g for 10 min, 30 µA of a 50% slurry of protein G-Sepharose and 4 µg of the anti-mTOR antibody or control antibodies were added to the supernatant. After a 3 hour incubation at 4° C., immunoprecipitates were washed once each with Tris-buffered saline containing 0.05% Tween 20, Wash Buffer 1 (50 mM Hepes pH 7.5, 40 mM NaCl, and 2 mM EDTA) with 1% Triton X-100, Wash Buffer 1 with 500 mM LiCl and 0.5% Triton X-100, Wash Buffer 1 with 500 mM LiCl, and Wash Buffer 2 (50 mM Hepes, pH 7.5, and 150 mM NaCl). 5× sample buffer (0.242 M Tris, 10% SDS, 25% glycerol, 0.5M dithiothreitol and bromophenol blue) was added to washed immunoprecipitates and incubated for 1 h at 37° C. to reduce the DSP crosslinking Samples were resolved by 3-8% SDS-PAGE, proteins transferred to PVDF and the blot exposed to film. Cross-linking experiment using unlabeled cells were analyzed by silver staining of gels.

Unless otherwise stated, for mTOR immunoprecipitates prepared in the absence of the cross-linker, cells were lysed in ice-cold Buffer B (Buffer A in which Triton X-100 is replaced by 0.3% CHAPS) and immunoprecipitates were washed four times in Buffer B and twice in Wash Buffer 2.

Protein Sequencing of Raptor mTOR immunoprecipitates prepared from 200 million HEK293T cells were prepared as above, resolved by SDS-PAGE, and proteins visualized by Coomassie blue staining The band corresponding to raptor was excised and trypsinized as described (Erdjument-Bromage et al., *Protein Sci* 3:2435-46 (1994)). A hundred percent of the generated peptides were subjected to a micro-clean-up procedure using 2 μL bed-volume of Poros 50 R2 (PerSeptive) reversed-phase beads packed in an Eppendorf gel-loading tip. Mass spectrometry (MALDI-ReTOF) was then carried out on two peptide pools (16 and 30% MeCN) recovered from the RP-microtip column using a Bruker REFLEX III instrument with delayed extraction. For mass fingerprinting, top major experimental masses (m/z) combined from both MALDI-ReTOF experiments were used to search a non-redundant human protein database (NR; ~66,605 entries; NCBI; Bethesda, Md.), using the PeptideSearch (M. Mann, University of Southern Denmark) algorithm. A molecular weight range twice the predicted weight was covered with a mass accuracy restriction better than 40 ppm, and maximum one missed cleavage site was allowed per peptide. Alternatively, mass spectrometric-based sequencing (ESI-MS/MS) of selected peptides from partially fractionated pools was carried out using a PE-SCIEX API300 triple quadrupole instrument, fitted with a continuous flow nano-electrospray source (JaFIS). All peptide masses in pools were obtained by DE-MALDI-reTOF MS (BRUKER Reflex III). Peptide sequences were obtained by nano-electrospray tandem MS (JaFIS® source with SCIEX API300 triple quadrupole).

Cloning of the Raptor cDNA, DNA Manipulations and Mutagenesis

The cDNA for the KIAA1303 protein was obtained from the Kazusa DNA Research Institute. It encodes amino acids 200-1335 of raptor downstream of 126 bases of unknown origin that are not present in the EST databases and likely represent unspliced intronic sequence. To identify the full-length raptor sequence, EST databases with bases 127-500 of KIAA1303 were searched and cDNAs that extended the sequence in the 5' direction were identified. The 5' sequences of these cDNAs were used to search the EST databases for cDNAs that further extended the 5' end of the raptor mRNA and this process was repeated until no additional cDNAs were found. The sequences obtained in this fashion allowed us to design PCR primers and amplify the 5' end of raptor using first strand cDNA prepared from human BJAB cell RNA as template. PCR products were subcloned into the pCRII vector using a T/A cloning kit (Invitrogen) and sequenced. To create the 7051 base pair cDNA for the full length raptor mRNA, the PCR fragments and KIAA1303 were assembled in pBluescript SK-II(+) (Stratagene) using restriction sites found in overlapping regions. For expression in mammalian cells, the entire raptor open reading frame was subcloned into the myc- and HA-prk5 vectors (Sabatini et al., Science 284:1161-4 (1999)).

Figure 6A:
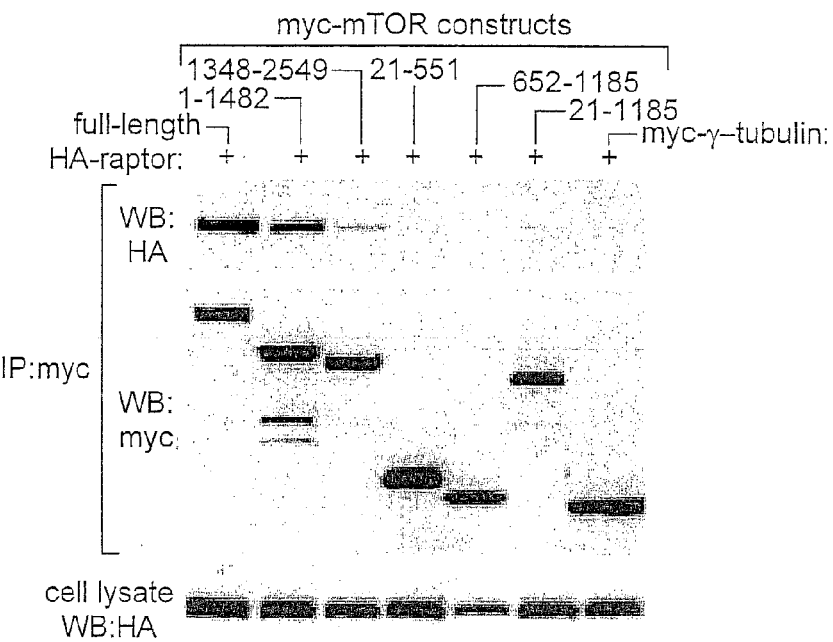
FIGS. 6A-6B show identification of protein domains involved in the mTOR-raptor interaction.
Figure 6B:
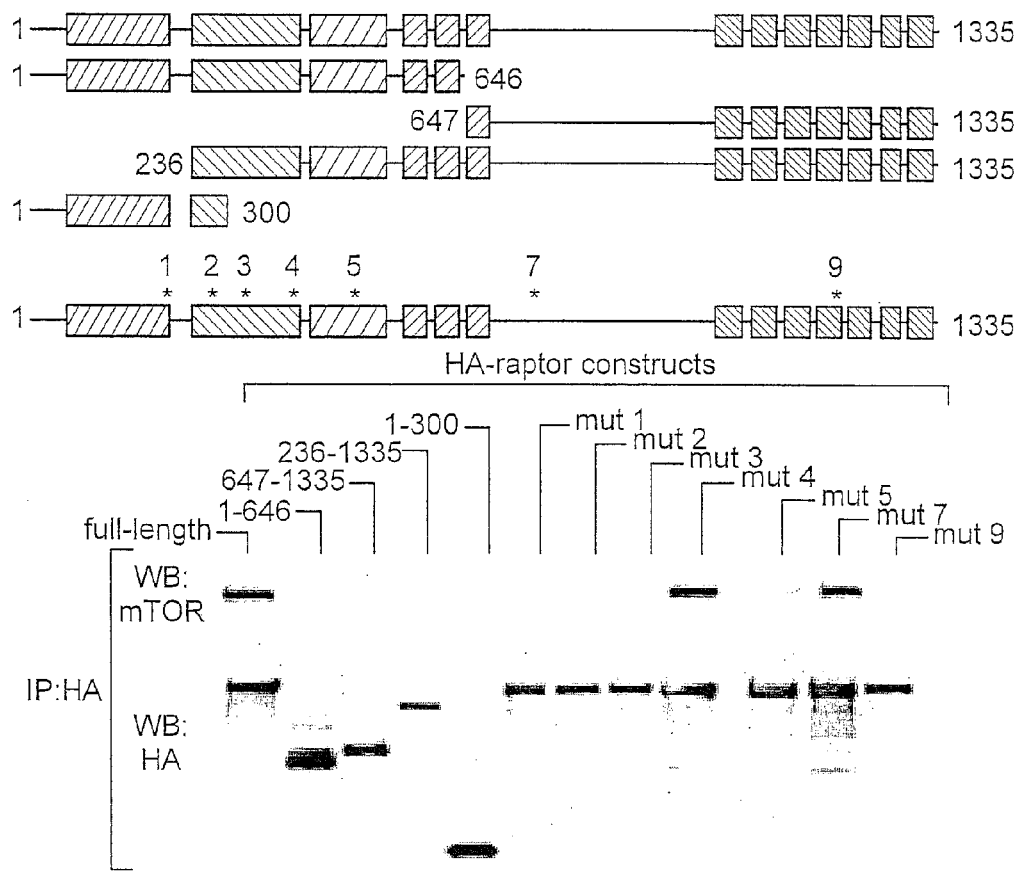

The raptor and mTOR fragments indicated in FIGS. 6A-6B were expressed from cDNAs subcloned into the HA- and/or myc-prk5 vectors. The raptor open reading frame in pBluescript SK-II(+) was mutagenized using the QuikChange mutagenesis kit (Stratagene) and subcloned into the Sal 1 and Not 1 sites of HA-prK5. Mutants used in this study are: raptor mut1 ($_{194}$YDC$_{196}$-AAA), mut2 ($_{261}$DLF$_{263}$-AAA), mut3 ($_{313}$NWIF$_{316}$-AAAA), mut4 ($_{391}$SQ$_{392}$-PA), mut 5 ($_{473}$FPY$_{475}$-AAA), mut 7 ($_{738}$SLQN$_{741}$-PAAA), and mut 9 ($_{1191}$RVYDRR$_{1196}$-DAAADD).

Sequence Analysis and Alignments

Unaligned sequences of raptor homologues were submitted to the MEME server (Multiple Em for Motif Elicitation v3.0) (Bailey and Elkan, Proc. Int. Conf Intel'. Syst. Mol. Biol. 2:28-36 (1994)) at http://meme.sdsc.edu/meme/website/ to identify blocks of similar sequence between the proteins. Three blocks (1, 2, and 3) of similar sequence were identified in the N-terminal half of all the homologues and collectively named the RNC (Raptor N-terminal Conserved) domain. The sequences were then examined for the presence of common protein motifs using a Pfam v6.6 fragment search (Sonnhammer et al., Proteins, 28:405-420 (1997)) at http://pfam.wustl.edu/ and three HEAT-like and seven WD40-like repeats were found in each protein. The sequences of the raptor homologues were also aligned with ClustalX (v1.81) (Thompson et al., Nucleic Acids Res. 25:4876-82 (1997)) using the Gonnet series weight matrix. Pairwise gap opening and gap extension penalties were set at 10.00 and 0.10, respectively. Multiple alignment gap opening and gap extension penalties were set at 10.00 and 0.20, respectively. The ClustalX alignment recapitulated the results of the MEME search, highlighting the three blocks of conserved identity and similarity corresponding to the RNC domain. In addition, the HEAT-like and WD40-like repeats were also aligned. Secondary structure prediction (Rost and Sander, J. Mol. Biol. 232:584-99 (1993)) was performed at http://cubic.bioc.columbia.edu.

Plasmid and siRNA Transfections 3 million HEK293T cells in 6-cm dishes were transfected with plasmid constructs and amounts indicated in the Figure legends using the Lipofectamine 2000 transfection reagent (Life Technology). 24 hours after DNA addition, cells were rinsed once with PBS and lysed in 300 μl of ice-cold Buffer B. Immune complexes were prepared from cleared supernatants using 3 μg polyclonal anti-myc or monoclonal anti-HA antibodies and 20 μl of a 50% slurry protein G-Sepharose. After a 3 hour incubation, immunoprecipitates were washed six times with Buffer B and twice with Wash Buffer 2. Bound proteins were eluted in 1× sample buffer, and mTOR or HA- or myc-tagged proteins were detected by immunoblotting as described (Burnett et al., PNAS 95:1432-143 (1998)).

For the siRNA experiments, 21-nucleotide complementary RNAs with symmetrical 2-nucleotide overhangs were obtained from Dharmacon (Boulder, Colo.) and designed to target the following regions of the open reading frames: bases 1531-1551 or 3374-3394 of raptor, bases 2241-2261 of human mTOR (FRAP), and bases 608-630 of human lamin. Oligonucleotides were annealed into duplexes as described (Elbashir et al., Embo J. 20:6877-88 (2001)) and transfected at 40 nM with Effectene (Qiagen) into HEK293T cells cultured in Optimem media (Life Technology) without serum. Unless otherwise described, 48 hours after adding siRNAs, the medium was replaced with DMEM containing 10% serum, and cells were cultured for a further 24 hours before use in experiments. mRNA levels of raptor and mTOR in siRNA transfected cells were determined by quantitative RT-PCR using a SYBR green assay as described (Alfonso et al., J. Neurosci. Res. 67:225-34 (2002)).

Cell Size Determinations

For the regrowth after confluence experiment, HEK293T cells were transfected with siRNAs as described above and grown to confluence in a 6-cm culture dish for 24 hours. Cells were then harvested, diluted 1:10 or 1:20 and replated in fresh media. At 1, 2, and 3 days after replating, the cells were harvested by trypsinization in 2 ml media, diluted 1:20 with counting solution (Isoflow Sheath Fluid, Coulter Corp.) and cell diameters and volumes determined using a particle size counter (Coulter Multisizer II). Cells between 11 and 21 μm in diameter were used for analysis. For the leucine-induced growth experiment, the siRNA transfected cells were diluted into fresh media one day after transfection and, at 24 hours after dilution the cells were deprived of leucine for a further 24 hours. The cells were then provided with leucine (52 μg/ml) and cell diameters, volumes, and numbers determined as above at 6 and 10 hours after the leucine supplementation.

In Vitro Kinase Assay for mTOR Activity

Kinase assays were performed in a volume of 10 µl at 30° C. for 20 min and contained ¼ the washed mTOR immunoprecipitates from 10 million HEK293T cells growing on a 10-cm dish, 200 ng of a GST-S6K1 fusion protein (amino acids 332-502), 1 µCi of [$\gamma$-$^{32}$P]ATP, 25 mM Hepes-KOH, pH 7.4, 50 mM KCl, 20% glycerol, 10 mM MgCl$_2$, 4 mM MnCl$_2$, 1 mM DTT, and 50 µM unlabeled ATP. When inhibitors were used they were added to the mTOR immunoprecipitates 10 minutes prior to the start of the kinase assay. Reactions were stopped by the addition of 5 µl of 2× sample buffer. After boiling the samples for 3 min, proteins were resolved by 8% SDS-PAGE, transferred to PVDF (poly(vinylidene difluoride)), and phosphorylated proteins visualized with autoradiography. The same blots were then used to determine the levels of mTOR and raptor by western analysis. Kinase assays using recombinant mTOR were performed as described in Burnett et al., PNAS, 95:1432-1437 (1998), except that they were washed as above with Buffer B.

Results

Identification of Raptor as an mTOR-Associated Protein

Figure 3A:
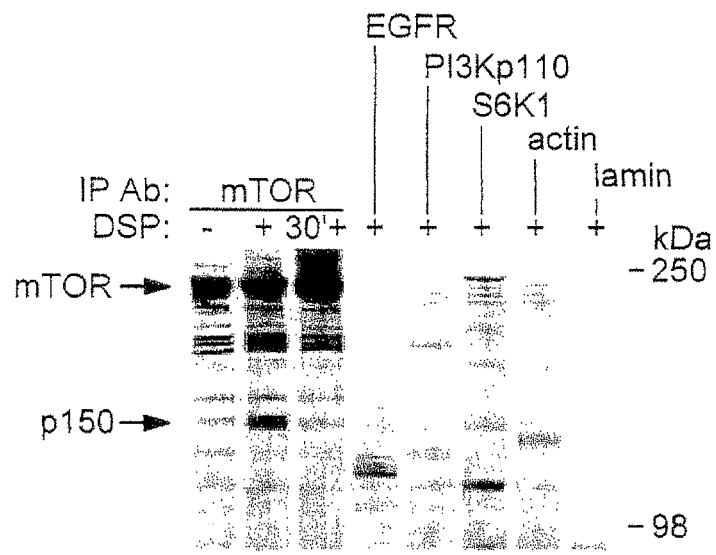
FIGS. 3A-3C are gels which identify a 150 kDa mTOR-associated protein.
Figure 3B:
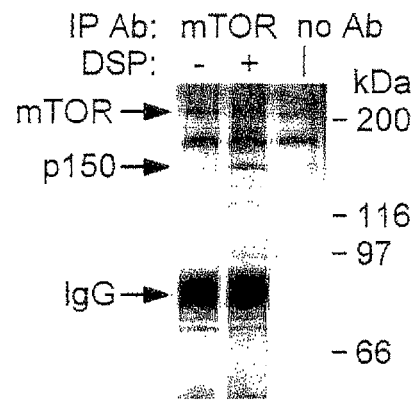
Figure 3C:
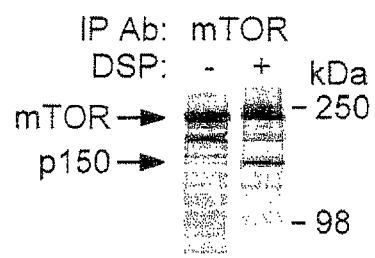

HEK 293T cells were metabolically labeled with [$^{35}$S]-methionine and lysed in the presence or absence of the reversible cross-linker dithiobis(succinimidylpropionate) (DSP). mTOR immunoprecipitates prepared from these lysates were then treated with dithiothreitol to reduce the DSP cross-links and analyzed by SDS-PAGE and autoradiography. A protein with an apparent molecular weight of 150 kDa co-precipitated with mTOR only in immunoprecipitates recovered from lysates prepared in the presence of DSP (FIG. 3A). The intensity of this band decreased significantly when DSP was added 30 minutes after cell lysis, indicating that the protein interacts weakly or transiently with mTOR or that the lysis procedure disrupts the association (FIG. 3A). Immunoprecipitates prepared using antibodies against five other proteins did not co-precipitate the 150-kDa protein, indicating that it specifically interacts with mTOR. For reasons that will become apparent, the 150 kDa protein was designated raptor (Regulatory Associated Protein of mTOR). Raptor was also detected in silver (FIG. 3B) or Coomasie blue stained gels of mTOR immunoprecipitates prepared from DSP-treated lysates of unlabelled cells. Quantitation of the amount of raptor in these gels indicated that it is present in near stoichiometric amounts with mTOR. Furthermore, once sequence information allowed normalization of radioactive band intensities to the methionine content of raptor and mTOR, near stoichiometric amounts of the two proteins were found in complexes isolated from cells metabolically labeled to equilibrium (FIG. 3C).

Raptor is an Evolutionarily Conserved Protein with a Novel N-Terminal Domain and Seven WD40 Repeats To characterize raptor sequence information was obtained by mass spectrometry and three peptides (SVSSYGNIR (SEQ ID NO: 26), LDDQIFLNR (SEQ ID NO: 27), and IPEEHDLESQIR (SEQ ID NO: 28)), all of which are contained within KIAA1303 (NCBI #7242961), a partial ORF for a human protein of unknown function, were identified. Using the BLAST homology search algorithm, it was found that KIAA1303 likely represents an N-terminally truncated fragment of the human homologue of fission yeast Mip1p. The function of Mip1 is not clear, but, interestingly, it has been implicated in cell growth and nitrogen sensing (Shinozaki-Yabana et al., *Mol. Cell Biol.* 20:1234-42 (2000)), processes regulated by TOR proteins in a variety of organisms. By searching EST databases, overlapping cDNAs that extended the 5' end of the KIAA1303 cDNA were identified and sequence information that allowed the design of PCR primers and assembly of a full-length cDNA for human raptor were provided. The 7051 nucleotide mRNA contains an open reading frame encoding a protein of 1335 amino acids (predicted molecular weight of 149 kDa) that is flanked by 5' and 3' untranslated regions of 0.9 and 2.1 kb, respectively. Human genome sequence information for the raptor locus permitted localization of the gene to human chromosome 17q25.3.

Figure 4A:
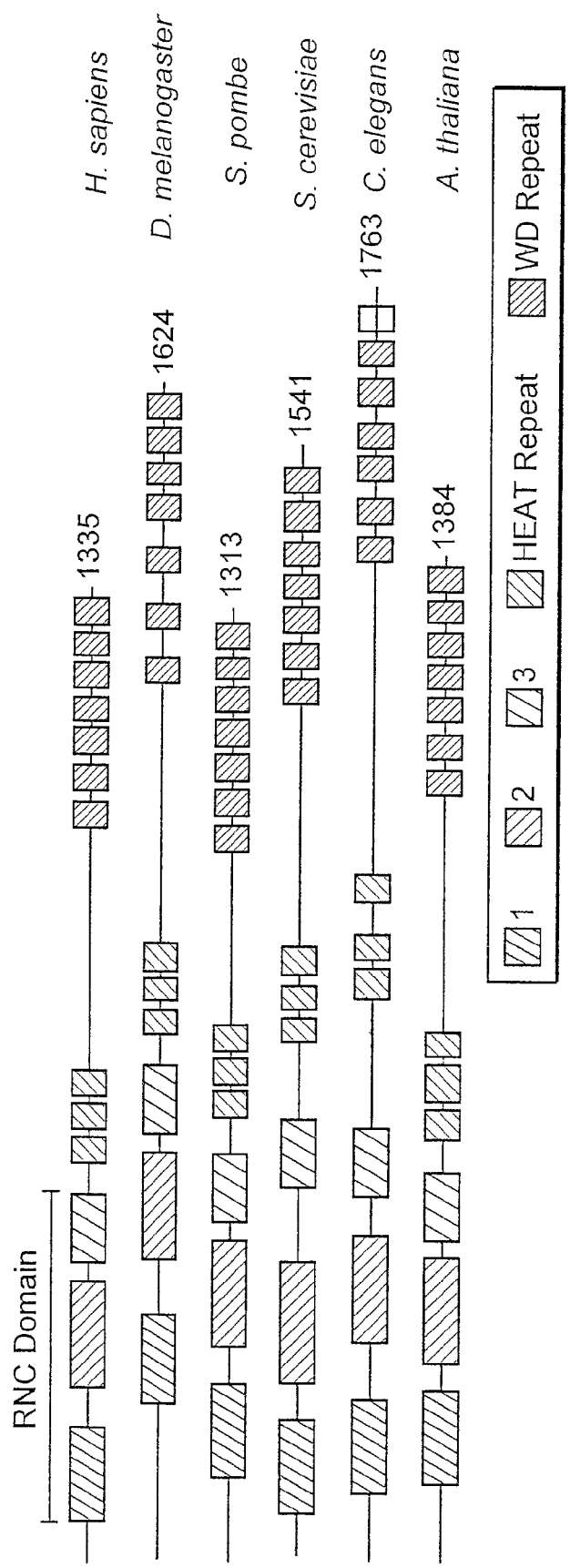
Figure 4B:
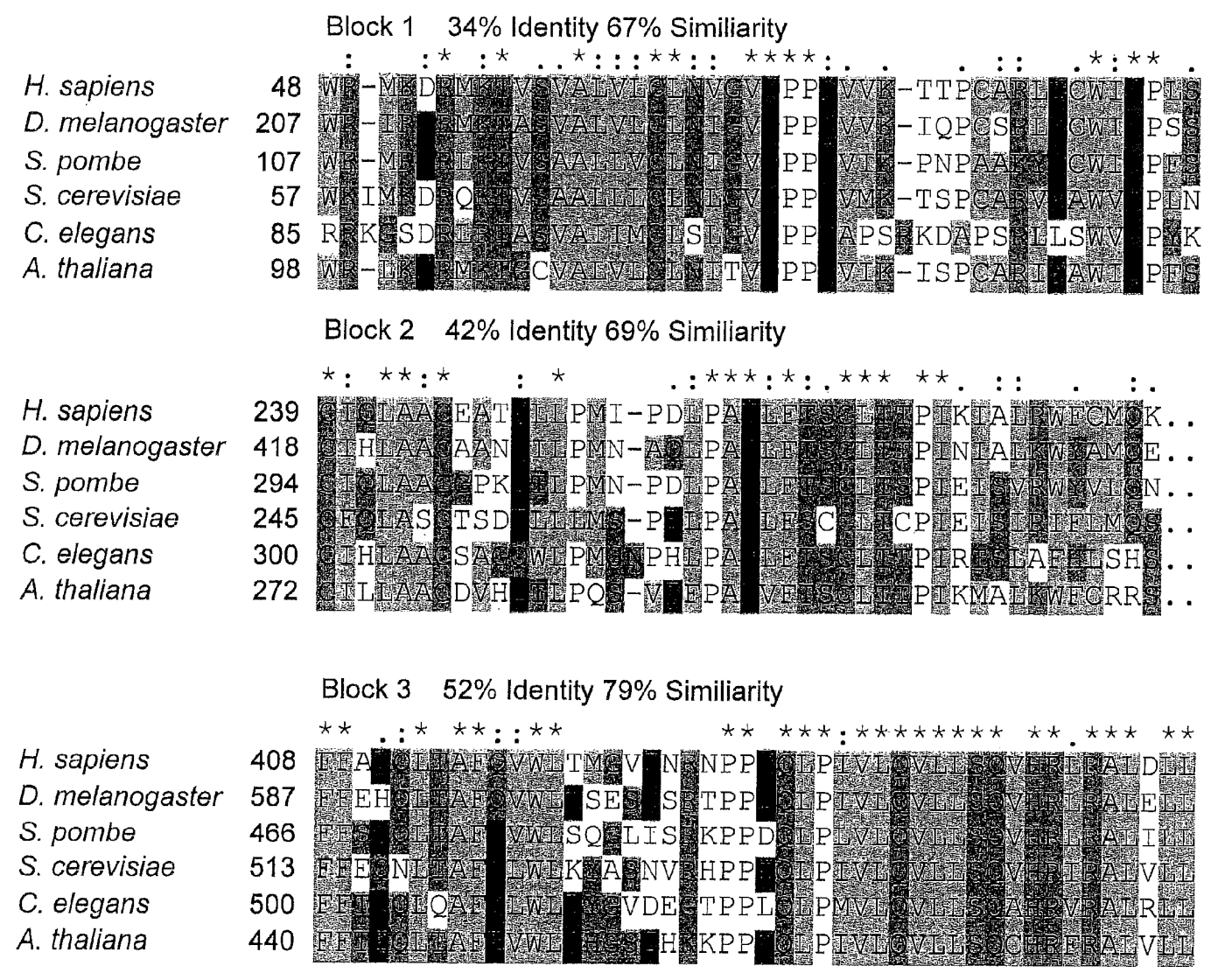
Figure 4C:
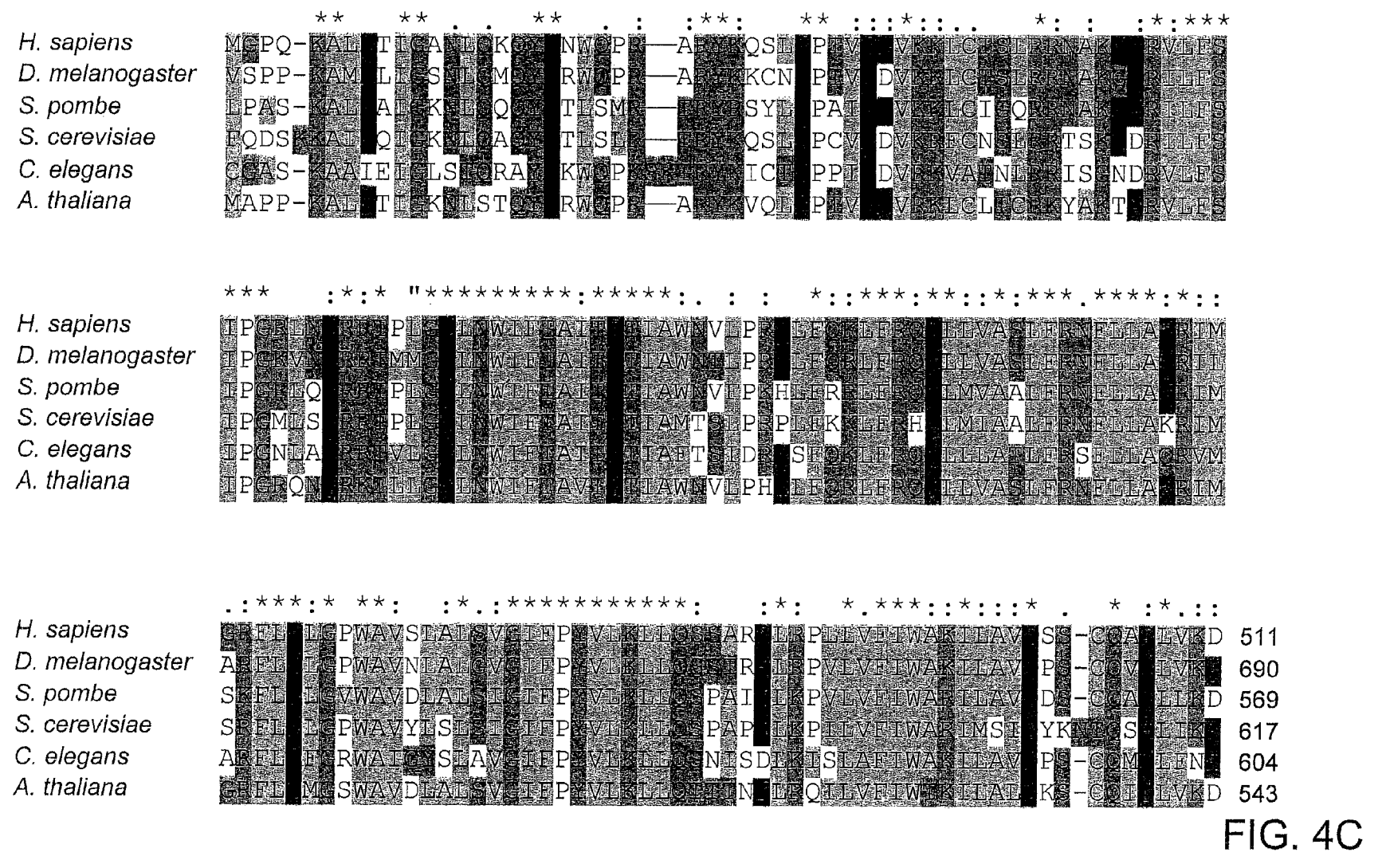

Raptor shows a high degree of conservation amongst all eukaryotes with completed genome projects, including *D. melanogaster*, *S. pombe*, *S. cerevisiae*, *C. elegans*, and *A. thaliana* (FIG. 4A and FIGS. 11A-11I). The raptor homologues in budding (Winzeler et al., *Science* 285:901-6. (1999)) and fission (Shinozaki-Yabana et al., *Mol. Cell Biol.* 20:1234-42 (2000)) yeast are encoded by essential genes. All raptor homologues have a novel N-terminal domain that we have named RNC (for Raptor N-terminal Conserved) domain, and consists of three highly conserved sequence blocks that share at least 67% similarity amongst raptor homologues (FIGS. 4B-4D). The RNC domain is unrelated to other sequences in the public databases and is predicted to have a high propensity to form $\alpha$-helixes. Following the RNC domain, all raptor homologues have three HEAT repeats (Andrade and Bork, *Nat. Genet.* 11:115-6 (1995)), with highly conserved aspartate and arginine residues at motif positions 19 and 25, respectively. The HEAT repeats are followed by seven WD40 repeats in the C-terminal third of the protein (FIG. 4A). Both HEAT and WD-40 repeats are common protein-protein interaction motifs found in many eukaryotic regulatory proteins (Kobe et al., *Structure Fold Des.* 7:R91-7. (1999); Smith et al., *Trends Biochem. Sci.* 24:181-5 (1999)). Northern blot analysis shows that raptor is expressed in all human tissues in a pattern similar to that of mTOR, with the greatest levels of both mRNAs found in skeletal muscle, brain, kidney, and placenta (FIG. 4E). This indicates that both proteins are coordinately expressed in different tissues.

Specific mTOR-Raptor Interaction In Vivo

Figure 5A:
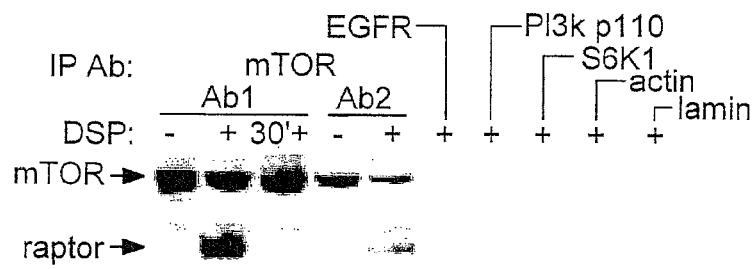
FIGS. 5A-5E show specific in vivo interactions between endogenous raptor and mTOR and recombinant versions of both proteins.
Figure 5B:
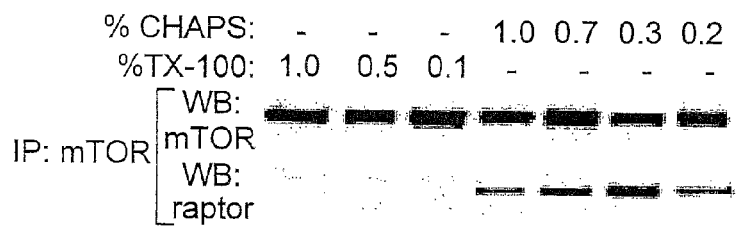
Figure 5C:
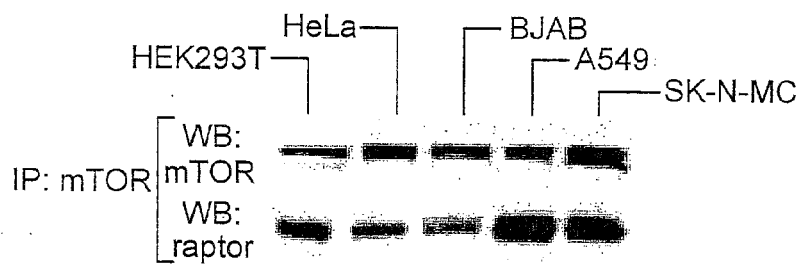
Figures 5D, 5E:
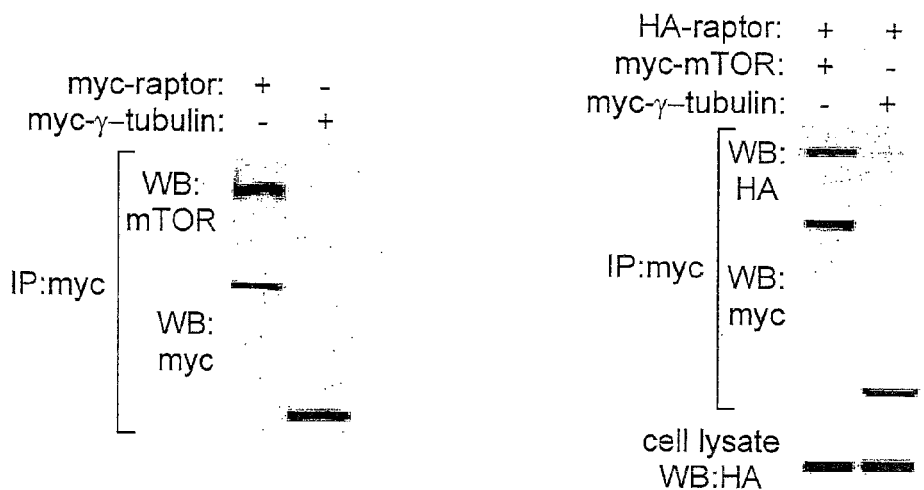

To characterize the mTOR-raptor interaction, a polyclonal antibody that specifically recognizes amino acids 985 to 1001 of human raptor was generated. This antibody detected raptor in immunoprecipitates prepared from DSP-treated cell lysates using two different anti-mTOR antibodies but not in immunoprecipitates obtained with five control antibodies incapable of recognizing mTOR (FIG. 5A). To enable a study of the physiological regulation of the mTOR-raptor interaction lysis conditions that might preserve the complex in the absence of the chemical cross-linker were investigated. This was achieved by avoiding in the lysis buffer Triton X-100, a detergent which eliminated the interaction at all concentrations tested (FIG. 5B). Lysis of cells in buffers containing the detergent CHAPS instead of Triton X-100 preserved the interaction with the greatest amount of co-precipitating raptor obtained at 0.3% CHAPS. Interestingly, the majority of in vitro studies on mTOR function have been performed on mTOR isolated from cells lysed with Triton X-100 or the related detergent NP-40, conditions that were found to completely disassociate raptor from mTOR. All further experiments were performed using a lysis buffer (Buffer B, see methods) containing 0.3% CHAPS and 120 mM NaCl, conditions that allowed the recovery of a complex containing a ratio of about 1.0 mTOR to about 0.7 raptor. In addition to HEK293T cells, the mTOR-raptor complex was detected in all other human cell lines tested, including the uterine cancer HeLa, B-cell lymphoma BJAB, neuroblastoma SK-N-MC, and lung cancer A549 derived cell lines (FIG. 5C), indicating that the association likely occurs in most cell types. In transfected HEK293T cells the interaction of epitope-tagged raptor with endogenous mTOR (FIG. 5D) as well as between epitope-tagged versions of both proteins (FIG. 5E) were detected.

The mTOR-Raptor Interaction Requires the mTOR HEAT Repeats and Multiple Sites on Raptor To identify which region(s) of mTOR interacts with raptor, several myc-tagged mTOR fragments together with the full-length HA-tagged raptor protein were expressed in HEK293T cells. The N-terminal region of mTOR (amino acids 1 to 1482) containing all the HEAT motifs interacted with raptor almost as strongly as the full length protein, whereas the C-terminal region (amino acids 1348-2549) exhibited a weak but greater than background interaction (FIG. 6A). Further shortening of the N-terminal region of mTOR by 297 residues severely weakened the interaction and fragments of the N-terminal region of mTOR (amino acids 21-551 or 652-1185) were incapable of interacting with raptor (FIG. 6A). These results indicate that the overall structure of the N-terminal portion of mTOR is required for the association with raptor and that the C-terminal half of mTOR contains a weaker interaction site.

Whether individual domains of recombinant HA-tagged raptor expressed in HEK293T cells could interact with the endogenous mTOR was also tested (FIG. 6B). None of the raptor fragments bound to mTOR, indicating that the overall structure of raptor is required for the interaction. Several mutations in the RNC or WD40 domains of raptor, generated by changing evolutionarily conserved residues (FIG. 6B), eliminated the interaction with mTOR, whereas another RNC domain mutation (mut 4), as well as a mutation in the region between the HEAT and WD40 repeats (mut 7), did not affect it. These observations indicate that the mTOR-raptor interaction involves multiple sites in raptor and a large region of mTOR and, therefore, indicate that both proteins make extensive contacts with each other. Alternatively, the mutations in raptor could destabilize its entire structure and, thus, disturb the mTOR-raptor association without directly being part of the mTOR-interaction site. Interestingly, ATR, a protein which like mTOR is a member of the PIK-related family of kinases, makes extensive contacts with ATRIP (ATR-Interacting Protein), a recently discovered interacting partner of ATR (Cortez et al., *Science* 294:1713-6 (2001)).

Raptor Participates in Nutrient Signaling and Maintenance of Cell Size

Figure 7A:
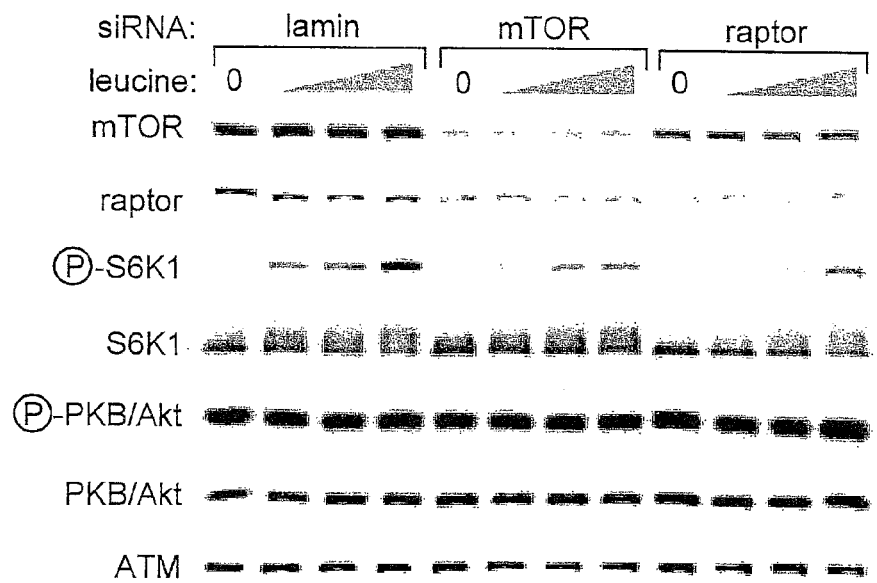
FIGS. 7A-7E show that Raptor participates in nutrient signaling to S6K1, maintenance of cell size and in cell growth.
Figure 7B:
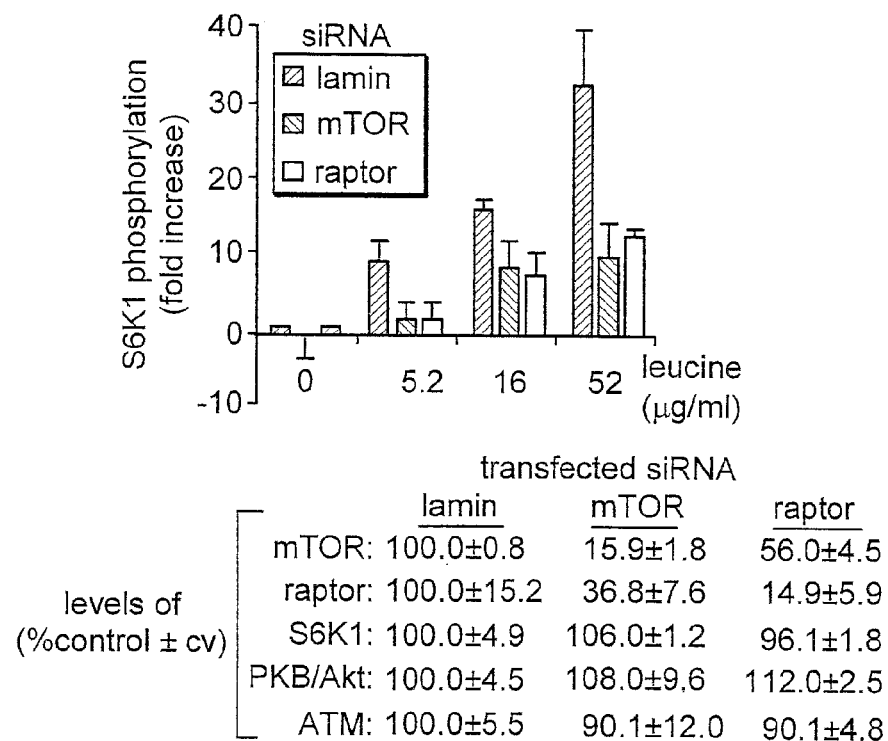

A major role of the mTOR pathway is to coordinate the synthesis of ribosomal proteins with the levels of available amino acids. This is accomplished by controlling the translational regulator S6K1, a kinase whose phosphorylation state and in vivo activity are regulated by amino acid levels (Fox et al., *American Journal of Physiology Cell Physiology* 274: 43-1 (1998); Hara et al., *J Biol. Chem.* 273:14484-94. (1998)) and is phosphorylated in vitro by mTOR (Burnett et al., *PNAS* 95:1432-1437. (1998); Isotani et al., *J. Biol. Chem.* 274: 34493-8. (1999)). To investigate the role of raptor in mTOR-mediated signaling, small interfering RNA (siRNA) (El-bashir et al., *Nature* 411:494-8 (2001)) were used to decrease endogenous levels of raptor in HEK293T cells and the phosphorylation state of S6K1 in response to stimulation with increasing concentrations of leucine was measured. Consistent with a critical role for raptor in nutrient signaling to S6K1, decreased levels of raptor attenuated leucine-stimulated phosphorylation of S6K1 to a similar extent as decreased levels of mTOR achieved with an siRNA specific to mTOR (FIGS. 7A and 7B). After stimulation with the highest concentration of leucine the cells with reduced amounts of raptor or mTOR had only about 30% of the level of S6K1 phosphorylation as the cells transfected with the control siRNA (FIG. 7B). Reductions in the levels of raptor or mTOR did not significantly affect the amounts of S6K1 and ATM, or the phosphorylation state or amount of PKB/Akt, a downstream effector of PI 3-Kinase (FIGS. 7A and 7B). Interestingly, mTOR and raptor expression appear to be coordinately regulated because reduced levels of either protein induced by its specific siRNA also decreased the level of the other without affecting the amount of its mRNA. The inhibitory effect on S6K1 signaling of the raptor-targeted siRNA is not simply due to its decrease of mTOR levels. In control experiments using the mTOR-targeted siRNA, it was found that to observe any effect on S6K1 phosphorylation mTOR had to be reduced to less than 25% its normal level, a far higher reduction than caused by the raptor-targeted siRNA (FIG. 7B). The mutual dependence of expression observed between mTOR and raptor is another similarity the partners share with the ATR-ATRIP interacting pair (Cortez et al., *Science* 294:1713-6 (2001)).

Figure 7C:
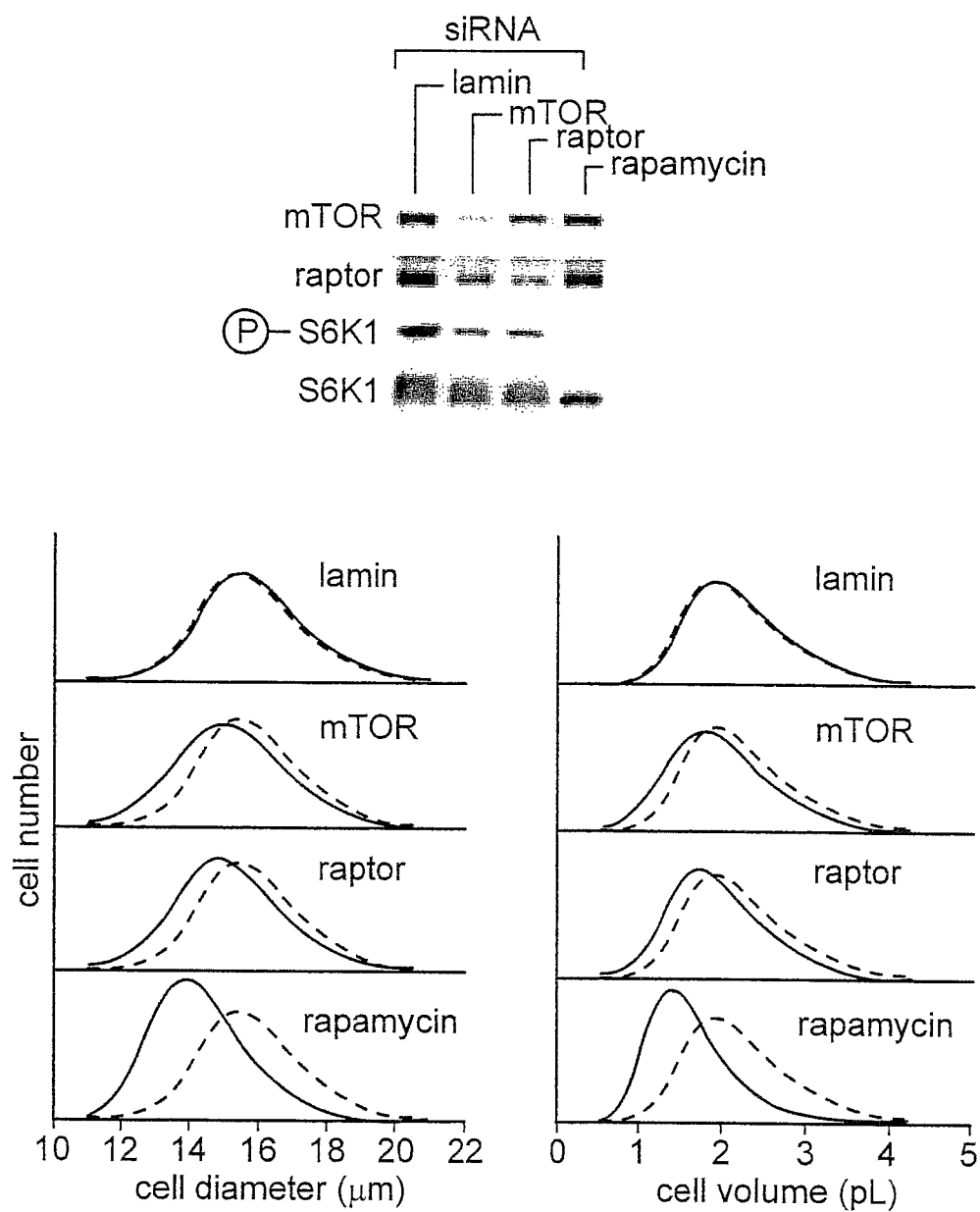

In *Drosophila*, the TOR pathway is a major regulator of cell growth and, thus, cell size (Oldham et al., *Genes Dev.* 14:2689-94 (2000); Zhang et al., *Genes Dev.* 14: 2712-24. (2000)). A large part of this regulation is exerted through S6K1, and, in *Drosophila* and mice, loss of function mutations in S6K1 lead to smaller animals with smaller cells (Montagne et al., *Science* 285:2126-9 (1999); Shima et al., *Embo J.* 17:6649-59 (1998)). A role for mTOR in regulating cell growth can also be demonstrated in tissue culture, as inhibition of the pathway with rapamycin treatment reduces the size of many mammalian cell types, including HEK293Ts (FIG. 7C). Consistent with a role for raptor in growth control, it was found that actively growing cells transfected with siRNAs targeting raptor or mTOR underwent comparable reductions in size and that these correlated with a decrease in the phosphorylation state of S6K1 (FIG. 7C). The siRNA-mediated reductions in cell size are highly significant (p<0.001) but less than the reduction caused by treatment of cells with rapamycin for 48 hours. This is expected because rapamycin completely inhibits S6K1 phosphorylation in all of the cells, while the raptor and mTOR siRNAs partially inhibit S6K1 only in transfected cells.

Raptor Participates in Cell Growth

Figure 7D:
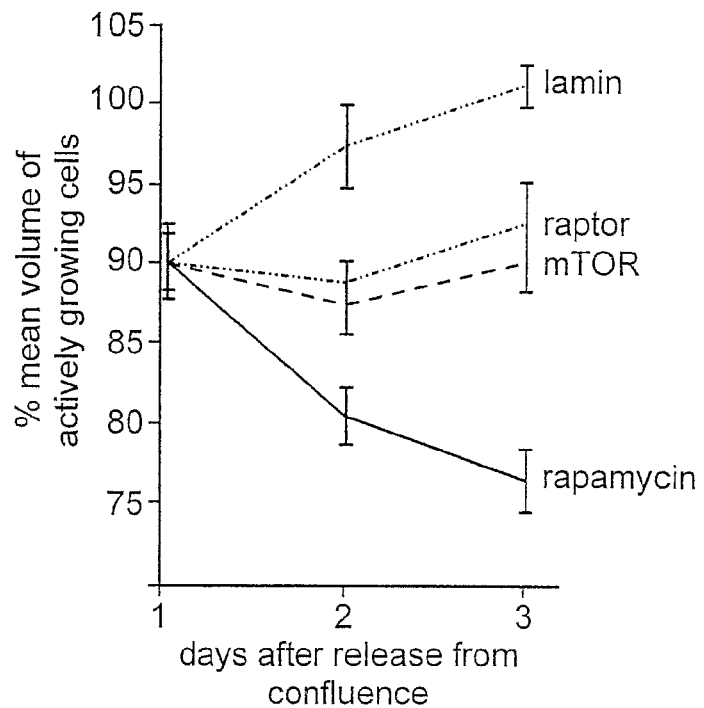

HEK293T cells grown to confluence in a tissue culture dish become smaller than actively growing cells and, after dilution and plating into fresh media, regain their normal mean size over a period of three days. The effects of reducing raptor and mTOR levels on the capacity of cells to increase in mean size after emerging from confluence were examined (FIG. 7D). Cells were transfected with siTNAs targeting lamin, mTOR or raptor and plated at high density so that they reached confluence within 24 hours. The confluent cells were harvested, diluted into fresh media, replated and their mean size measured for three days (FIG. 7D). As the cells transfected with the lamin siRNA emerged from confluence they gradually increased in mean size over a period of three days, an effect that was inhibited in the cells transfected with the mTOR or raptor siRNAs and dramatically reduced by rapamycin.

Figure 7E:
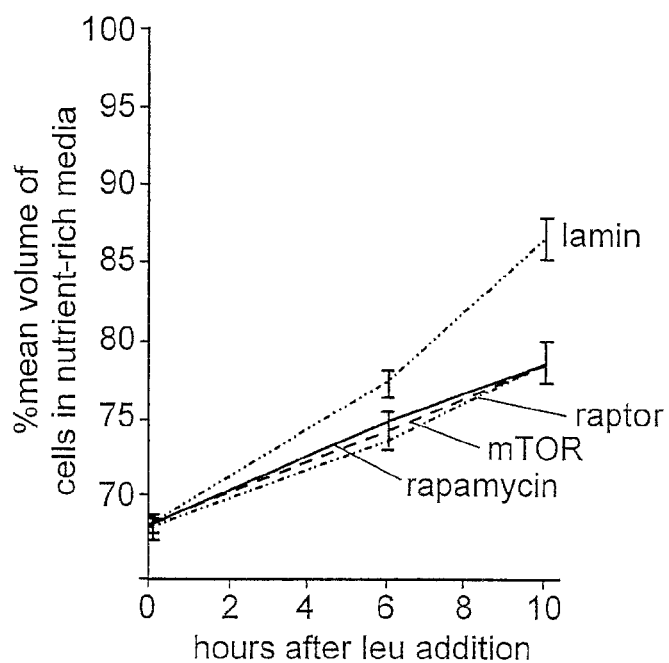

The effects of reducing raptor and mTOR levels on the capacity of cells, in the absence of proliferation, to grow after a reduction in size caused by prolonged nutrient deprivation were also examined. Cells transfected with siRNAs targeting lamin, mTOR or raptor and, 24 hours after transfection, cells were incubated in leucine-free media for an additional 24 hours. During this period of leucine deprivation the cells ceased to divide and became extremely small so that, irrespective of transfected siRNA, the mean cell volume in all the samples was about 67% of the mean volume of cells in leucine-containing media (FIG. 7E). Leucine was then added to the media and cell size measured at 6 and 10 hours after leucine addition. The growth of cells transfected with the mTOR or raptor siRNAs or treated with rapamycin at the same time of leucine addition was impaired as these cells increased in size significantly less than those transfected with the lamin siRNA. During this period of growth the cells did not divide and resumption of cell proliferation did not begin until 15-20 hours after leucine addition.

As described above, reductions in raptor and mTOR protein levels have similar effects on nutrient-stimulated phosphorylation of S6K1, cell size, and cell growth. In addition, it was found that mTOR and raptor exist in a near stoichiometric complex (FIGS. 3A-3C). An efficient explanation for these findings is that raptor and mTOR are part of the same signaling system that regulates S6K1 phosphorylation. Formally, however, it is possible that mTOR and raptor are in independent pathways that both converge on nutrient-stimulated S6K1 phosphorylation. If this was the case, it would be expected that reducing both raptor and mTOR levels in the same cells would have additive inhibitory effects on the nutrient-stimulated S6K1 phosphorylation because two independent pathways would not be affected. It was found that in cells co-transfected with siRNAs targeting both raptor and mTOR S6K1 phosphorylation is reduced to a similar extent in cells transfected with either the mTOR or raptor siRNA (FIG. 12). This finding supports mTOR and raptor being part of the same nutrient-regulated growth pathway.

Nutrients and Mitochondrial Function Regulate the Stability of the mTOR-Raptor Complex and the mTOR Kinase Activity To determine if the mTOR-raptor interaction is regulated by conditions that are known to affect the activity of downstream effectors of mTOR, the effects of different nutrient conditions on the stability of the mTOR-raptor complex were tested. The amount of raptor recovered bound to mTOR was markedly increased when HEK293T cells were incubated in amino acid deprived medium, an effect that was mimicked by the removal of just leucine from the culture medium (FIG. 8A). More importantly, a ten-minute stimulation with leucine, which activates the phosphorylation of S6K1 (FIGS. 7A-7B and lower panels of FIG. 8A), reversed the effect of leucine deprivation and restored the interaction to the level observed in cells grown in nutrient-rich medium. Furthermore, the in vitro kinase activity of mTOR towards S6K1 inversely correlated with the amount of raptor recovered with mTOR. Greater activity was observed in raptor-deprived complexes obtained after nutrient stimulation. Conversely, reduced activity was observed in raptor-enriched complexes obtained after nutrient starvation (FIG. 8A). It was also found that glucose deprivation and re-addition affected the mTOR-raptor interaction and mTOR activity in the same way as did changes in leucine levels (FIG. 8A).

Although mild buffers were used to prepare the mTOR immunoprecipitates (in order to preserve the raptor-mTOR association), control kinase assays confirm that the observed activity is that of mTOR and not of a contaminating kinase that also might be capable of phosphorylating S6K1 (FIG. 8B). The kinase activity in the mTOR immunoprecipitates depends on the presence of mTOR and is sensitive to LY294002, a known inhibitor of mTOR (Brunn et al., *Science,* 277:99-101 (1997)), but not to high concentrations of PKI (an inhibitor of PKA), H-8 (an inhibitor of PKA, PKG, and PKC) and PD98059 (an inhibitor of MEK) (FIG. 8B top panel). Moreover, kinase assays performed on recombinant wild-type and kinase-dead mTOR isolated under mild buffer conditions show that the phosphorylation of S6K1 depends on a wild-type mTOR kinase domain and is sensitive to LY294002 (FIG. 8B, bottom panel). Thus, these findings show that, when mTOR is isolated under conditions designed to preserve its interaction with raptor, the activity of the isolated kinase does change in concert with the in vivo effects of stimuli that regulate the pathway. Moreover, two different nutrients, leucine and glucose, similarly affect the mTOR-raptor interaction, indicating that its regulation is a common event downstream of diverse nutrient signals.

The identity of the intracellular messengers that signal nutrient availability to mTOR is unknown, but several lines of evidence suggest that the mitochondrial metabolism of nutrients is necessary to activate the pathway (Dennis et al., *Science* 294:1102-5. (2001); Xu et al., *Diabetes* 50:353-60. (2001)). It was found that valinomycin, a mitochondrial uncoupler (Bernard and Cockrell, *Biochim. Biophys. Acta,* 548:173-186 (1979)); antimycin A, an electron transport inhibitor (Wolvetang, E. J., et al., *FEBS Letters,* 339:40-44 (1994)); and 2-deoxyglucose, a glycolytic inhibitor, stabilized the mTOR-raptor interaction and inhibited mTOR kinase activity in a similar fashion as nutrient deprivation (FIG. 8C). Other cell stressing conditions known to inhibit S6K1 in vivo, such as the oxidative stress caused by $H_2O_2$ treatment, which affects mitochondrial function (Majumder et al., *Cell Growth Differ.* 12:465-70. (2001)), also stabilized the interaction and inhibited the mTOR kinase (FIG. 8C). On the other hand, a sucrose-induced osmotic shock decreased the phosphorylation state of S6K1 but had only a modest effect on complex stability and kinase activity (FIG. 8C). In addition to nutrients and cell stress, growth factors such as insulin are also known to regulate downstream components of the mTOR pathway, like S6K1 (Lawrence and Brunn, *Prog. Mol. Subcell. Biol.,* 26:1-31 (2001). However, it was found that while treatment of serum-starved cells with insulin increased the phosphorylation state of S6K1, it did not affect the raptor-mTOR interaction (FIG. 13), indicating that its regulation is independent of growth factor signaling.

Increasing the Amount of Raptor Bound to mTOR Leads to an Inhibition of the mTOR Kinase Activity The inverse correlation between the stability of the mTOR-raptor interaction and the kinase activity of mTOR indicates that a strong association between raptor and mTOR leads to an inhibition the mTOR catalytic activity. To substantiate this correlation, the activity of mTOR isolated under cell lysis conditions that differentially affect the mTOR-raptor association was determined (mutant 1, FIG. 14). A small increase in salt concentration in the lysis buffer slightly reduced the amount of raptor bound to mTOR and this correlated with a corresponding increase in mTOR activity. Strikingly, the addition of Triton X-100 to the lysis buffer completely eliminated the interaction and also strongly activated in vitro mTOR activity.

To exclude the possibility that the different isolation conditions directly affect mTOR activity, whether an increase in the intracellular concentration of raptor could drive, even in cells growing in nutrient-rich conditions, the formation of stable mTOR-raptor complexes and inhibit mTOR kinase activity was determined. Overexpression of wild-type raptor, but not of a mutant that cannot interact with mTOR (mutant 1, FIGS. 6A-6B), resulted in an increased amount of raptor bound to mTOR and a decrease in its in vitro kinase activity (FIG. 8D). In addition, the overexpression of wild type, but not mutant raptor, decreased the in vivo phosphorylation state of S6K1 and increased the amount of 4E-BP1 bound to eIF-4E (FIGS. 8D and 8E), providing in vivo correlates of the inhibitory effects of raptor on the in vitro mTOR kinase activity. These results strongly indicate that a function of a tightly bound raptor leads to a decrease mTOR kinase activity and that raptor overexpression can circumvent the normal nutrient-regulated mechanism(s) that control the strength of the interaction.

Evidence that the mTOR-Raptor Complex Exists in Two Binding States

Despite the negative role of raptor in regulating the nTOR kinase activity, the experiments using the siRNA indicate that in vivo raptor also has a positive function in the mTOR pathway as decreases in raptor levels reduce S6K1 phosphorylation, cell size, rate of cell growth, and mTOR expression (FIGS. 7A-7E). Moreover, when a cross-linker was present during the lysis of cells raptor was isolated in a stiochiometric complex with mTOR (FIGS. 3A-3C). Thus, it is unlikely that the decrease amount of raptor recovered with mTOR isolated from cells grown in nutrient-rich conditions (FIG. 8A) reflects a dissociation of the mTOR-raptor complexes in vivo. This was proven to be the case, as the amounts of raptor recovered with mTOR isolated from leucine deprived or stimulated cells were similar when cells were lysed in the presence of the chemical cross-linker (FIG. 9A).

These findings show that in vivo raptor and mTOR physically interact under all nutrient conditions and indicate that mTOR-raptor complexes exist in at least two nutrient-determined states with differential stability: an unstable complex that does not survive in vitro isolation and a stable complex that does. As nutrient-rich conditions decreased the amount of raptor recovered with mTOR, it is likely that nutrients lead to the formation of the unstable complex. Evidence for these two binding states was sought by asking if any of the raptor mutants identified, formed complexes with mTOR that were permanently in the unstable or stable state. A mutant that forms an unstable complex with mTOR was searched for by screening the mutants for those that are recovered with mTOR only when cells are lysed in the presence of a cross-linker (FIG. 9B). Only one mutant (mutant 5) had this characteristic, indicating that in vivo mutant 5 does associate with mTOR but that the interaction does not survive the in vitro isolation conditions. As expected, the small residual interaction of mutant 5 with mTOR was no longer sensitive to levels of leucine in the media (FIG. 9C). Next, a mutant that forms a stable complex with mTOR irrespective of nutrient conditions was searched for. Of the two raptor mutants (mutants 4 and 7) that associate with mTOR in the absence of a cross-linker (FIG. 9B), the interaction of mutant 4 was not sensitive to leucine levels while that of mutant 7 was still regulated (FIG. 9C). These findings indicate that mutants 5 and 4 form complexes similar to those found under nutrient-rich and -poor conditions, respectively. Complexes containing mutant 5 are in the unstable state characteristic of nutrient-rich conditions while those containing mutant 4 are in the stable state characteristic of nutrient-poor conditions.

Rapamycin Severely Weakens the mTOR-Raptor Interaction

In vivo, rapamycin, like nutrient deprivation, inhibits the activation of downstream effectors of mTOR, but exactly how the drug perturbs mTOR function is unknown. It was found that treatment of HEK293T cells with rapamycin or the addition of the drug to cell lysates significantly destabilized the mTOR-raptor complex (FIG. 10A). The effect was specific to rapamycin, as FK506, an immunosuppressant that also binds FKBP12 but does not target mTOR, had no effect on the interaction, nor did ethanol, the vehicle used for both drugs. However, when lysates were prepared in the presence of the cross-linker almost normal levels of raptor were recovered with mTOR (FIG. 10A). Therefore, as with nutrient stimulation and raptor mutant 5, rapamycin destabilizes the raptor-mTOR complex but does not abolish it in vivo.

The effect of increasing concentrations of rapamycin on the mTOR-raptor interaction in cells deprived of or stimulated with leucine was investigated in order to understand the inhibitory mechanism of rapamycin. Interestingly, irrespective of nutrient conditions, rapamycin dominantly destabilized the raptor-mTOR complex (FIG. 10B). The order of rapamycin addition and leucine deprivation did not matter as the drug had similar effects when it was added before or after leucine withdrawal. In addition, leucine-rich conditions enhanced the destabilizing effects of rapamycin, decreasing its EC50 for mTOR-raptor dissociation by about 3-fold when compared to leucine-poor conditions. A simple explanation for this latter result is that leucine-poor conditions lead to a decrease in the affinity between mTOR and FKBP12-rapamycin, likely by inducing a conformational change in the FKBP12-rapamycin binding site in mTOR. Alternatively, leucine deprivation likely increases the affinity between raptor and mTOR so that the complex is less susceptible to the destabilizing effects of FKBP12-rapamycin. The finding that the unstable and stable complexes found in nutrient-rich and poor conditions, respectively, are differentially sensitive to rapamycin provides further evidence that the raptor-mTOR complex can exist in two-binding states.

Discussion

Raptor Forms a Nutrient Sensitive Complex (NSC) with mTOR

Described herein is raptor, a 149-kDa protein that participates in the mTOR pathway and associates in a near stoichiometric ratio with mTOR to form a nutrient-sensitive complex (NSC). It was found that the strength of the association between raptor and mTOR modulates the kinase activity of mTOR and is controlled by cellular conditions known to regulate S6K1, such as nutrient availability, mitochondrial function and cell stress. The mTOR-raptor complex may have escaped prior detection because it is unstable under commonly used cell lysis solutions and is particularly sensitive to the detergent Triton X-100. Its identification was first made possible by stabilization of the association through the use of a reversible chemical cross-linker.

Raptor and mTOR associate under all cellular conditions but the stability of the complex changes with the activity of the pathway. Under nutrient-poor conditions the mTOR-raptor association is strong and high levels of the complexes are recovered even when cell lysates are prepared without the cross-linker. On the other hand, in nutrient-rich conditions, the association is weak and most of the complex readily falls apart in the absence of the cross-linker. These findings are consistent with a model in which mTOR and raptor are held together in a constitutive, easily disrupted association, which, under nutrient-poor conditions, is strengthened by an additional interaction(s) that also represses the kinase activity of mTOR. Thus, it is likely that at least two interactions exist between raptor and mTOR: a 'constitutive' interaction that is required for in vivo mTOR function and a 'nutrient sensitive' interaction that forms in the absence of nutrients and negatively regulates mTOR kinase activity (FIG. 10C). In support of this model, it was found that two raptor mutants associate with mTOR in ways that indicate that they have selective defects in the nutrient-sensitive interaction described above. The behavior of raptor mutant 5 is consistent with it having lost the nutrient-sensitive interaction and it appears to associate with mTOR only through the constitutive interaction. The behavior of raptor mutant 4 is consistent with it retaining both interactions but with the nutrient-sensitive interaction no longer being regulated by nutrients.

The molecular mechanisms by which raptor regulates mTOR function are unknown. The nutrient sensitive mTOR-raptor interaction could decrease the catalytic activity of mTOR by inducing a conformational change in the mTOR kinase domain (mechanism shown in FIG. 10C) or by sterically preventing substrates from accessing the mTOR active site. On the other hand, the constitutive interaction is clearly not required for in vitro kinase activity, since, as shown herein, raptor-depleted mTOR strongly phosphorylates S6K1. Previous studies have shown that to function in vivo mTOR requires more than its kinase activity because truncation and point mutants of mTOR that retain wild-type kinase activity cannot signal to S6K1 within mammalian cells (Brown et al., Nature 377:441-446 (1995); Sabatini et al., Science 284:1161-4. (1999)). The deletion and mutagenesis studies performed under nutrient-rich conditions and described herein, show that raptor makes extensive contacts with mTOR regions that are far from its kinase domain. Thus, it is likely that in vivo the constitutive mTOR-raptor interaction is required for a function other than mTOR kinase activity. A simple possibility, supported by the finding that a reduction in raptor levels also reduces mTOR levels, is that raptor is required for the proper folding and/or stability of mTOR. Raptor could also serve as an adaptor that brings substrates to the mTOR kinase domain and/or may be a determinant of the proper subcellular localization of mTOR.

Rapamycin Destabilizes the NSC Irrespective of Nutrient Conditions

Although rapamycin and nutrient deprivation similarly inhibit the activity of downstream components of the mTOR pathway, such as S6K and 4E-BP1, it was found that they have opposite effects on the mTOR-raptor interaction. Rapamycin destabilizes the interaction regardless of nutrient availability, and its potency for dissociation is increased under nutrient-rich conditions.

Several mechanisms can be proposed to account for the effects of FKBP12-rapamycin on the stability of the complex and to explain how the drug inhibits the pathway. Two appealing models will be considered here. In the first, FKBP12-rapamycin dislodges raptor from its nutrient-sensitive binding site on mTOR because it binds to mTOR at or near that site. By replacing raptor at this site, FKBP12-rapamycin would mimic raptor's inhibitory effect on the mTOR kinase that is manifested under nutrient poor conditions. A prediction of this model is that in vitro FKBP12-rapamycin should inhibit mTOR kinase activity, a result seen in many studies (Brown et al., Nature 377:441-446 (1995); Brunn et al., Nature 377:441-446 (1997); Brunn et al., Embo J. 15:5256-67 (1996); Burnett et al., PNAS 95:1432-1437. (1998); Isotani et al., J. Biol. Chem. 274:34493-8. (1999)). In the second model, FKBP12-rapamycin does not affect the nutrient-sensitive interaction but interferes with the constitutive mTOR-raptor interaction. Because this is a positive interaction required for the in vivo function of mTOR, its interference by FKBP12-rapamycin inhibits the pathway. Of course, it is also possible that rapamycin exerts its negative effects on the pathway independently of its perturbation of the mTOR-raptor complex, perhaps, as has been recently suggested (Fang et al., Science 294:1942-5 (2001)), by preventing the action of a small signaling molecule on mTOR.

Diverse Signals Converge on the Regulation of the NSC

How might changes in levels of diverse nutrients regulate the strength of the NSC association? Certainly, mTOR and/or raptor could be phosphorylated or modified by upstream 'nutrient sensors' that regulate their interaction. However, an alternate hypothesis is one in which the mTOR-raptor complex is itself the nutrient sensor. In this scenario, one or more intracellular molecules increase in concentration in nutrient-rich conditions and bind to raptor and/or mTOR, destabilizing the NSC and relieving raptor inhibition of the mTOR kinase (FIG. 10C). If a single molecular species sufficed to destabilize the interaction, its concentration would have to reflect the availability of both leucine and glucose, as well as the state of mitochondrial metabolism. Alternatively, destabilization could require several molecular species that are derived from distinct nutrients and act on multiple independent sites on the NSC. Because raptor and mTOR are large proteins with high potentials for small molecule-induced allosteric and conformational changes that may affect protein-protein interactions, the NSC appears well equipped for sensing multiple growth signals.

In this regard it is interesting that the mTOR-raptor interaction is mediated in part through the N-terminal portion of mTOR, which contains at least 16 HEAT repeats (Dennis et al., Curr. Opin. Genet. Dev. 9:49-54 (1999)). HEAT repeat-containing domains appear to posses substantial conformational flexibility and, for example, in β-importin undergo a twisting conformational change in superhelical structure that enables them to bind to distinct proteins for nuclear import (Lee et al., J. Mol. Biol. 302:251-649 (2000)). The importance of the HEAT motifs in the mTOR-raptor interaction might indicate that conformational changes in that region of mTOR play a role in regulating the nutrient-sensitive strength of the interaction. However, the results described herein also show that in addition to the HEAT repeats, sites in the C-terminal half of mTOR also contribute to the interaction.

It is worth noting that the interaction is exquisitely sensitive to the detergent Triton X-100. This indicates that a hydrophobic molecule, such as a lipid, plays a role in maintaining the interaction, or that Triton X-100 mimics a molecule that normally weakens it in vivo. Consistent with this possibility, mTOR is found in association with membrane fractions (Sabatini et al., Science 284:1161-4 (1999)), and phosphatidic acid (PA), a component of lipid membranes as well as a signaling molecule, has been shown to interact with mTOR and stimulate the pathway through unknown mechanisms (Fang et al., Science 294:1942-5 (2001)).

CONCLUSIONS

Using a chemical cross-linker and appropriate cell lysis conditions, it has been demonstrated that in vivo mTOR interacts with raptor, a protein that has a positive role required for the in vivo activity of the mTOR pathway and for cell growth. Under nutrient deprivation conditions, however, raptor also serves as a negative regulator of mTOR kinase activity. FKBP12-rapamycin may mimic the binding of raptor to a nutrient-sensitive site on mTOR, locking mTOR in the nutrient-poor state, or it may disrupt a constitutive interaction necessary for mTOR function. It is likely that the regulation of the mTOR-raptor interaction is a critical mechanism by which eukaryotic cells coordinate the rate of cell growth with different environmental conditions. Small molecules can be designed that perturb the mTOR-raptor association in subtler ways than rapamycin, allowing a finer pharmacological control of the TOR pathway than is currently possible.

While this invention has been particularly shown and described with references to preferred embodiments thereof, it will be understood by those skilled in the art that various changes in form and details may be made therein without departing from the scope of the invention encompassed by the appended claims.

What is claimed is:

1. An isolated complex comprising (i) comprising a polypeptide having an amino acid sequence at least 95% identical to SEQ ID NO: 2; and (ii) a mammalian mTOR polypeptide; wherein the polypeptide having an amino acid sequence at least 95% identical to SEQ ID NO:2, or the mTOR polypeptide, is fused to an epitope tag.

2. The isolated complex of claim 1, wherein the chimeric polypeptide comprises a polypeptide having an amino acid sequence identical to SEQ ID NO: 2.

3. A composition comprising the isolated complex of claim 1 and an antibody or antigen-binding fragment thereof that specifically binds to the chimeric polypeptide.

4. A composition comprising the isolated complex of claim 1 and reagents suitable for performing a kinase assay.

5. The complex of claim 1, further comprising a buffer appropriate to preserve the interaction between the polypeptide having an amino acid sequence at least 95% identical to SEQ ID NO: 2 and mTOR.

6. A composition comprising (a) an isolated complex comprising (i) a first polypeptide at least 95% identical to SEQ ID NO: 2; and (ii) a second polypeptide comprising a mammalian mTOR polypeptide; and (b) a buffer comprising a detergent appropriate to preserve the interaction between the polypeptide of SEQ ID NO: 2 and mTOR.

7. The composition of claim 6, further comprising an antibody or antigen-binding fragment thereof that specifically binds to the first or second mammalian polypeptide.

8. The composition of claim 6, wherein the first polypeptide is identical to SEQ ID NO: 2.

9. The composition of claim 6, wherein the first polypeptide or second polypeptide comprises an epitope tag.

10. The composition of claim 6, further comprising reagents suitable for performing a kinase assay.

* * * * *